United States Patent
Haseba

(10) Patent No.: US 8,586,803 B2
(45) Date of Patent: *Nov. 19, 2013

(54) CHLOROFLUOROBENZENE COMPOUND, OPTICALLY ISOTROPIC LIQUID CRYSTAL MEDIUM AND OPTICAL DEVICE

(71) Applicant: Yasuhiro Haseba, Chiba (JP)

(72) Inventor: Yasuhiro Haseba, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/689,779

(22) Filed: Nov. 30, 2012

(65) Prior Publication Data

US 2013/0085306 A1 Apr. 4, 2013

Related U.S. Application Data

(62) Division of application No. 12/782,078, filed on May 18, 2010, now Pat. No. 8,343,595.

(30) Foreign Application Priority Data

May 19, 2009 (JP) ................................. 2009-120438
Apr. 16, 2010 (JP) ................................. 2010-094824

(51) Int. Cl.
*C07C 43/225* (2006.01)
*C07C 25/13* (2006.01)
*C07C 25/18* (2006.01)

(52) U.S. Cl.
USPC .......... 570/127; 570/128; 570/129; 568/649; 568/656

(58) Field of Classification Search
USPC .................... 252/299.66; 568/642, 643, 656; 570/127, 128, 129
See application file for complete search history.

(56) References Cited

U.S. PATENT DOCUMENTS

| 7,722,789 | B2 * | 5/2010 | Aoki et al. | 264/102 |
| 8,343,595 | B2 * | 1/2013 | Haseba | 428/1.1 |
| 8,372,975 | B2 * | 2/2013 | Tanaka | 544/335 |
| 8,409,673 | B2 * | 4/2013 | Haseba et al. | 428/1.1 |
| 2009/0135368 | A1 * | 5/2009 | Haseba et al. | 349/183 |
| 2011/0242473 | A1 * | 10/2011 | Haseba et al. | 349/139 |

* cited by examiner

*Primary Examiner* — Shean C Wu

(74) *Attorney, Agent, or Firm* — Jianq Chyun IP Office

(57) ABSTRACT

A liquid crystal compound and a liquid crystal medium are described. The liquid crystal compound is stable to heat and light and has a large dielectric anisotropy and a large optical anisotropy. The liquid crystal medium has a wide temperature range of liquid crystal phase, a large optical anisotropy and a large dielectric anisotropy, and exhibits an optically isotropic liquid crystal phase. The liquid crystal compound has 4 or 5 benzene rings, one of which is a chlorofluorobenzene ring. The liquid crystal medium is characterized in containing the liquid crystal compound and a chiral dopant and exhibiting an optically isotropic liquid crystal phase.

10 Claims, 1 Drawing Sheet

CHLOROFLUOROBENZENE COMPOUND, OPTICALLY ISOTROPIC LIQUID CRYSTAL MEDIUM AND OPTICAL DEVICE

CROSS-REFERENCE TO RELATED APPLICATION

This application is a divisional application of and claims the priority benefit of the U.S. application Ser. No. 12/782,078, filed on May 18, 2010, now allowed, which claims the priority benefit of Japanese application Ser. No. 2009-120438 filed on May 19, 2009 and Japanese application Ser. No. 2010-094824 filed on Apr. 16, 2010. The entirety of each of the above-mentioned patent applications is hereby incorporated by reference herein and made a part of this specification.

BACKGROUND OF THE INVENTION

1. Field of the Invention

This invention relates to a liquid crystal compound useful as a material for an optical device, a liquid crystal medium and an optical device, and in particular, to a liquid crystal compound having a large dielectric anisotropy, a large optical anisotropy and good compatibility, and a liquid crystal medium with a wide temperature range of liquid crystal phase, a large dielectric anisotropy and a large optical anisotropy. This invention also relates to an optical device using the liquid crystal medium, and in particular, to an optical device that can be used in a wide temperature range and driven at a low voltage and can achieve a high-speed electro-optical response.

2. Description of Related Art

Liquid crystal display (LCD) devices utilizing liquid crystal compositions are widely used in displays of clocks, calculators, word processors and so on. These LCD devices utilize the optical anisotropy and the dielectric anisotropy, etc. of liquid crystal compounds. The operation modes of LCD devices mainly include phase change (PC), twisted nematic (TN), super twisted nematic (STN), bistable twisted nematic (BTN), electrically controlled birefringence (ECB), optically compensated bend (OCB), in-plane switching (IPS), vertical alignment (VA) and so on, which utilize one or more polarizers for display. Moreover, in recent years, more attentions have been paid to the mode where an electric field is applied to an optically isotropic liquid crystal phase to make the liquid crystal phase exhibit electrically controlled birefringence (Patent References 1-9 and Non-patent References 1-3).

Moreover, tunable filters, wavefront control devices, liquid-crystal lenses, aberration correction devices, aperture control devices and optical head devices, etc., which utilize the electrically controlled birefringence in a blue phase as one of optically isotropic liquid crystal phases, have been proposed (Patent References 10-12).

According to the driving mode, the LCD devices can be classified into passive matrix (PM) and active matrix (AM) types. The PM type is further classified into static type and multiplex type, etc., and the AM type is further classified into thin film transistor (TFT) type, metal insulator metal (MIM) type and so on.

Such LCD devices contain a liquid crystal composition with suitable properties. To improve the properties of an LCD device, the liquid crystal composition preferably has suitable properties. A liquid crystal compound as a component of a liquid crystal composition needs to have the following general properties: 1) high chemical stability and physical stability, 2) a high clear point (i.e., phase transition temperature from the liquid crystal phase to the isotropic phase), 3) a low lower-limit temperature of liquid crystal phase (i.e., nematic phase, cholesteric phase, smectic phase, optically isotropic liquid crystal phase like blue phase, etc.), 4) good compatibility with other liquid crystal compounds, 5) a suitable dielectric anisotropy, and 6) a suitable optical anisotropy.

Particularly, for an optically isotropic liquid crystal phase, a liquid crystal compound having a large dielectric anisotropy and a large optical anisotropy is preferred from the viewpoint of lowering the driving voltage.

When a liquid crystal composition containing a liquid crystal compound having stable chemical and physical properties as described in (1) is used in an LCD device, the voltage holding ratio is improved.

Further, a liquid crystal composition containing a liquid crystal compound with a high clear point or a low lower-limit temperature of liquid crystal phase as described in (2) and (3) can have a wide temperature range of nematic phase or optically isotropic liquid crystal phase, and thus can be used in a display device in a wide temperature range. A liquid crystal compound is generally mixed with a number of other liquid crystal compounds to prepare a liquid crystal composition, so as to exhibit properties difficult to develop by a single compound. Thus, a liquid crystal compound used in an LCD device preferably has good compatibility with other liquid crystal compounds as described in (4). In recent years, LCD devices with superior properties, especially display performances, for example, contrast, display capacity and response time, are especially required in the industry. In addition, regarding the liquid crystal material used, a liquid crystal composition with a low driving voltage is required. Furthermore, in order to drive an optical device driven in an optically isotropic liquid crystal phase with a low voltage, a liquid crystal compound with a large dielectric anisotropy and a large optical anisotropy is preferred.

It has been reported that chlorobenzene derivatives analogous to the compound of this invention have large dielectric anisotropy and large optical anisotropy (Patent Reference 13), but a compound having a chlorophenyl moiety and the good properties of the compound according to this invention have not been reported.

REFERENCES IN PRIOR ART

Patent References

[Patent Reference 1] Japanese Patent Publication No. 2003-327966
[Patent Reference 2] International Publication No. WO 2005/90520
[Patent Reference 3] Japanese Patent Publication No. 2005-336477
[Patent Reference 4] Japanese Patent Publication No. 2006-89622
[Patent Reference 5] Japanese Patent Publication No. 2006-299084
[Patent Reference 6] Japanese Patent Publication No. 2006-506477
[Patent Reference 7] Japanese Patent Publication No. 2006-506515
[Patent Reference 8] International Publication No. WO 2006/063662
[Patent Reference 9] Japanese Patent Publication No. 2006-225655
[Patent Reference 10] Japanese Patent Publication No. 2005-157109

[Patent Reference 11] International Publication No. WO 2005/80529
[Patent Reference 12] Japanese Patent Publication No. 2006-127707
[Patent Reference 13] International Publication No. WO 1998/023561

Non-Patent References

[Non-patent Reference 1] *Nature Materials*, 1, 64, (2002)
[Non-patent Reference 2] *Adv. Mater.*, 17, 96, (2005)
[Non-patent Reference 3] *Journal of the SID*, 14, 551, (2006)

SUMMARY OF THE INVENTION

Accordingly, this invention provides a liquid crystal compound that is stable to heat and light and is large in the optical anisotropy and the dielectric anisotropy. This invention also provides a liquid crystal medium that is stable to heat and light, has a wide temperature range of liquid crystal phase, a large optical anisotropy and a large dielectric anisotropy, and also exhibits an optically isotropic liquid crystal phase. This invention further provides various optical devices that contain the liquid crystal medium, can be used in a wide temperature range, and have a short response time, a high contrast and a low driving voltage.

This invention provides a liquid crystal compound, a liquid crystal medium (liquid crystal composition or polymer/liquid crystal composite) and an optical device containing the liquid crystal medium, which are described as follows.

[1] A compound, represented by formula (1):

group formed by substituting arbitrary —$CH_2$— in the alkyl with —O—, —S—, —COO—, —OCO—, —CH=CH—, —CF=CF— or —C≡C— may be substituted with halogen or $C_{1-3}$ alkyl; $Z^1$, $Z^2$, $Z^3$, $Z^4$ and $Z^5$ are independently a single bond or —$CF_2O$— but are not all single bonds; $L^1$, $L^2$, $L^3$, $L^4$ and $L^5$ are independently hydrogen or fluorine; $X^1$ is hydrogen, halogen, —C≡N, —N=C=S, —C≡C—C≡N, —$SF_5$, or $C_{1-10}$ alkyl in which arbitrary —$CH_2$— may be substituted with —O—, —S—, —CH=CH— or —C≡C— and arbitrary hydrogen may be substituted with halogen; m is 0, 1, or 2, n and o are independently 0 or 1, and 1≤m+n+o≤2; and when m is 2, the plural $L^1$ may be different from each other and the plural $Z^2$ may be different from each other.

[2] The liquid crystal compound of [1], where in formula (1), $R^1$ is $C_{1-20}$ alkyl in which arbitrary —$CH_2$— may be substituted with —O—, —COO— or —CH=CH—; and $X^1$ is halogen, —C≡N, —N=C=S, or $C_{1-10}$ alkyl in which two or more hydrogen atoms are substituted with fluorine and arbitrary —$CH_2$— may be substituted with —O—, —S—, —CH=CH— or

[3] The liquid crystal compound of [1] or [2], where in formula (1), $R^1$ is $C_{1-20}$ alkyl, $C_{2-21}$ alkenyl or $C_{1-19}$ alkoxy, and $X^1$ is fluorine, chlorine, —$CF_3$ or —$OCF_3$.

[4] The liquid crystal compound of any one of [1] to [3], where in formula (1), $R^1$ is $C_{1-20}$ alkyl, and $X^1$ is fluorine, chlorine or —$CF_3$.

[5] The liquid crystal compound of any one of [1] to [4], wherein m+n+o=1.

[6] The liquid crystal compound of any one of [1] to [4], wherein m+n+o=2.

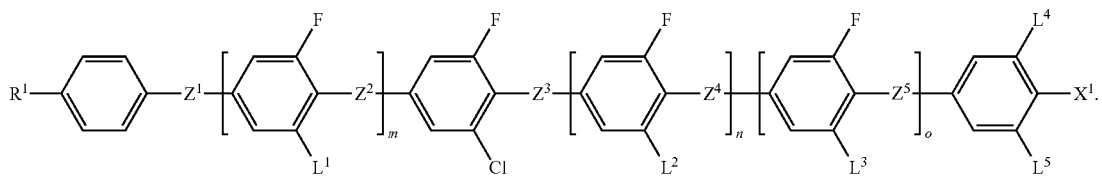

(1)

In formula (1), $R^1$ is hydrogen or $C_{1-20}$ alkyl in which arbitrary —$CH_2$— may be substituted with —O—, —S—, —COO—, —OCO—, —CH=CH—, —CF=CF— or —C≡C—, and arbitrary hydrogen in the alkyl and in the

[7] The liquid crystal compound of any one of [1] to [4], represented by any one of formulae (1-1B), (1-1C), (1-1E), (1-1F) and (1-2A) to (1-2C).

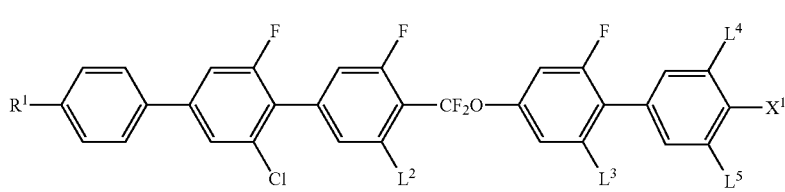

(1-1B)

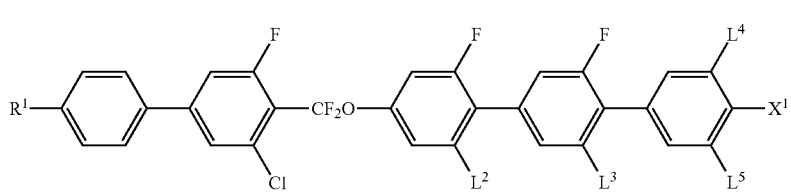

(1-1C)

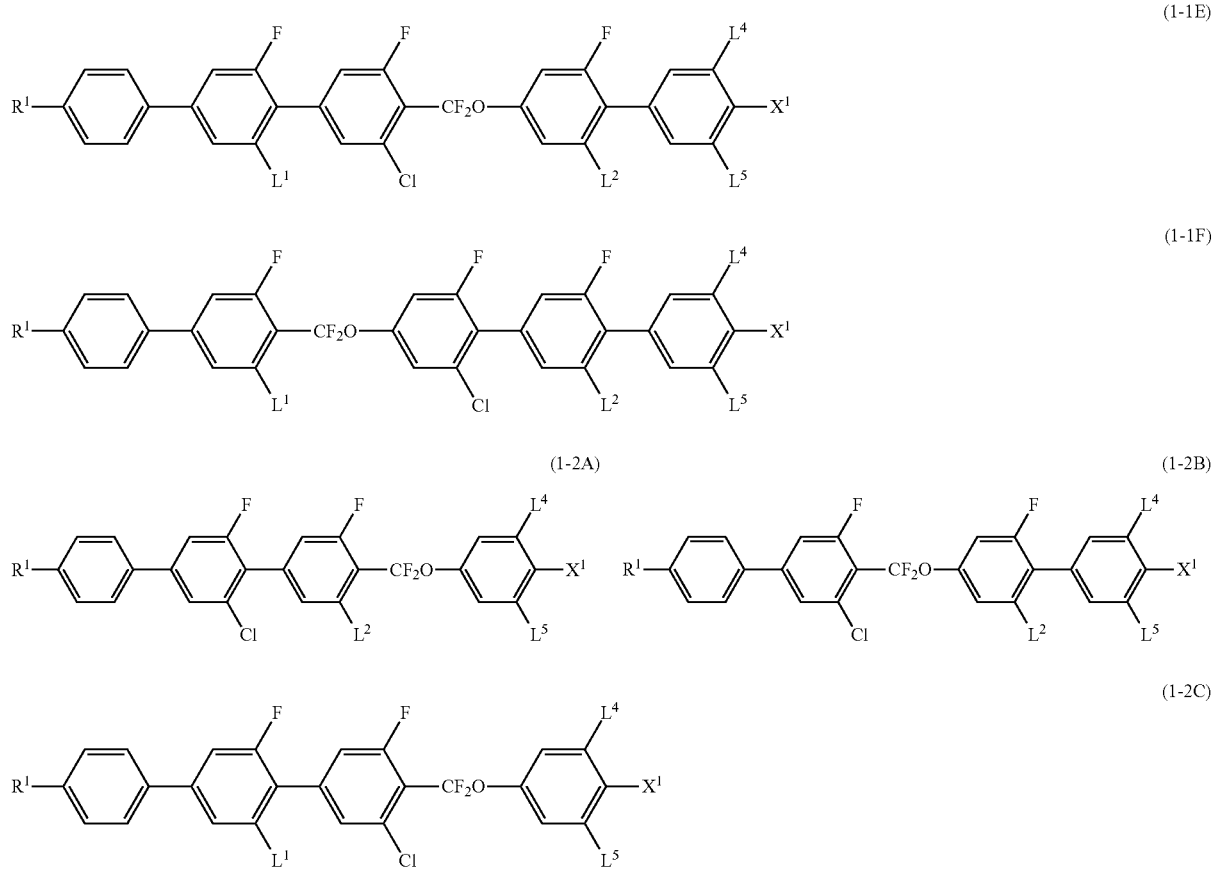

In the formulae, $R^1$ has a structure shown in formulae (CHN-1) to (CHN-8) in which $R^{1a}$ is hydrogen or $C_{1-10}$ alkyl, and $X^1$ is fluorine, chlorine, —$CF_3$ or —$OCF_3$.

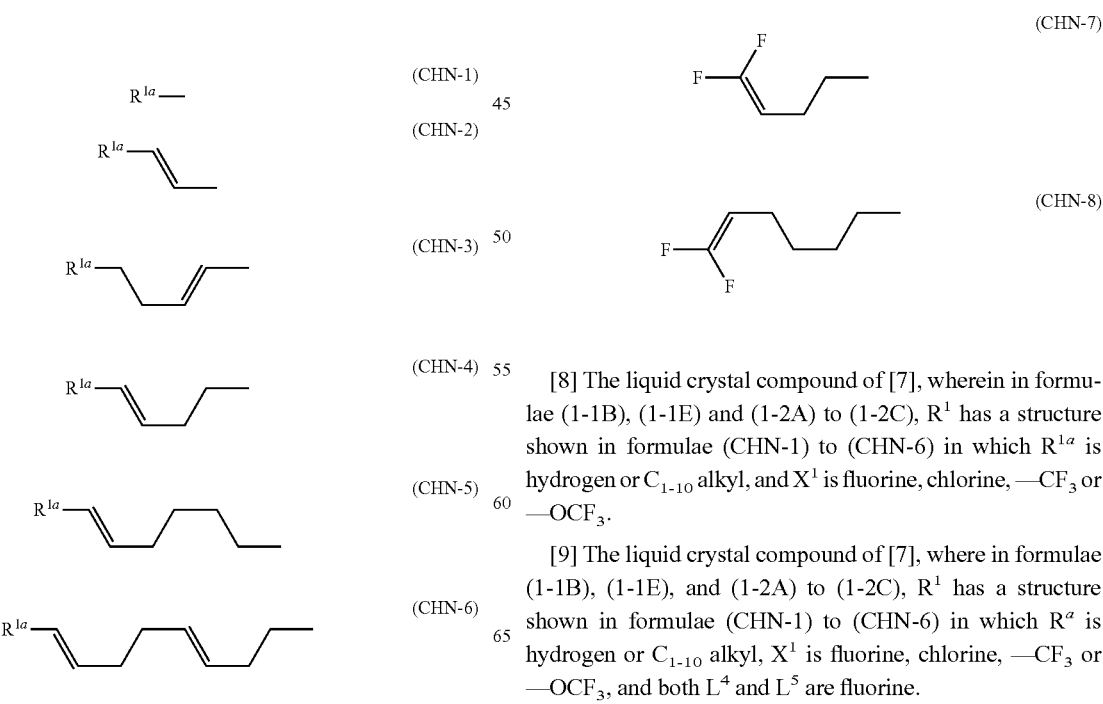

[8] The liquid crystal compound of [7], wherein in formulae (1-1B), (1-1E) and (1-2A) to (1-2C), $R^1$ has a structure shown in formulae (CHN-1) to (CHN-6) in which $R^{1a}$ is hydrogen or $C_{1-10}$ alkyl, and $X^1$ is fluorine, chlorine, —$CF_3$ or —$OCF_3$.

[9] The liquid crystal compound of [7], where in formulae (1-1B), (1-1E), and (1-2A) to (1-2C), $R^1$ has a structure shown in formulae (CHN-1) to (CHN-6) in which $R^a$ is hydrogen or $C_{1-10}$ alkyl, $X^1$ is fluorine, chlorine, —$CF_3$ or —$OCF_3$, and both $L^4$ and $L^5$ are fluorine.

[10] A liquid crystal compound, represented by formula (1-1B-a) or (1-2A-a):

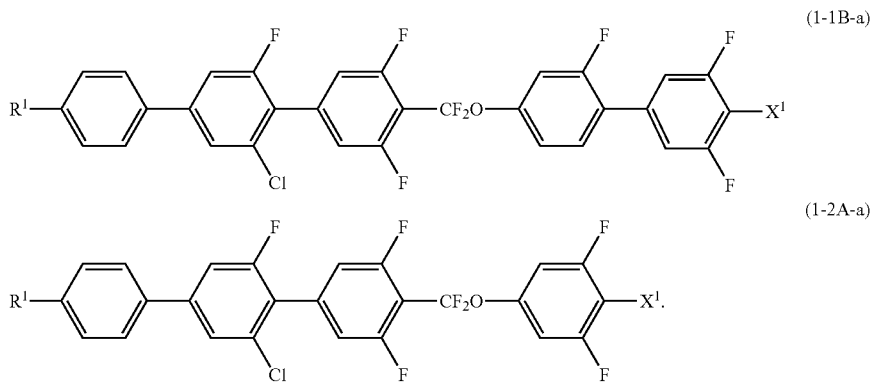

In the formulae, $R^1$ is $C_{1-20}$ alkyl or $C_{2-20}$ alkenyl, and $X^1$ is fluorine or —$CF^3$.

[11] A liquid crystal composition, containing the compound of any one of [1] to [10] and a chiral dopant, and exhibiting an optically isotropic liquid crystal phase.

[12] The liquid crystal composition of [11], further containing at least one compound selected from the group consisting of compounds represented by formulae (2), (3) and (4).

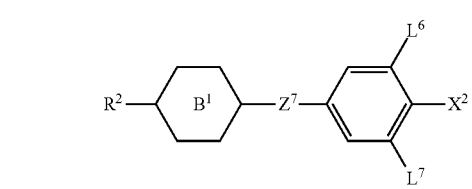

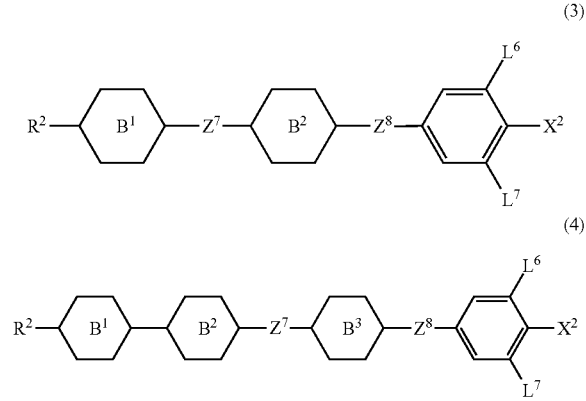

In the formulae, $R^2$ is $C_{1-10}$ alkyl or $C_{2-10}$ alkenyl, and in the alkyl and the alkenyl arbitrary hydrogen may be substituted with fluorine and arbitrary —$CH_2$— may be substituted with —O—; $X^2$ is fluorine, chlorine, —$OCF_3$, —$OCHF_2$, —$CF_3$, —$CHF_2$, —$CH_2F$, —$OCF_2CHF_2$ or —$OCF_2CHFCF_3$; rings $B^1$, $B^2$ and $B^3$ are independently 1,4-cyclohexylene, 1,3-dioxan-2,5-diyl, pyrimidin-2,5-diyl, tetrahydropyran-2,5-diyl, 1,4-phenylene, naphthalene-2,6-diyl, 1,4-phenylene in which arbitrary hydrogen is substituted with fluorine, or naphthalene-2,6-diyl in which arbitrary hydrogen is substituted with fluorine or chlorine; $Z^7$ and $Z^8$ are independently —$(CH_2)_2$—, —$(CH_2)_4$—, —COO—, —$CF_2O$—, —$OCF_2$—, —CH=CH—, —C≡C—, —$CH_2O$— or a single bond; and $L^6$ and $L^7$ are independently hydrogen or fluorine.

[13] The liquid crystal composition of [11], further containing at least one compound selected from the group consisting of compounds represented by formula (5).

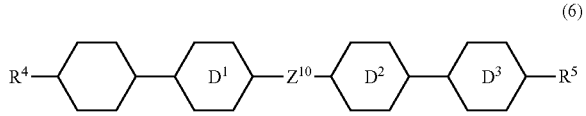

In the formula, $R^3$ is $C_{1-10}$ alkyl or $C_{2-10}$ alkenyl, and in the alkyl and the alkenyl arbitrary hydrogen may be substituted with fluorine and arbitrary —$CH_2$— may be substituted with —O—; $X^3$ is —C≡N or —C≡C—C≡N; rings $C^1$, $C^2$ and $C^3$ are independently 1,4-cyclohexylene, 1,4-phenylene, 1,4-phenylene in which arbitrary hydrogen is substituted with fluorine, naphthalene-2,6-diyl, naphthalene-2,6-diyl in which arbitrary hydrogen is substituted with fluorine or chlorine, 1,3-dioxan-2,5-diyl, tetrahydropyran-2,5-diyl or pyrimidin-2,5-diyl; $Z^9$ is —$(CH_2)_2$—, —COO—, —$CF_2O$—, —$OCF_2$—, —C≡C—, —$CH_2O$— or a single bond; $L^8$ and $L^9$ are independently hydrogen or chlorine; and r is 1 or 2, s is 0 or 1, and r+s=0, 1 or 2.

[14] The liquid crystal composition of [11], further containing at least one compound selected from the group consisting of compounds represented by formula (6).

(6)

In the formula, $R^4$ and $R^5$ are independently a $C_{1-10}$ alkyl or a $C_{2-40}$ alkenyl, and in the alkyl and the alkenyl arbitrary hydrogen may be substituted with fluorine and arbitrary —$CH_2$— may be substituted with —O—; rings $D^1$, $D^2$, and $D^3$ are independently 1,4-cyclohexylene, pyrimidin-2,5-diyl, 1,4-phenylene, 2-fluoro-1,4-phenylene, 3-fluoro-1,4-phenylene or 2,5-difluoro-1,4-phenylene; and $Z^{10}$ is —C≡C—, —COO—, —(CH$_2$)$_2$—, —CH=CH— or a single bond.

[15] The liquid crystal composition of [12], further containing at least one compound selected from the group consisting of compounds represented by formula (5) of [13].

[16] The liquid crystal composition of [12], further containing at least one compound selected from the group consisting of compounds represented by formula (6).

[17] The liquid crystal composition of [13], further containing at least one compound selected from the group consisting of compounds represented by formula (6).

[18] The liquid crystal composition of [11], further containing at least one compound selected from the group consisting of compounds represented by formulae (7), (8), (9) and (10).

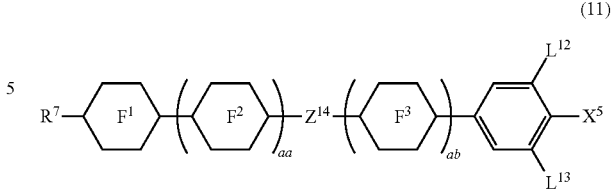

(11)

In the formula, $R^7$ is $C_{1-10}$ alkyl, $C_{2-10}$ alkenyl or $C_{2-10}$ alkynyl, and in the alkyl, the alkenyl and the alkynyl arbitrary hydrogen may be substituted with fluorine and arbitrary —CH$_2$— may be substituted with —O—; $X^5$ is —C≡N, —N=C=S or —C≡C—C≡N; rings $F^1$, $F^2$ and $F^3$ are inde-

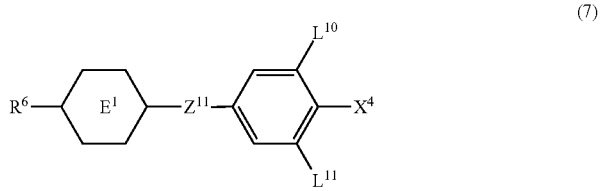

(7)

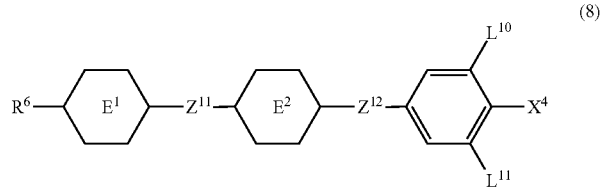

(8)

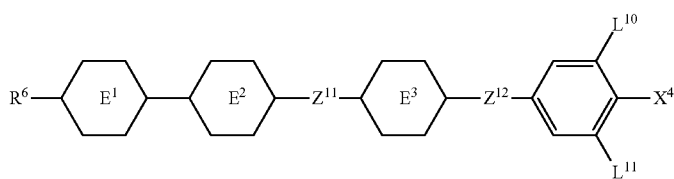

(9)

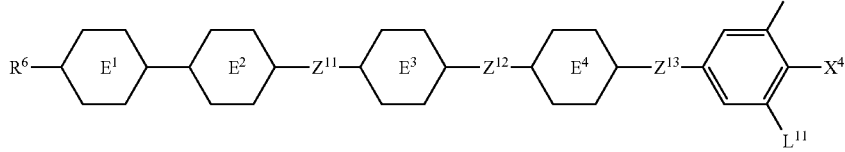

(10)

In the formulae, $R^6$ is $C_{1-10}$ alkyl, $C_{2-10}$ alkenyl or $C_{2-10}$ alkynyl, and in the alkyl, the alkenyl and the alkynyl arbitrary hydrogen may be substituted with fluorine and arbitrary —CH$_2$— may be substituted with —O—; $X^4$ is fluorine, chlorine, —SF$_5$, —OCF$_3$, —OCHF$_2$, —CF$_3$, —CHF$_2$, —CH$_2$F, —OCF$_2$CHF$_2$ or —OCF$_2$CHFCF$_3$; rings $E^1$, $E^2$, $E^3$ and $E^4$ are independently 1,4-cyclohexylene, 1,3-dioxan-2,5-diyl, pyrimidin-2,5-diyl, tetrahydropyran-2,5-diyl, 1,4-phenylene, naphthalene-2,6-diyl, 1,4-phenylene in which arbitrary hydrogen is substituted with fluorine or chlorine, or naphthalene-2,6-diyl in which arbitrary hydrogen is substituted with fluorine or chlorine; $Z^{11}$, $Z^{12}$ and $Z^{13}$ are independently —(CH$_2$)$_2$—, —(CH$_2$)$_4$—, —COO—, —CF$_2$O—, —OCF$_2$—, —CH=CH—, —C≡C—, —CH$_2$O— or a single bond, and when any one of the rings $E^1$, $E^2$, $E^3$ and $E^4$ is 3-chloro-5-fluoro-1,4-phenylene, $Z^{11}$, $Z^{12}$ and $Z^{13}$ are not —CF$_2$O—; and $L^{10}$ and $L^{11}$ are independently hydrogen or fluorine.

[19] The liquid crystal composition of [11], further containing at least one compound selected from a group consisting of compounds represented by formula (11).

pendently 1,4-cyclohexylene, 1,4-phenylene, 1,4-phenylene in which arbitrary hydrogen is substituted with fluorine or chlorine, naphthalene-2,6-diyl, naphthalene-2,6-diyl in which arbitrary hydrogen is substituted with fluorine or chlorine, tetrahydropyran-2,5-diyl or pyrimidin-2,5-diyl; $Z^{14}$ is —(CH$_2$)$_2$—, —COO—, —CF$_2$O—, —OCF$_2$—, —C≡C—, —CH$_2$O— or a single bond; $L^{12}$ and $L^{13}$ are independently hydrogen or fluorine; and aa is 0, 1 or 2, ab is 0 or 1, and aa+ab is 0, 1 or 2.

[20] The liquid crystal composition of any one of [11] to [19], containing at least one antioxidant, at least one UV absorbent, or at least one antioxidant and at least one UV absorbent.

[21] The liquid crystal composition of any one of [11]-[20], where the optically isotropic liquid crystal phase does not exhibit two or more colors of diffracted light.

[22] The liquid crystal composition of any one of [11] to [20], where the optically isotropic liquid crystal phase exhibits two or more colors of diffracted light.

[23] The liquid crystal composition of [21] or [22], obtained by adding a chiral dopant to a composition having a temperature difference of 3-150° C. between the upper-limit temperature and the lower-limit temperature of co-existence of a chiral nematic phase and an isotropic phase.

[24] The liquid crystal composition of [21] or [22], obtained by adding a chiral dopant to a composition having a temperature difference of 5-150° C. between the upper-limit temperature and the lower-limit temperature of co-existence of a chiral nematic phase and an isotropic phase.

[25] The liquid crystal composition of [21] or [22], obtained by adding a chiral dopant to a composition having a temperature difference of 3-150° C. between the upper-limit temperature and the lower-limit temperature of co-existence of a nematic phase and an isotropic phase.

[26] The liquid crystal composition of any one of [11] to [25], wherein the content of the chiral dopant is 1-40 wt % relative to the total weight of the liquid crystal composition.

[27] The liquid crystal composition of any one of [11] to [25], wherein the content of the chiral dopant is 5-15 wt % relative to the total weight of the liquid crystal composition.

[28] The liquid crystal composition of [26] or [27], exhibiting a chiral nematic phase at any temperature in the range of 70° C. to −20° C., and having a helical pitch of 700 nm or less within at least a part of the temperatures in the range.

[29] The liquid crystal composition of any one of [26] to [28], wherein the chiral dopant includes at least one compound selected from the group consisting of compounds represented by formulae (K1) to (K5).

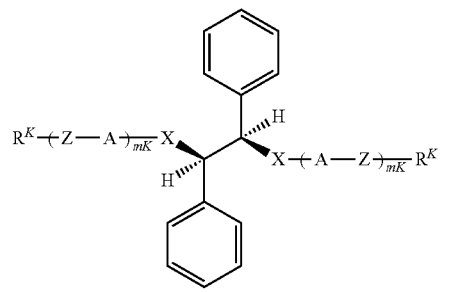
(K1)

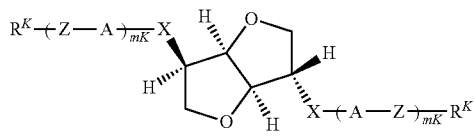
(K2)

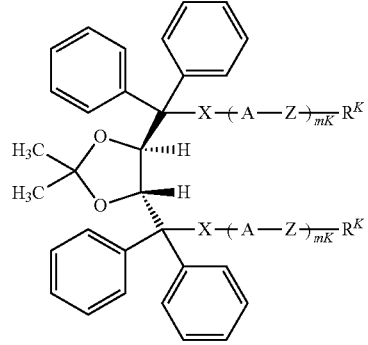
(K3)

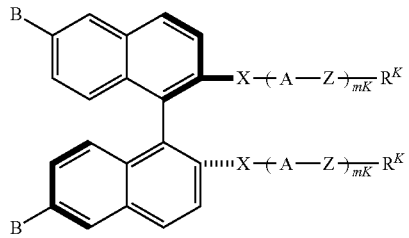
(K4)

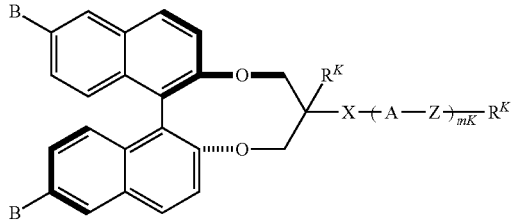
(K5)

In formulae (K1)-(K5), the plural $R^K$ are independently hydrogen, halogen, —N=C=O, —N=C=S, or $C_{1-20}$ alkyl in which arbitrary —$CH_2$— may be substituted with —O—, —S—, —COO—, —CH=CH—, —CF=CF— or —C≡C— and arbitrary hydrogen may be substituted with halogen; the plural A are independently an aromatic or non-aromatic 3- to 8-membered ring or a fused ring of 9 or more carbons, and in these rings arbitrary hydrogen may be substituted with halogen, $C_{1-3}$ alkyl or $C_{1-3}$ haloalkyl, —$CH_2$— may be substituted with —O—, —S— or —NH—, and —CH= may be substituted with —N=; the plural B are independently hydrogen, halogen, $C_{1-3}$ alkyl, $C_{1-3}$ haloalkyl, aromatic or non-aromatic 3- to 8-membered ring, or a fused ring of 9 or more carbons, and in these rings arbitrary hydrogen may be substituted with halogen, $C_{1-3}$ alkyl or $C_{1-3}$ haloalkyl, —$CH_2$— may be substituted with —O—, —S— or —NH—, and —CH= may be substituted with —N=; the plural Z are independently a single bond, or $C_{1-8}$ alkylene in which arbitrary —$CH_2$— may be substituted with —O—, —S—, —COO—, —CSO—, —OCS—, —N=N—, —CH=N—, —N=CH—, —CF=CF—, —CF=CF— or —C≡C— and arbitrary hydrogen may be substituted with halogen; X is a single bond, —COO—, —OCO—, —$CH_2$O—, —$OCH_2$—, —$CF_2$O—, —$OCF_2$— or —$CH_2CH_2$—; and mK is an integer of 1-4.

[30] The liquid crystal composition of any one of [26] to [28], wherein the chiral dopant includes at least one compound selected from the group consisting of compounds represented by formulae (K2-1) to (K2-8), (K4-1) to (K4-6) and (K5-1) to (K5-3).

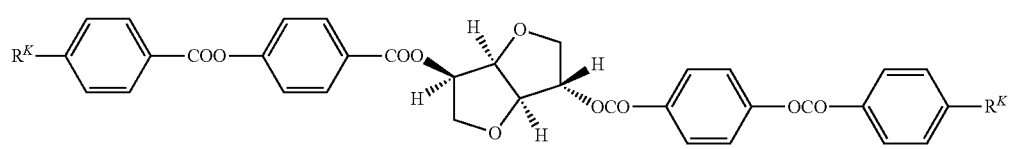
(K2-1)

-continued
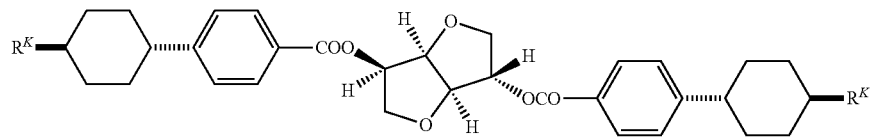
(K2-2)
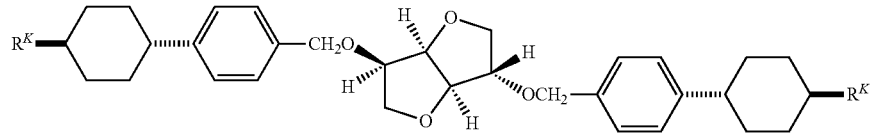
(K2-3)
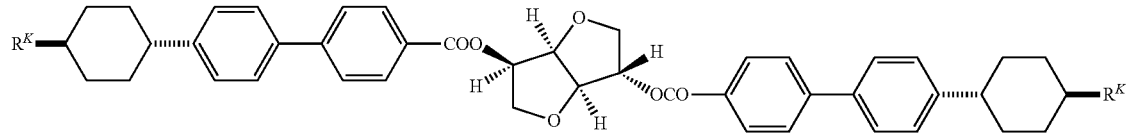
(K2-4)
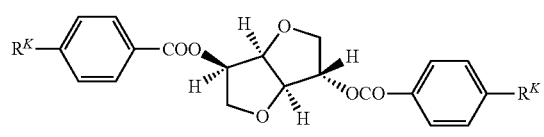
(K2-5)
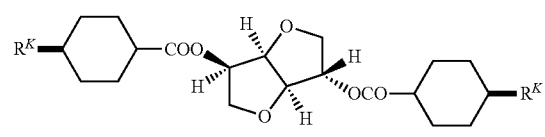
(K2-6)
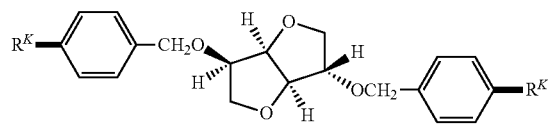
(K2-7)
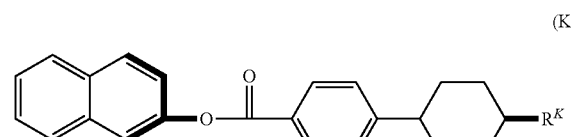
(K2-8)
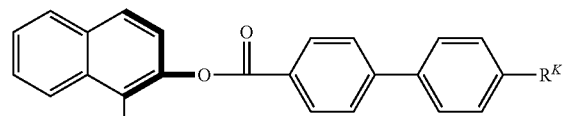
(K4-1)
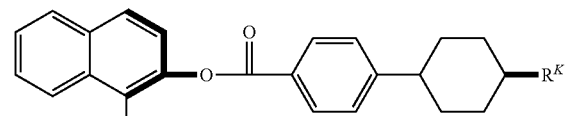
(K4-2)
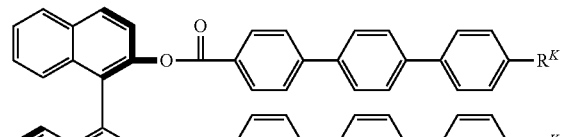
(K4-5)
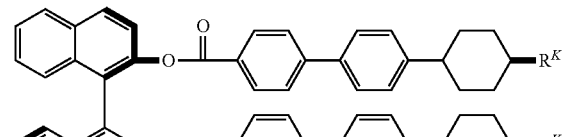
(K4-6)
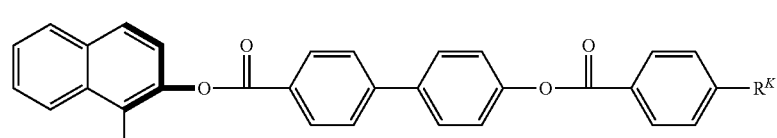
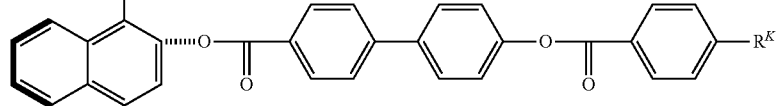
(K4-3)

(K4-4)

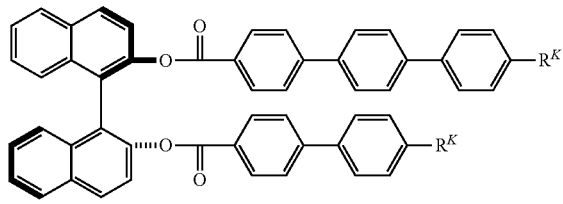

(K5-1)

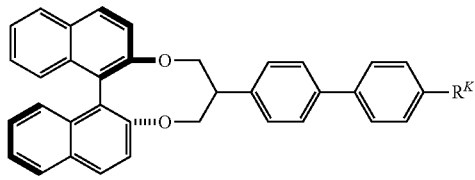

(K5-2)

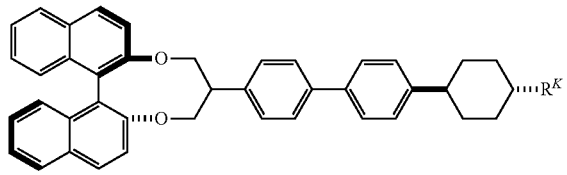

(K5-3)

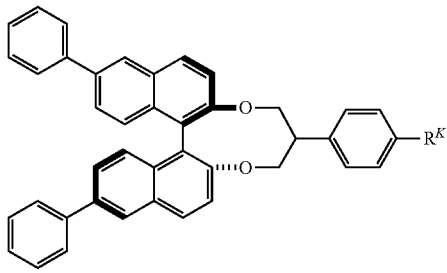

The plural $R^K$ are independently $C_{3-10}$ alkyl, in which —CH$_2$— adjacent to a ring may be substituted with —O— and arbitrary —CH$_2$— may be substituted with —CH=CH—.

[31] A mixture, containing the liquid crystal composition of any one of [11] to [30], and a polymerizable monomer.

[32] The mixture of [31], wherein the polymerizable monomer is a photo-polymerizable monomer or a thermo-polymerizable monomer.

[33] A polymer/liquid crystal composite material, which is obtained by polymerizing the mixture of [31] or [32] and used in a device driven in an optically isotropic liquid crystal phase.

[34] The polymer/liquid crystal composite material of [33], which is obtained by polymerizing the mixture of [31] or [32] in an isotropic phase or an optically isotropic liquid crystal phase.

[35] The polymer/liquid crystal composite material of [33] or [34], wherein the polymer contained therein has a mesogen moiety.

[36]. The polymer/liquid crystal composite material of any one of [33] to [35], wherein the polymer contained therein has a cross-linked structure.

[37] The polymer/liquid crystal composite material of any one of [33] to [36], where the content of the liquid crystal composition is 60-99 wt %, and the content of the polymer is 1-40 wt %.

[38] An optical device, including a liquid crystal medium disposed between two substrates having electrodes on either or both surfaces thereof and electric field applying means for applying an electric field to the liquid crystal medium via the electrodes, wherein the liquid crystal medium is the liquid crystal composition of any one of [26] to [30], or the polymer/liquid crystal composite material of any one of [33] to [37].

[39] An optical device, including: two substrates having electrodes on either or both surfaces thereof and at least one being transparent, a liquid crystal medium disposed between the substrates, a polarizer disposed outside of the substrates, and electric field applying means for applying an electric field to the liquid crystal medium via the electrodes, wherein the liquid crystal medium is the liquid crystal composition of any one of [26] to [30], or the polymer/liquid crystal composite material of any one of [33] to [37].

[40] The optical device of [39], wherein on at least one of the set of substrates, the electrodes are constructed in a manner such that the electric field is applied in at least two directions.

[41] The optical device of [39], wherein on one or two of the set of substrates arranged in parallel, the electrodes are constructed in a manner such that the electric field is applied in at least two directions.

[42] The optical device of any one of [38] to [41], wherein the electrodes are arranged in a matrix form to form pixel electrodes, and each pixel is provided with an active element being a thin film transistor (TFT).

In this invention, the so-called "liquid crystal medium" is a generic term of liquid crystal composition and polymer/liquid crystal composite. Further, the so-called "optical device" refers to various devices utilizing electrooptic effect to achieve optical modulation or optical switching, etc., for example, display devices (LCD devices), and optical modulation devices used in optical communication systems, optical information processing or various sensor systems. Regarding light modulation utilizing refractive index change of an optically isotropic liquid crystal medium caused by voltage application, the Kerr effect is known. The Kerr effect is an effect that the electric birefringence $\Delta n(E)$ is proportional to the square of the electric field E, i.e., $\Delta n(E)=K\cdot\lambda\cdot E^2$ (K=Kerr constant, $\lambda$=wavelength) for a material exhibiting the Kerr effect. Herein, "electric birefringence" refers to the optical anisotropy induced by applying an electric field to an isotropic liquid crystal medium.

The terms used in this specification are defined as follows. "Liquid crystal compound" is a generic term of a compound having a liquid crystal phase like nematic phase and smectic phase, and a compound having no liquid crystal phase but being useful as a component of a liquid crystal composition. "Chiral dopant" is an optical active compound, which is added to impart necessary twisted molecular arrangement to a liquid crystal composition. "LCD device" is a generic term of an LCD panel and an LCD module. "Liquid crystal compound", "liquid crystal composition" and "LCD device" are often simply called "compound", "composition" and "device", respectively. Further, for example, the upper-limit temperature of a liquid crystal phase is the liquid crystal phase-isotropic phase transition temperature, often simply called "clear point" or "upper-limit temperature", and the lower-limit temperature of a liquid crystal phase is often simply called "lower-limit temperature". A compound of formula (1) is often simply called compound (1); this rule also applies to the compounds of formula (2), etc. In formulae (1)-(19), the symbols B, D, and E, etc. surrounded by hexagons correspond to ring B, ring D and ring E, etc., respectively. The compound content by percentage is weight percent (wt %) relative to the total weight of the composition. A plurality of identical symbols such as ring $A^1$, $Y^1$ or B is included in the same or different formulae; however, the groups represented by these symbols can be identical or different.

"Arbitrary" denotes not only "arbitrary position", but also "arbitrary number of atom(s) or group(s)", except for the case where the number is 0. The expression "arbitrary A may be substituted with B, C or D" not only means "arbitrary A may be substituted with B, arbitrary A may be substituted with C and arbitrary A may be substituted with D", but also means "arbitrary plurality of A may be substituted with at least two of B-D". For example, the scope of the alkyl in which arbitrary —$CH_2$— may be substituted with —O— or —CH═CH— includes alkyl, alkenyl, alkoxy, alkoxyalkyl, alkoxyalkenyl and alkenyloxyalkyl, etc. Further, in this invention, a case in which two contiguous —$CH_2$— are substituted with —O— to form —O—O— is unsuitable, and a case in which terminal —$CH_2$— of alkyl is substituted with —O— is also unsuitable. This invention will be further described below. The terminal groups, rings and linking groups etc. of the compound of formula (1) will also be illustrated by way of preferred examples.

The liquid crystal compound of this invention is stable to heat and light, etc., and has a large dielectric anisotropy and a large optical anisotropy. The liquid crystal composition of this invention is stable to heat and light, etc., has a high upper-limit and a low lower-limit temperature of optically isotropic liquid crystal phase, and has a low driving voltage in a device driven in an optically isotropic liquid crystal phase. The polymer/liquid crystal composite material of this invention also has an optically isotropic liquid crystal phase, exhibits a high upper-limit and low lower-limit temperature of the optically isotropic liquid crystal phase, and has a low driving voltage in a device driven in an optically isotropic liquid crystal phase.

The optical device of this invention driven in an optically isotropic liquid crystal phase has a wide temperature range for use, a short response time, a high contrast, and a low driving voltage.

Figure 1:
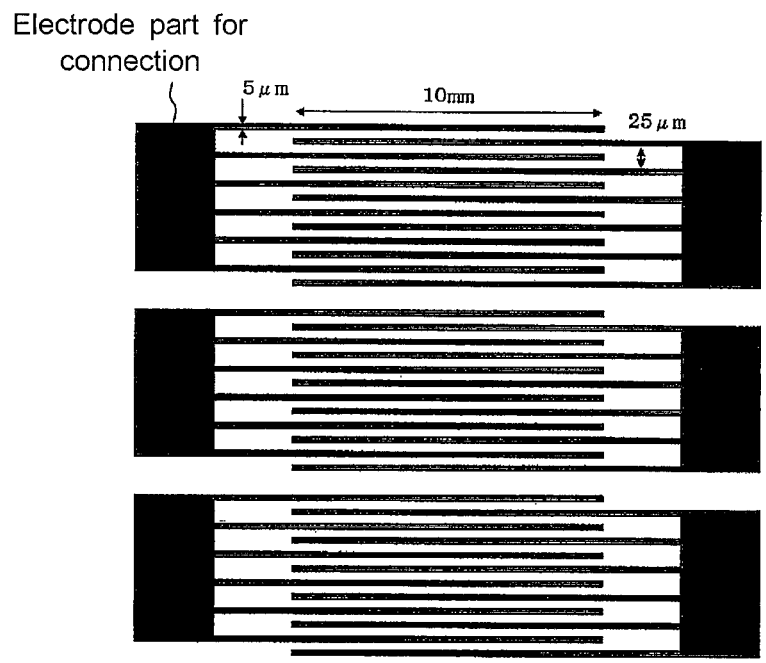
FIG. 1 shows the comb-like electrode substrate used in Application Example 1.

DESCRIPTION OF THE EMBODIMENTS 1-1. Compound (1)

The liquid crystal compound of this invention is the compound of formula (1). A first aspect of this invention relates to the liquid crystal compound of formula (1). The compound of formula (1) is first described.

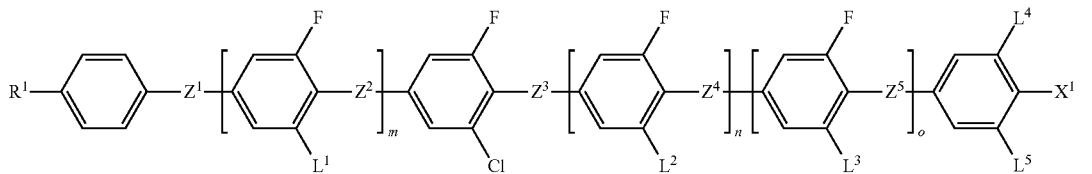

In formula (1), $R^1$ is hydrogen or $C_{1-20}$ alkyl in which arbitrary —$CH_2$— may be substituted with —O—, —S—, —COO—, —OCO—, —CH═CH—, —CF═CF— or —C≡C—, and arbitrary hydrogen in the alkyl and in the group formed by substituting arbitrary —$CH_2$— in the alkyl with —O—, —S—, —COO—, —OCO—, —CH═CH—, —CF═CF— or may be substituted with halogen or $C_{1-3}$ alkyl.

For example, examples of the groups formed by substituting arbitrary —$CH_2$— in $CH_3(CH_2)_3$— with —O—, —S— or —CH═CH— are $CH_3(CH_2)_2O$—, $CH_3$—O—$(CH_2)_2$—, $CH_3$—O—$CH_2$—O—, $CH_3(CH_2)_2S$—, $CH_3$—S—$(CH_2)_2$—, $CH_3$—S—$CH_2$—S—, $CH_2$═CH—$(CH_2)_3$—, $CH_3$—CH═CH—$(CH_2)_2$—, $CH_3$—CH═CH—$CH_2O$—, $CH_3CH_2C$≡C—, and the like. For example, examples of the group formed by substituting arbitrary hydrogen with halogen in $CH_3(CH_2)_3$— or in a group formed by substituting arbitrary —$CH_2$— in $CH_3(CH_2)_3$— with —O—, —C≡C— or —CH═CH— are $ClCH_2(CH_2)_3$—, $CF_2$═CH—$(CH_2)_3$—, $CH_2F(CH_2)_2O$— and $CH_2FCH_2C$≡C—.

For such $R^1$, a linear group is preferred to a branched group. When $R^1$ is a branched group, a group having optical activity is preferred. The preferred stereo-configuration of —CH═CH— in alkenyl depends on the position of the double bond. The trans configuration is preferred for alkenyl having the double bond at an odd position, such as —CH═CHCH_3, —CH═CHC_2H_5, —CH═CHC_3H_7, —CH═CHC_4H_9, —C_2H_4CH═CHCH_3 and —C_2H_4CH═CHC_2H_5. The cis-configuration is preferred for alkenyl having the double bond at an even position, such as —CH_2CH═CHCH_3, —CH_2CH═CHC_2H_5 and —CH_2CH═CHC_3H_7. An alkenyl compound having a preferred stereo-configuration has a high upper-limit temperature, or a wide temperature range of liquid crystal phase, which is detailed in *Mol. Cryst. Liq. Cryst.*, 1985, 131, 109 and *Mol. Cryst. Liq. Cryst.*, 1985, 131, 327.

Alkyl can be linear or branched; specific examples thereof include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Alkoxy can be linear or branched; specific examples thereof include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Alkoxyalkyl can be linear or branched; specific examples thereof include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

Alkenyl can be linear or branched; specific examples thereof include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

Alkenyloxy can be linear or branched; specific examples thereof include —OCH$_2$CH=CH$_2$, —OCH$_2$CH=CHCH$_3$ and —OCH$_2$CH=CHC$_2$H$_5$.

Alkynyl can be linear or branched; specific examples thereof include —C≡CH, —C≡CCH$_3$, —CH$_2$C≡CH, —C≡CC$_2$H$_5$, —CH$_2$C≡CCH$_3$, —(CH$_2$)$_2$—C≡CH, —C≡CC$_3$H$_7$, —CH$_2$C≡CC$_2$H$_5$, —(CH$_2$)$_2$—C≡CCH$_3$ and —C≡C(CH$_2$)$_5$.

R$^1$ preferably has a structure shown in formulae (CHN-1) to (CHN-17). Herein, R$^{1a}$ is hydrogen or C$_{1-10}$ alkyl. Preferably, R$^1$ has a structure shown in (CHN-1) to (CHN-8), more preferably (CHN-1) to (CHN-6), and particularly preferably (CHN-1).

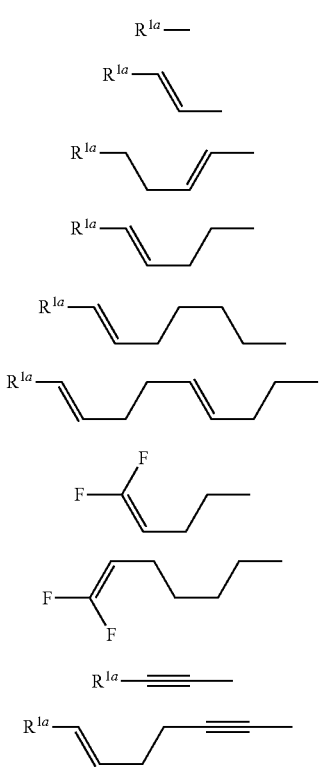

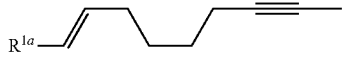

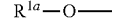

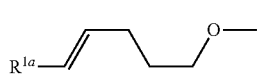

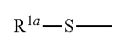

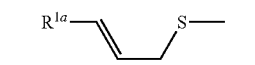

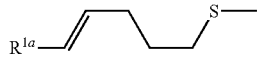

In formula (1), Z$^1$, Z$^2$, Z$^3$, Z$^4$ and Z$^5$ are independently a single bond or —CF$_2$O—, but are not all single bonds.

In formula (1), L$^1$, L$^2$, L$^3$, L$^4$ and L$^5$ are independently hydrogen or fluorine.

In Formula (1), X$^1$ is hydrogen, halogen, —C≡N, —N=C=S, —C≡C—C≡N, —SF$_5$, or C$_{1-10}$ alkyl in which arbitrary —CH$_2$— may be substituted with —O—, —S—, —CH=CH— or —C≡C— and arbitrary hydrogen may be substituted with halogen.

Specific examples of alkyl in which arbitrary hydrogen is substituted with halogen are —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F and —(CF$_2$)$_5$—F.

Specific examples of alkoxy in which arbitrary hydrogen is substituted with halogen are —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F and —O—(CF$_2$)$_5$—F.

Specific examples of alkenyl in which arbitrary hydrogen is substituted with halogen are —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$ and —CH=CHCF$_2$CF$_3$.

Specific examples of X$^1$ are hydrogen, fluorine, chlorine, —C≡N, —N=C=S, —SF$_5$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —OCH$_3$, —OC$_2$H$_5$, —OC$_3$H$_7$, —OC$_4$H$_9$, —OC$_5$H$_{11}$, —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$, —(CH$_2$)$_3$—CH=CH$_2$, —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$ and —CH=CHCF$_2$CF$_3$.

Preferred examples of $X^1$ are fluorine, chlorine, —C≡N, —$CF_3$, —$CHF_2$, —$CH_2F$, —$OCF_3$, —$OCHF_2$ and —$OCH_2F$. More preferred examples are fluorine, chlorine and —$CF_3$.

In formula (1), m is 0, 1 or 2, n and o are independently 0 or 1, and $1 \leq m+n+o \leq 2$.

1-2. Properties of Compound (1)

Compound (1) used in this invention is further described in detail. Compound (1) is a liquid crystal compound having a chlorobenzene ring, which has very stable physical and chemical properties under the conditions where the device is generally used, has good compatibility with other liquid crystal compounds and is difficult to exhibit smectic phase. The composition containing such a compound is stable under the conditions where the device is generally used. Therefore, the composition has a larger temperature range of the optically isotropic liquid crystal phase, and thus can be used in a display device in a wide temperature range. Moreover, due to large dielectric anisotropy and optical anisotropy, the compound can be used as a component for lowering the driving voltage in a composition driven in an optically isotropic liquid crystal phase.

By properly selecting the combination of m, n and o, the left terminal group $R^1$, $L^1$-$L^3$, the most right substituents on the benzene ring and substitution positions thereof ($L^4$, $L^5$ and $X^1$) of the compound (1), the physical properties like clear point, optical anisotropy and dielectric anisotropy can be adjusted at will. The effects of the combination of m, n, and o, the left terminal group $R^1$, the right terminal group $X^1$, the linking groups $Z^1$-$Z^5$ and $L^1$-$L^5$ to the physical properties of the compound (1) will be described below.

Generally, when m+n+o is 2, the clear point of the compounds is high, and when m+n+o is 1, the melting point of the compounds is low.

When $R^1$ is linear, compound (1) has a wide temperature range of liquid crystal phase and a low viscosity. When $R^1$ is branched, the compound (1) is well compatible with other liquid crystal compounds. The compound in which $R^1$ is an optically active group can be used as a chiral dopant. The compound in which $R^1$ is not an optically active group can be used as a component of the composition. When $R^1$ is alkenyl, the preferred stereo-configuration depends on the position of the double bond. An alkenyl compound having a preferred stereo-configuration has a high upper-limit temperature or a wide temperature range of liquid crystal phase.

When the linking groups $Z^1$-$Z^5$ are a single bond or —$CF_2O$—, compound (1) has relatively stable chemical properties and thus being more unlikely to be deteriorated. Further, when the linking group is a single bond, the compound (1) has a low viscosity. When the linking group is —$CF_2O$—, the compound (1) has a large dielectric anisotropy.

When the right terminal group $X^1$ is fluorine, chlorine, —C≡N, —N=C=S, —$SF_5$, —$CF_3$, —$CHF_2$, —$CH_2F$, —$OCF_3$, —$OCHF_2$ or —$OCH_2F$, the compound (1) has a large dielectric anisotropy. When $X^1$ is —C≡N, —N=C=S or alkenyl, the compound (1) has a large optical anisotropy. When $X^1$ is fluorine, —$OCF_3$ or alkyl, the compound (1) has stable chemical properties.

When $L^4$ are $L^5$ are fluorine and $X^1$ is fluorine, chlorine, —C≡N, —N=C=S, —$SF_5$, —$CF_3$, —$CHF_2$, —$CH_2F$, —$OCF_3$, —$OCHF_2$ or —$OCH_2F$, the compound (1) has a large dielectric anisotropy. When $L^4$ is fluorine and $X^1$ is —$CF_3$ or —$OCF_3$, $L^4$ and $L^5$ are fluorine and $X^1$ is —$CF_3$ or —$OCF_3$, or $L^1$, $L^2$ and $X^1$ are fluorine, the compound (1) has a large dielectric anisotropy, a wide temperature range of liquid crystal phase and stable chemical properties, and thus being unlikely to be deteriorated.

Generally, the more fluorine in $L^1$-$L^3$ is, the larger the dielectric anisotropy is.

As described above, a compound with target properties can be obtained by properly selecting the species of the terminal groups and the linking groups, etc.

1-3. Specific Examples of Compound (1)

Preferred examples of compound (1) are formulae (1-1A)-(1-1I) and (1-2A)-(1-2D). More preferred examples are (1-1B), (1-1C), (1-1E), (1-1F) and (1-2A)-(1-2C).

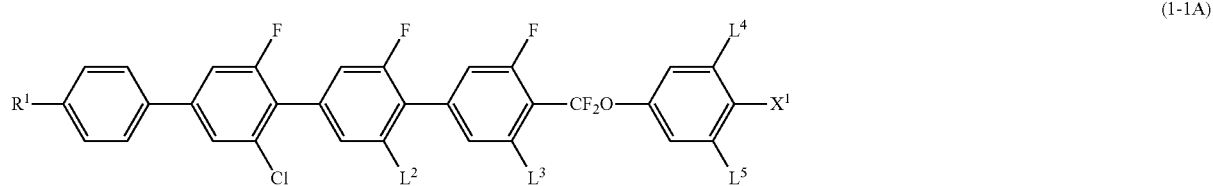

(1-1A)

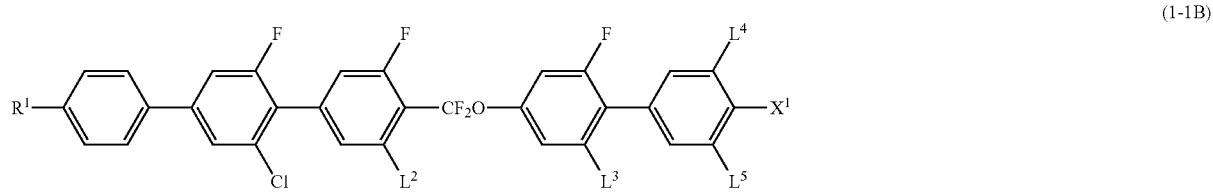

(1-1B)

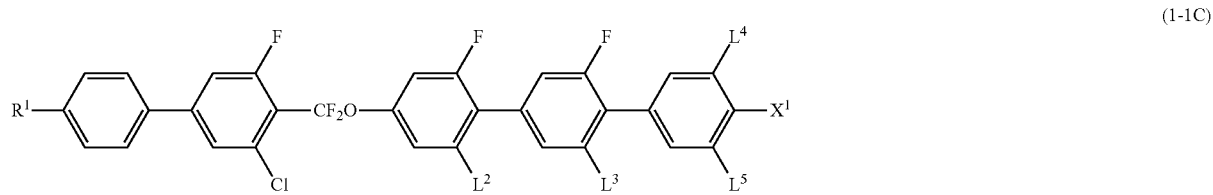

(1-1C)

-continued
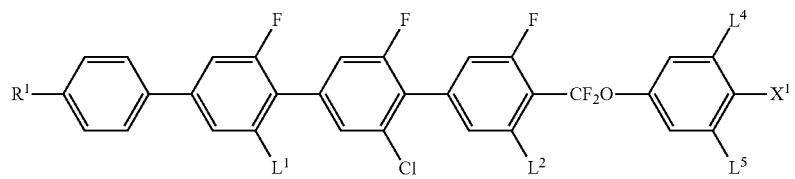
(1-1D)
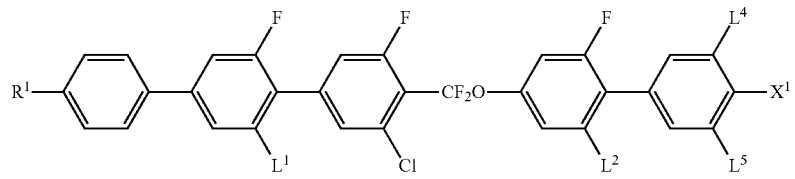
(1-1E)
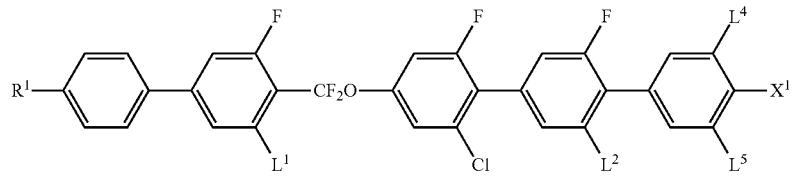
(1-1F)
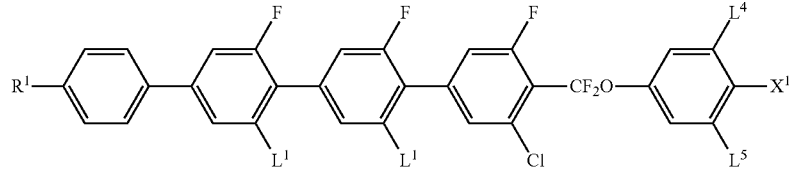
(1-1G)
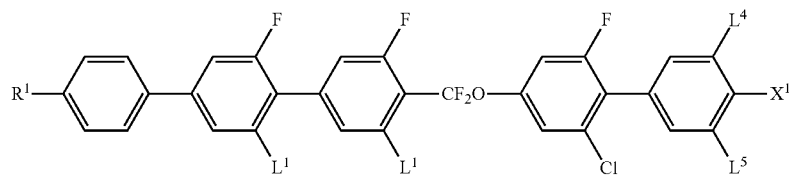
(1-1H)
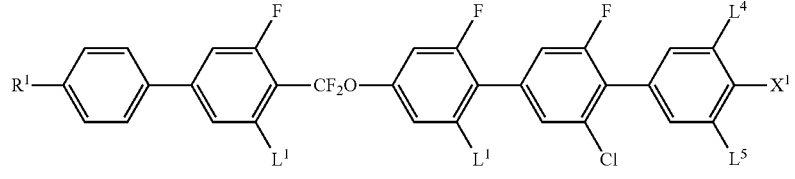
(1-1I)
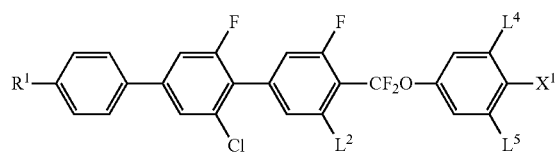
(1-2A)
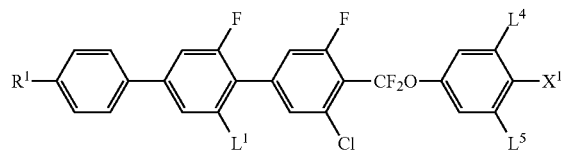
(1-2C)
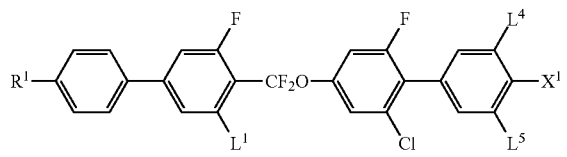
(1-2B)
(1-2D)

In these formulae, $R^1$ is a chain selected from formulae (CHN-1) to (CHN-4) and (CHN-6) to (CHN-8) shown above, and $X^1$ is fluorine, chlorine, —C≡N, —$CF_3$, —$CHF_2$, —$CH_2F$, —$OCF_3$, —$OCHF_2$ or —C≡C—$CF_3$.
More specific examples are compounds of formulae (1-1B-1) to (1-1B-6), (1-1C-1) to (1-1C-6), (1-1E-1) to (1-1E-6), (1-1F-1) to (1-1F-6), (1-1H-1) to (1-1H-4), (1-1I-1) to (1-1I-4), (1-2A-1) to (1-2A-6), (1-2B-1) to (1-2B-6) and (1-2C-1) to (1-2C-6) shown below, and the compounds of formulae (S1-9), (S2-2), (S3-4) and (S10-1) mentioned in Examples 1-4.
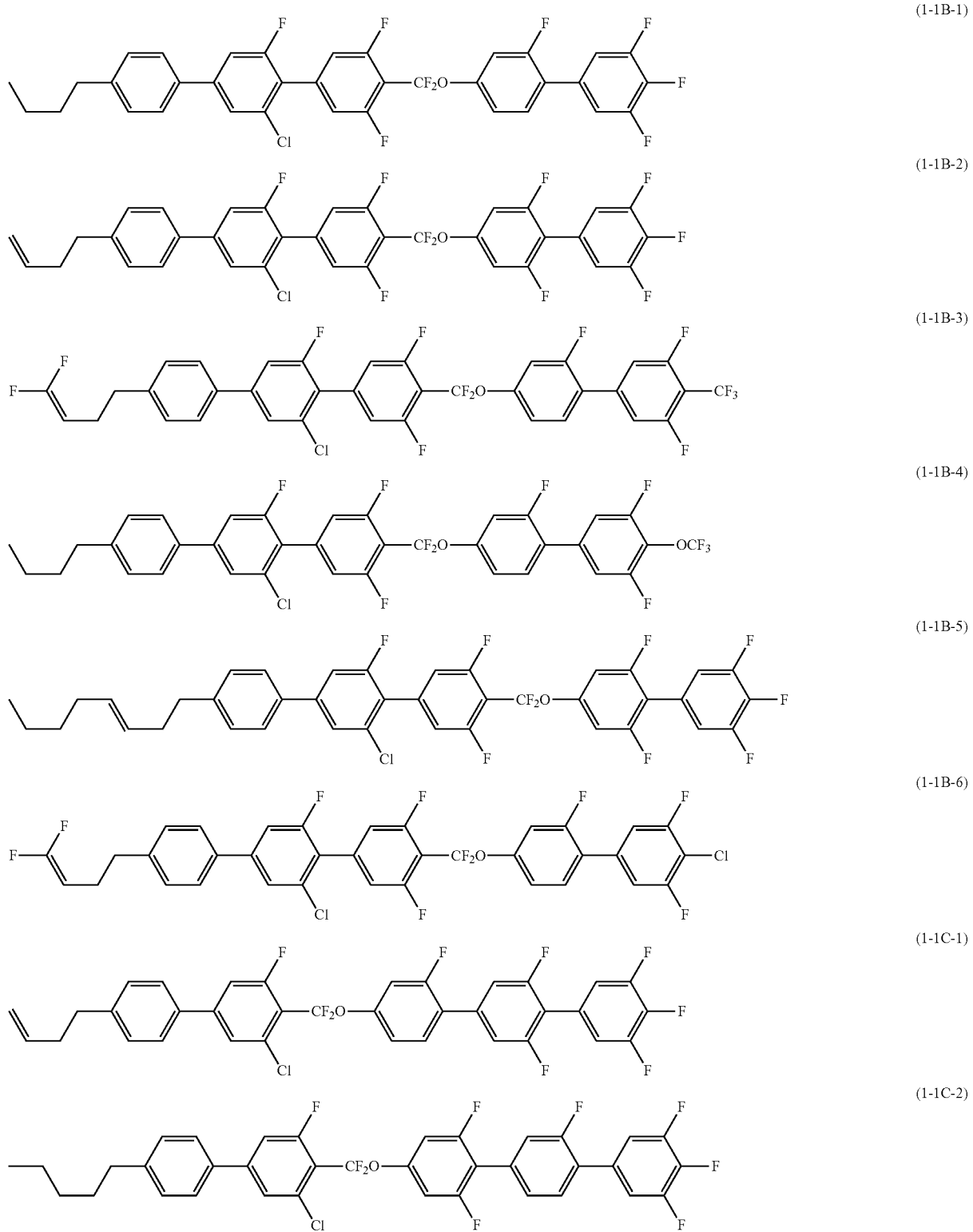

-continued
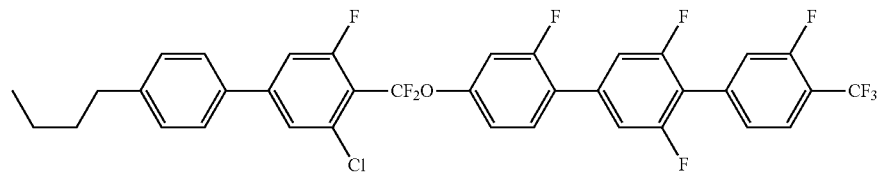 (1-1C-3)
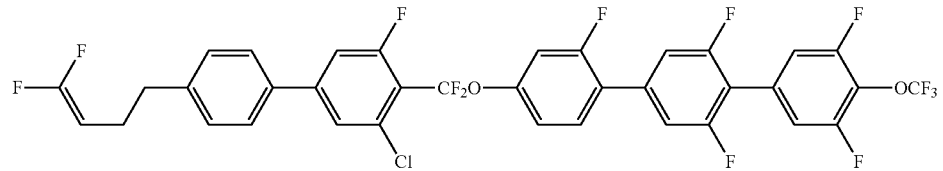 (1-1C-4)
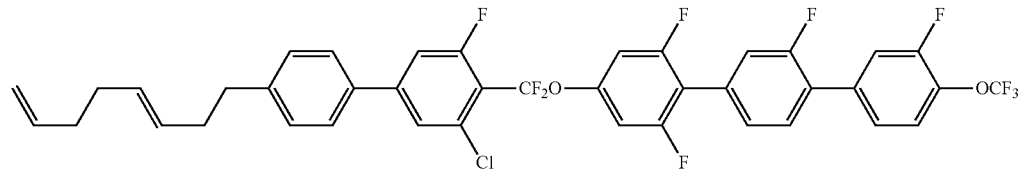 (1-1C-5)
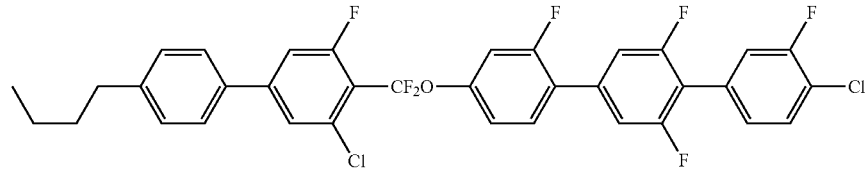 (1-1C-6)
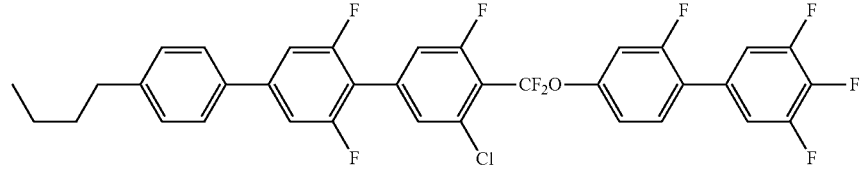 (1-1E-1)
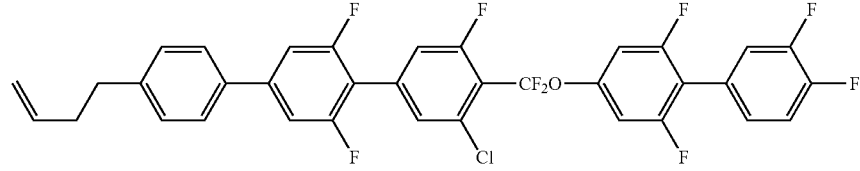 (1-1E-2)
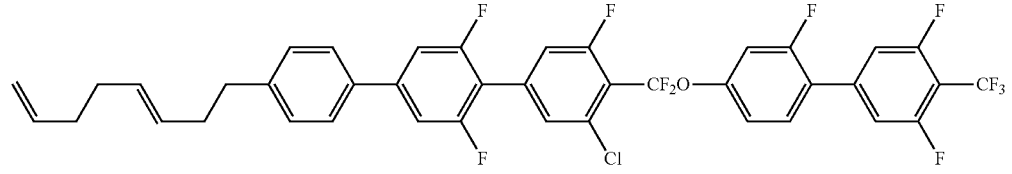 (1-1E-3)
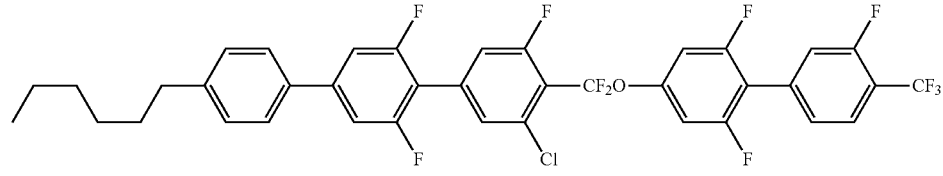 (1-1E-4)
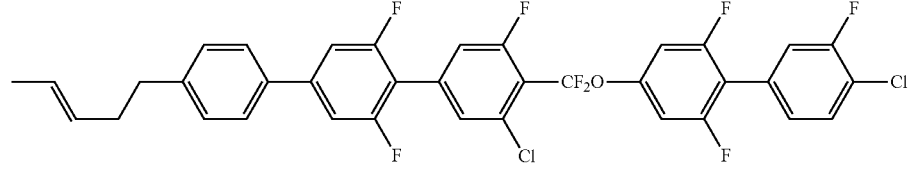 (1-1E-5)

-continued
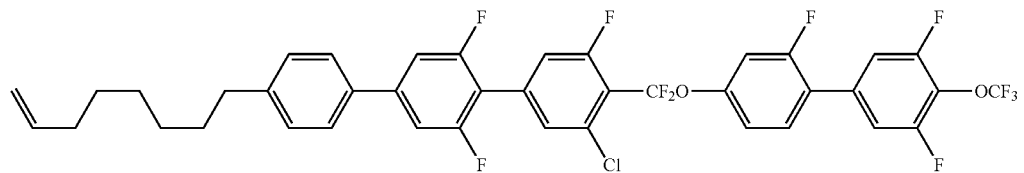 (1-1E-6)
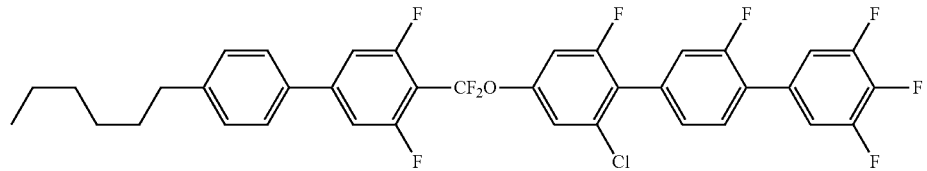 (1-1F-1)
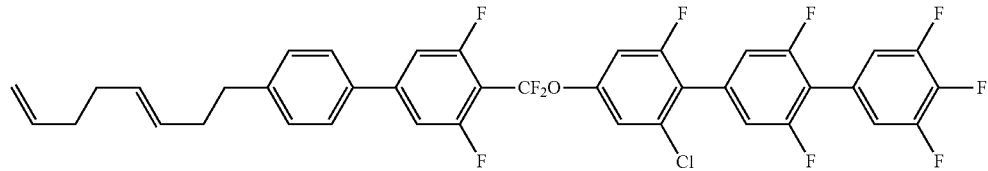 (1-1F-2)
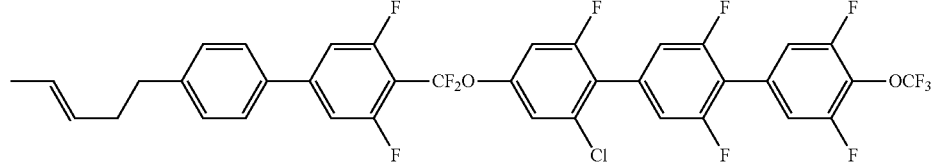 (1-1F-3)
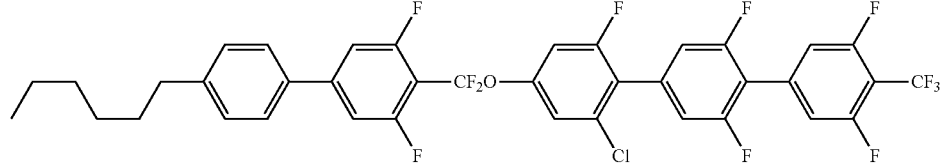 (1-1F-4)
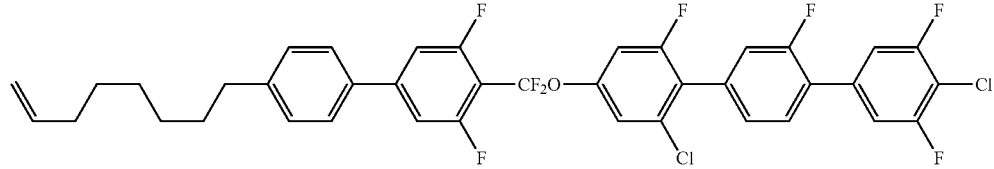 (1-1F-5)
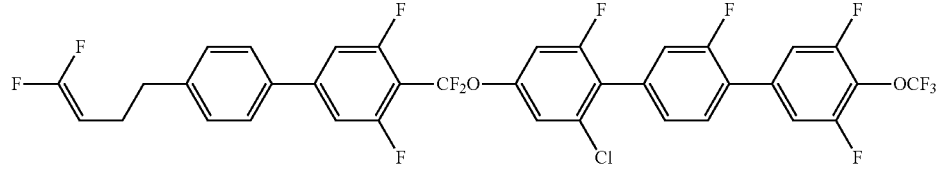 (1-1F-6)
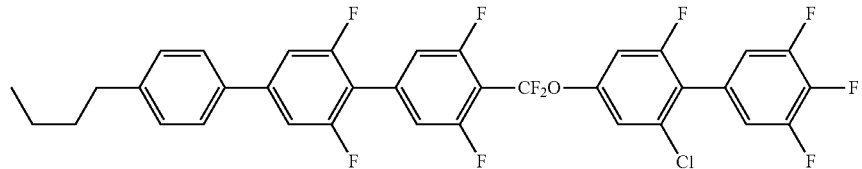 (1-1H-1)
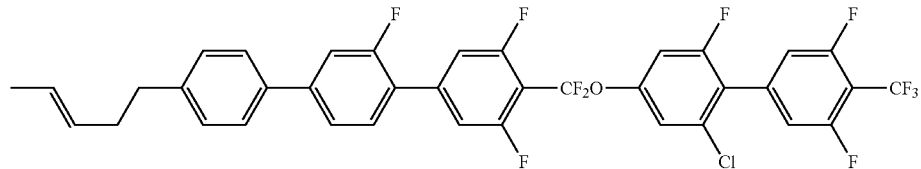 (1-1H-2)

-continued
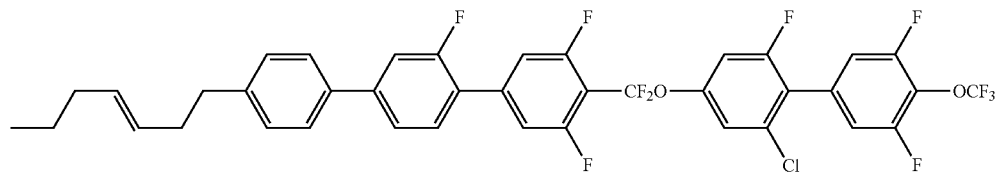 (1-1H-3)
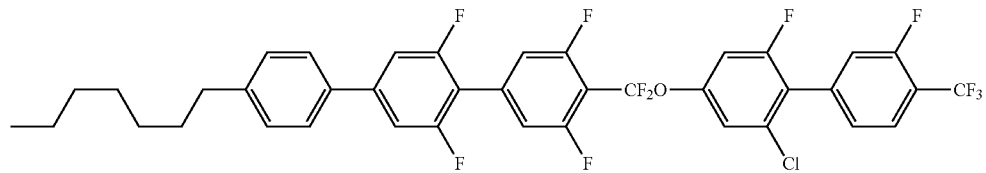 (1-1H-4)
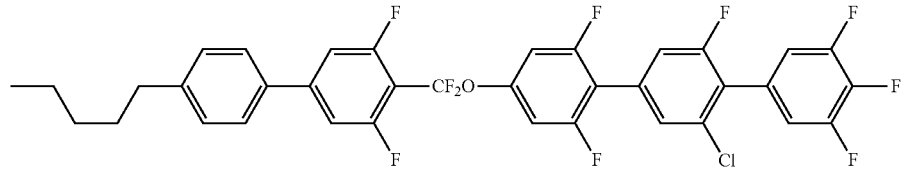 (1-1I-1)
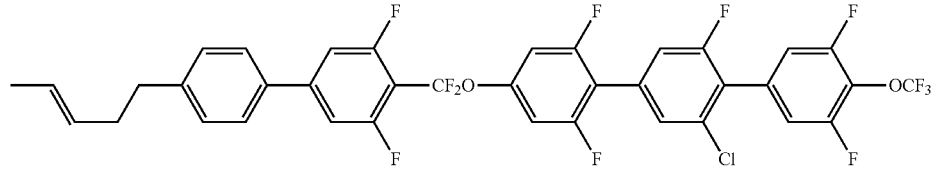 (1-1I-2)
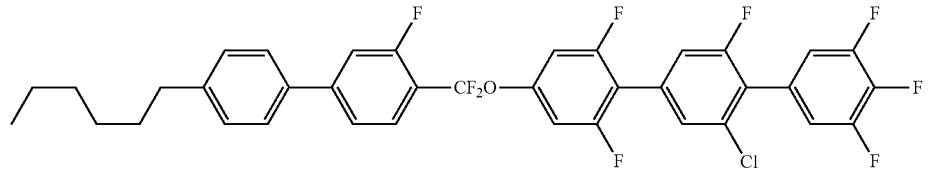 (1-1I-3)
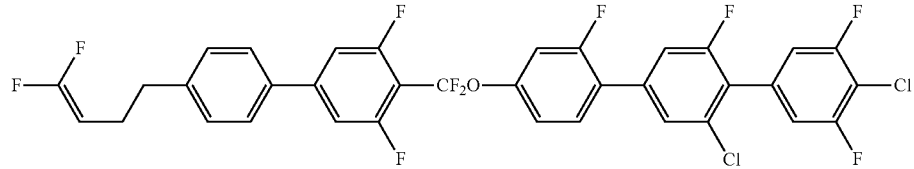 (1-1I-4)
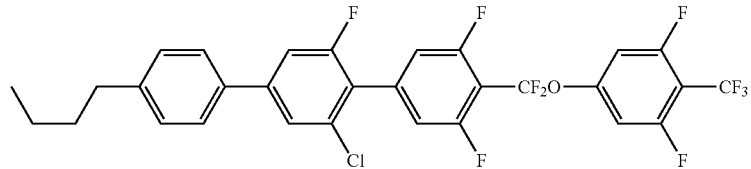 (1-2A-1)
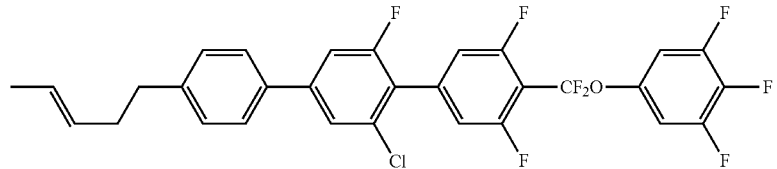 (1-2A-2)
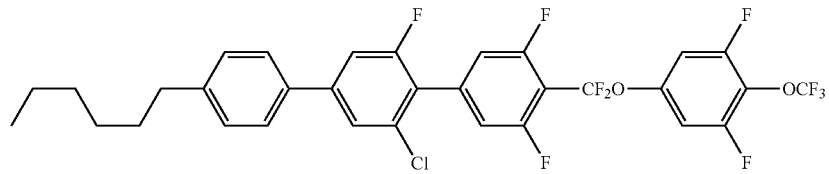 (1-2A-3)

(1-2A-4)
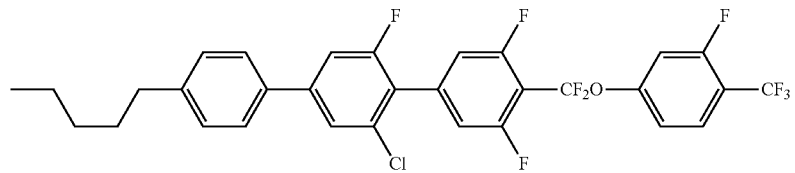
(1-2A-5)
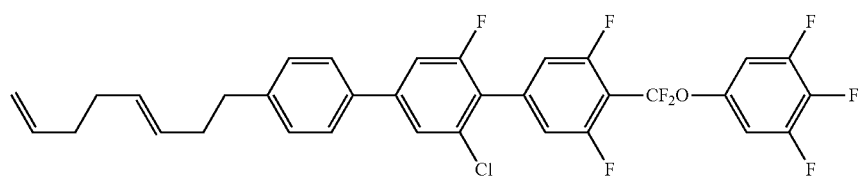
(1-2A-6)
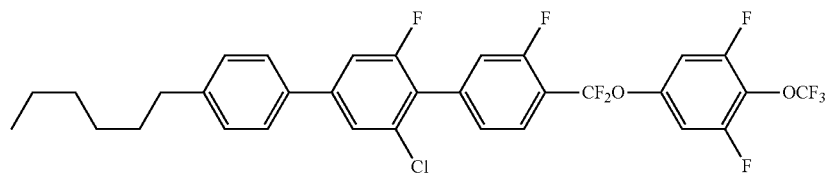
(1-2B-1)
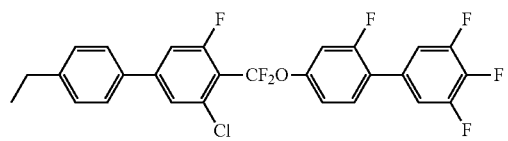
(1-2B-2)
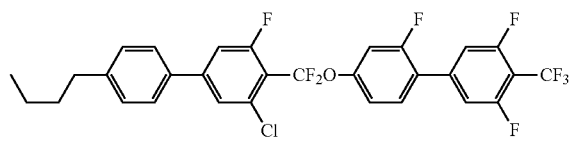
(1-2B-3)
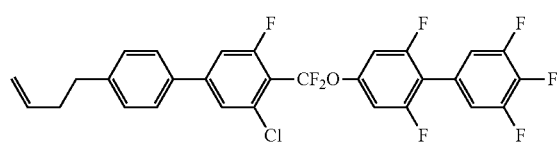
(1-2B-4)
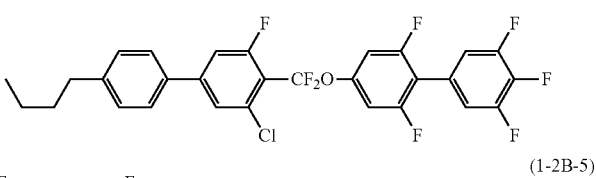
(1-2B-5)
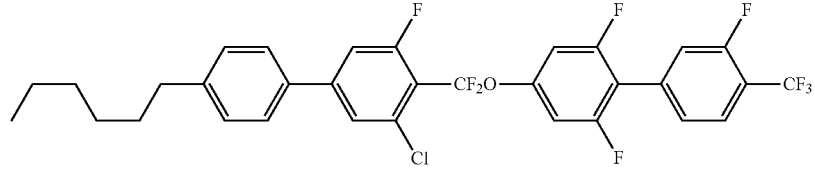
(1-2B-6)
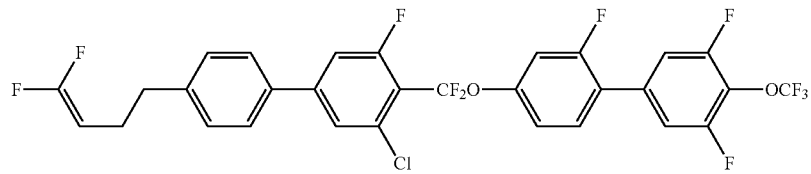
(1-2C-1)
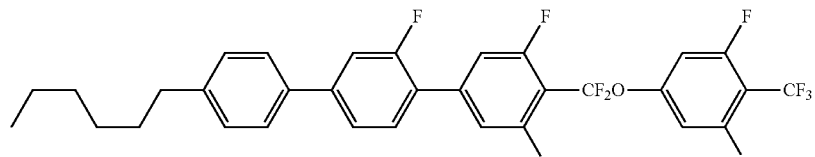
(1-2C-2)
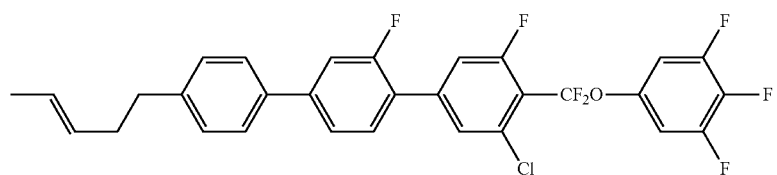

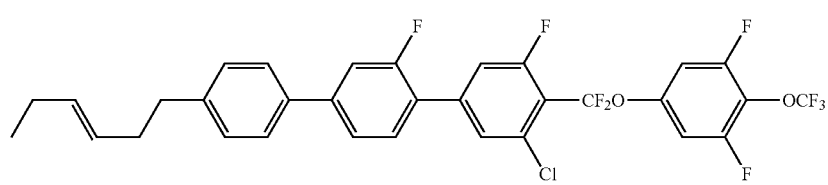

(1-2C-3)

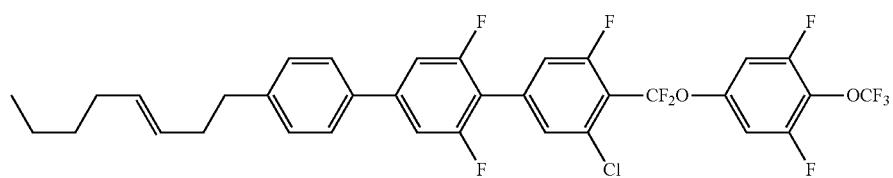

(1-2C-4)

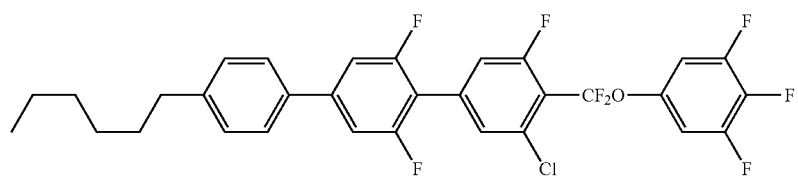

(1-2C-5)

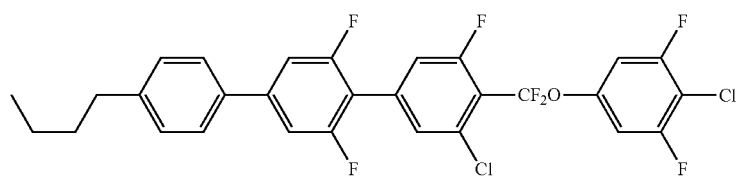

(1-2C-6)

1-4. Synthesis of Compound (1)

Synthesis of the compound (1) is described next; it can be synthesized by a suitable combination of organic synthesis methods. The methods for introducing the target terminal groups, rings and linking groups to the starting compound are described in, for example, *Organic Syntheses* (John Wiley & Sons, Inc.), *Organic Reactions* (John Wiley & Sons, Inc.), *Comprehensive Organic Synthesis* (Pergamon Press) and *New Lecture on Experimental Chemistry* (Maruzen).

1-4-1. Chlorobenzene Ring

Chlorobenzene compounds such as 1-bromo-3-chloro-5-fluorobenzene and 3-chloro-5-fluorophenol are commercially available as reagents.

1-4-2. Formation of Bonding Groups $Z^1$-$Z^5$

An exemplary method for forming the linking groups $Z^1$-$Z^5$ in compound (1) is shown by the scheme below. In this scheme, $MSG^1$ or $MSG^2$ is a monovalent organic group having at least one ring. The multiple $MSG^1$ (or $MSG^2$) used in the scheme can be identical or different. Compounds (1A)-(1J) are equivalent to compound (1).

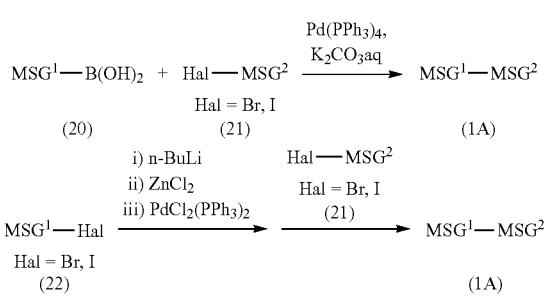

Next, the methods for forming various bonds of the linking groups $Z^1$-$Z^6$ compound (1) are described in Items (I)-(II) below.

(I) Formation of Single Bond

Arylboric acid (20) is reacted with the compound (21) synthesized by a known method, in the presence of an aqueous carbonate solution and a catalyst such as tetrakis-(triphenylphosphine)palladium, to synthesize the compound (1A).

The compound (1A) can alternatively be synthesized by reacting the compound (22) synthesized by a known method with n-butyl lithium, with zinc chloride, and then with the compound (21) in the presence of a catalyst such as bis (triphenylphosphine)palladium dichloride.

(II) Formation of —CF$_2$O—

The compound (22) is reacted with n-butyl lithium and then with carbon dioxide to produce the carboxylic acid (23). Next, the compound (23) and a phenol compound (25) synthesized by a known method are subjected to dehydration in the presence of DCC (1,3-dicyclohexylcarbodiimide) and DMAP (4-dimethylaminopyridine) to synthesize the compound (24) having —COO—. A compound having —OCO— can also be synthesized by this method. The compound (24) is treated with a vulcanizing agent such as Lawesson's reagent to produce the compound (26). Then the compound (26) is fluorinated with hydrogen fluoride pyridine complex and NBS (N-bromosuccinimide), to synthesize the compound (1B) having —CF$_2$O— (see M. Kuroboshi et al., *Chem. Lett.*, 1992, 827). The compound (1B) can alternatively be synthesized by fluorinating compound (26) with (diethylamino) sulfur trifluoride (DAST) (see W. H. Bunnelle et al., *J. Org. Chem.* 1990, 55, 768). A compound having —OCF$_2$— can also be synthesized by this method. The linking groups can alternatively be synthesized by the process described in Peer. Kirsch et al., *Angew. Chem. Int. Ed.* 2001, 40, 1480.

1-4-4. Synthesis of Compound (1)

There are numerous processes for synthesizing a compound of formula (1), and a compound of formula (1) can be synthesized from commercially available reagents with suitable reference to the Examples in the specification or literatures and books.

2. Compounds (2)-(11)

A second aspect of this invention relates to a liquid crystal composition obtained by adding a component selected from the components B, C, D and E shown below to the compound of formula (1) (i.e. component A). As compared with a composition containing the component A alone, the liquid crystal composition can be adjusted for the driving voltage, temperature range of liquid crystal phase, optical anisotropy, dielectric anisotropy, viscosity and so on.

Preferably, the component to be added to the component A is a mixture obtained by mixing the component B, C, D, E or F. The component B includes at least one compound selected from the group consisting of the compounds of formulae (2), (3) and (4) shown above. The component C includes at least one compound selected from the group consisting of the compounds of formula (5) shown above. The component D includes at least one compound selected from the group consisting of the compounds of formula (6) shown above. The component E includes at least one compound selected from the group consisting of the compounds of formulae (7)-(10) shown above. The component F includes at least one compound selected from the group consisting of the compounds of formula (11) shown above.

Moreover, for each component of the liquid crystal composition used in this invention, an analogue containing isotopes of each element can be used due to the small difference in the physical properties.

For the component B, preferred examples of the compound of formula (2) are formulae (2-1) to (2-16), preferred examples of the compound of formula (3) are formulae (3-1) to (3-112), and preferred examples of the compound of formula (4) are formulae (4-1) to (4-52).

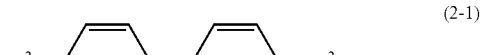
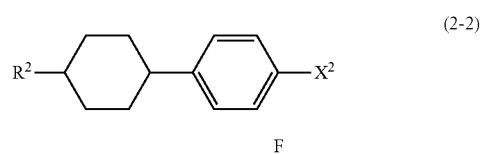
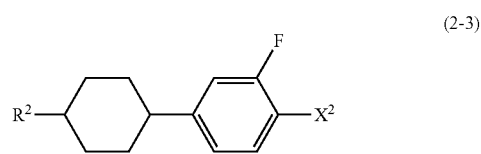
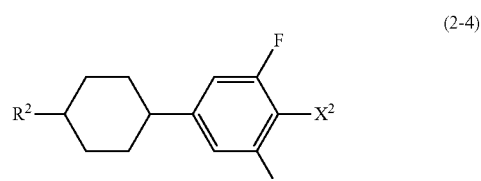
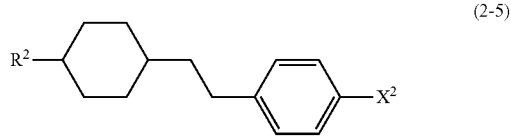
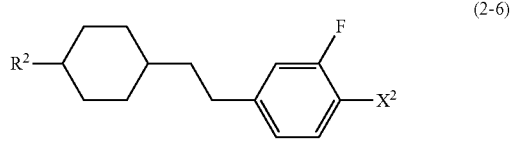
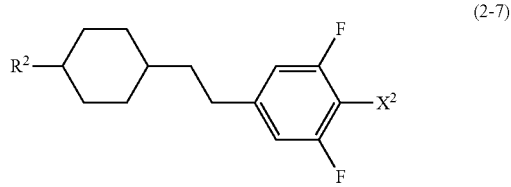
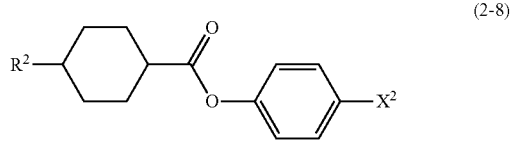
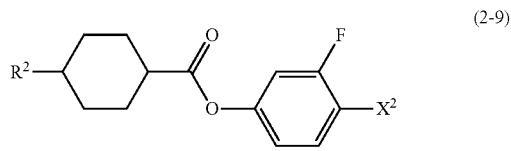
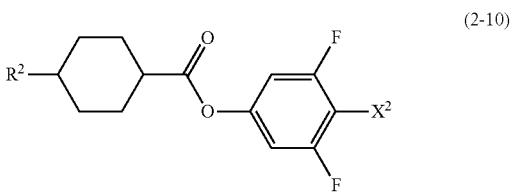

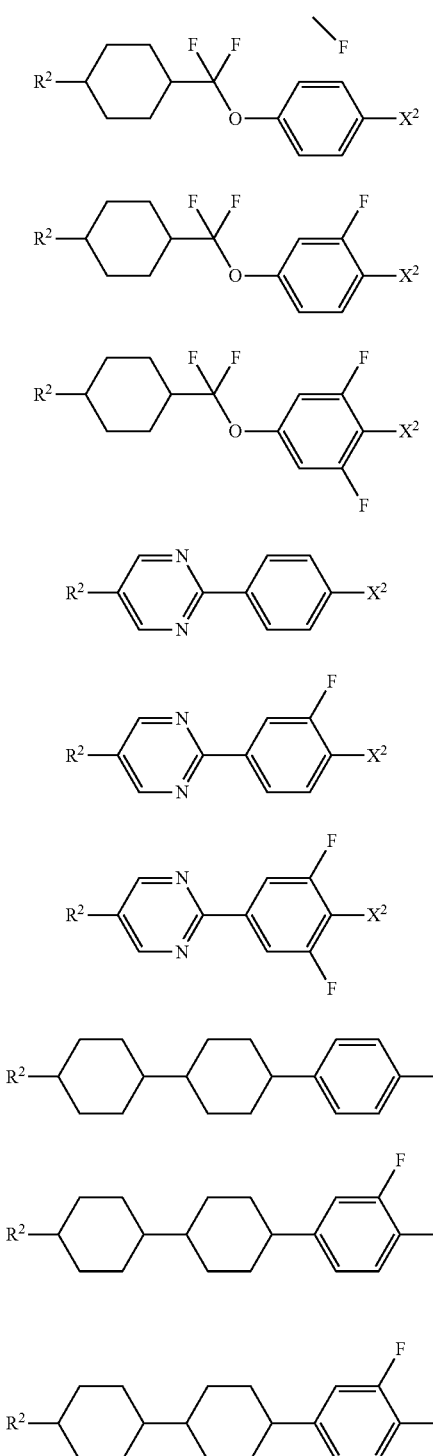
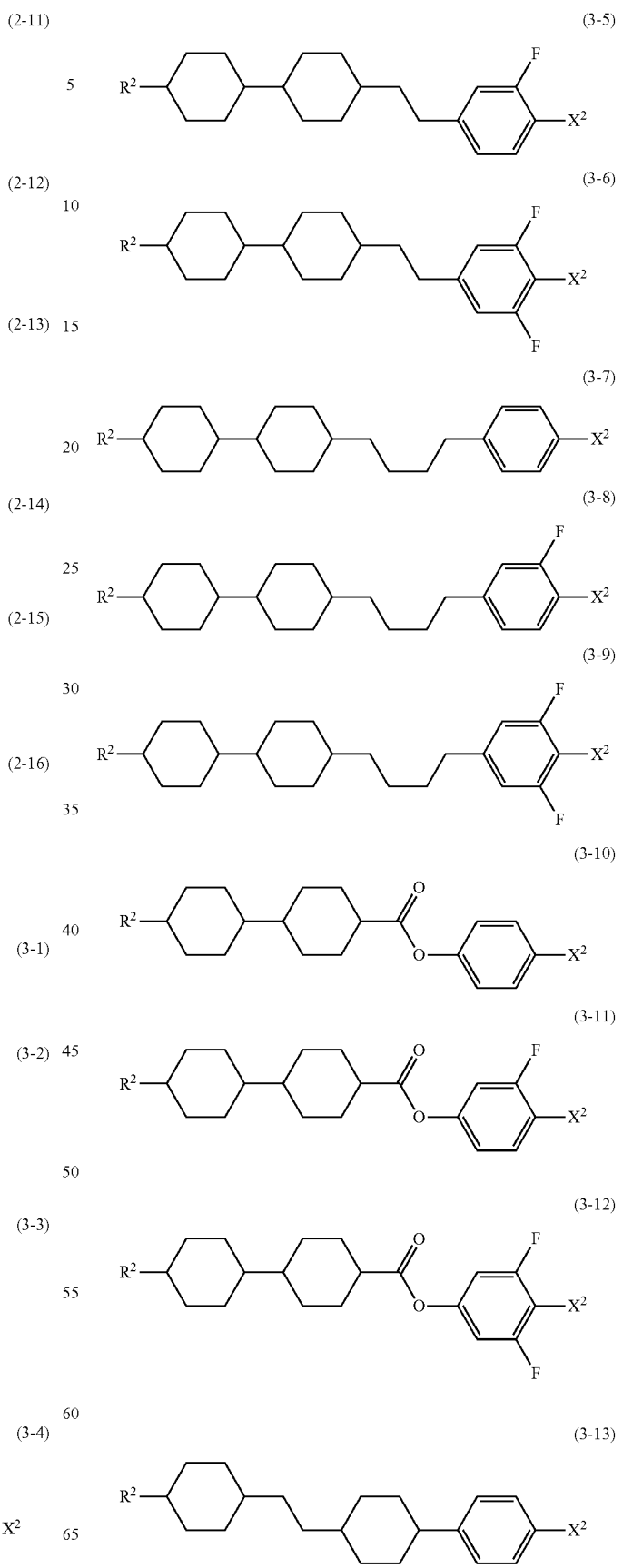

(3-14)
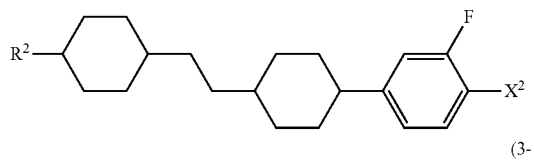
(3-15)
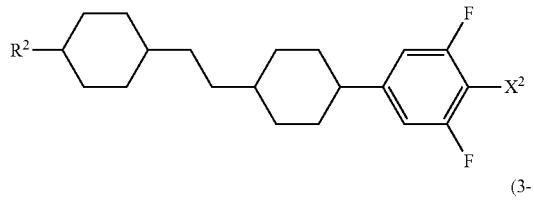
(3-16)
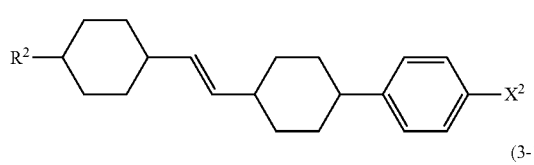
(3-17)
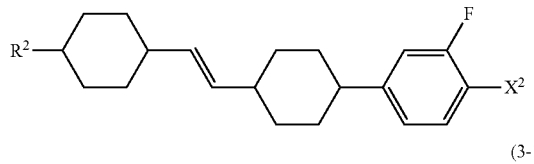
(3-18)
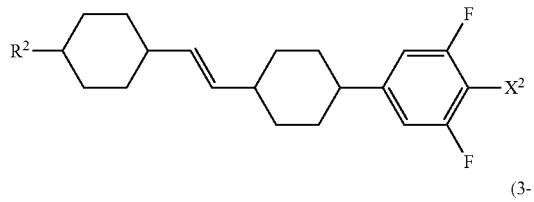
(3-19)
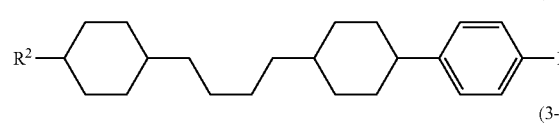
(3-20)
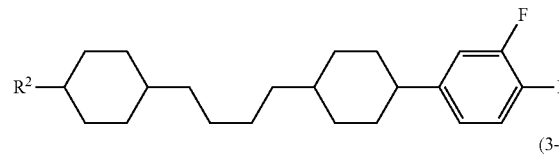
(3-21)
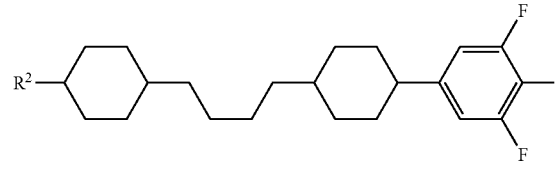
(3-22)
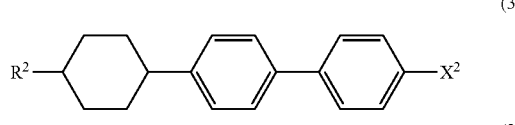
(3-23)
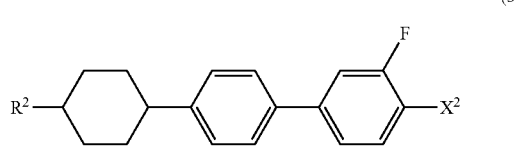
(3-24)
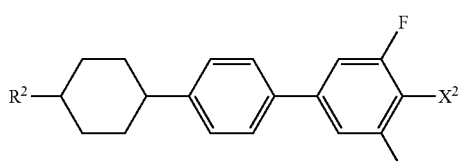
(3-25)
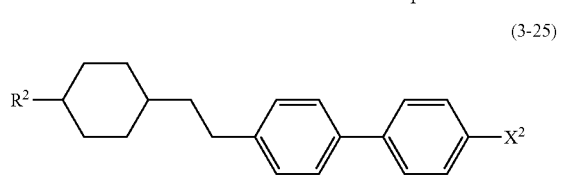
(3-26)
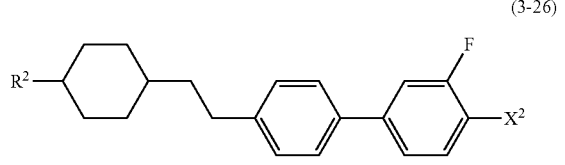
(3-27)
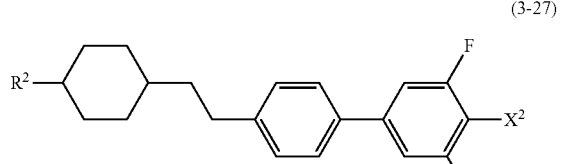
(3-28)
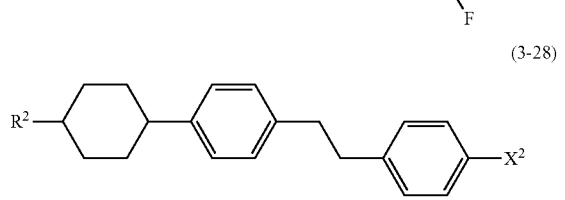
(3-29)
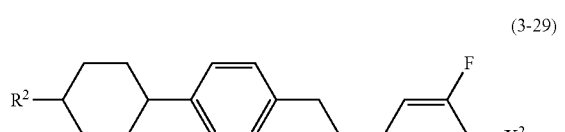
(3-30)
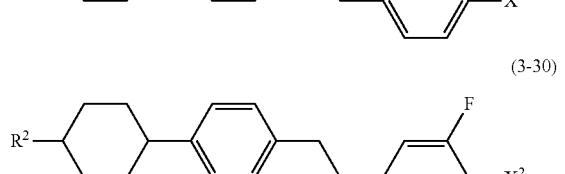
(3-31)
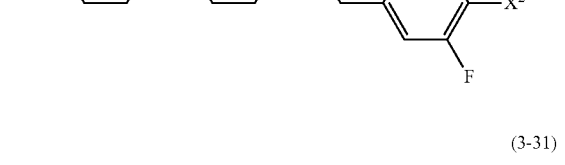
(3-32)
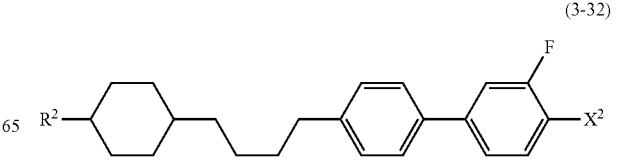

(3-33) 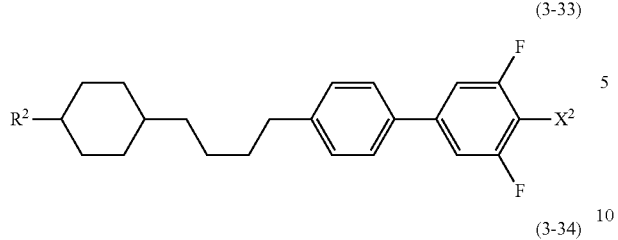
(3-34) 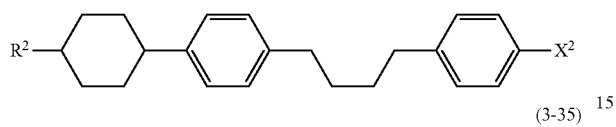
(3-35) 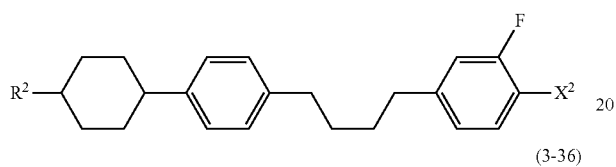
(3-36) 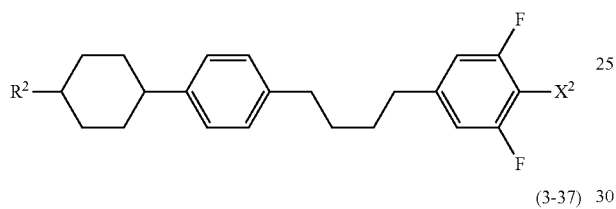
(3-37) 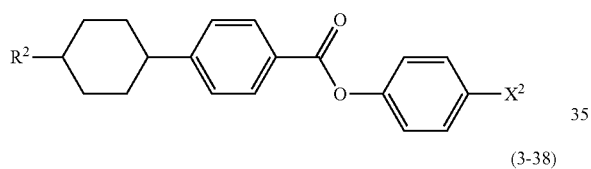
(3-38) 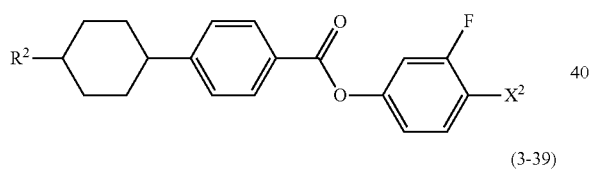
(3-39) 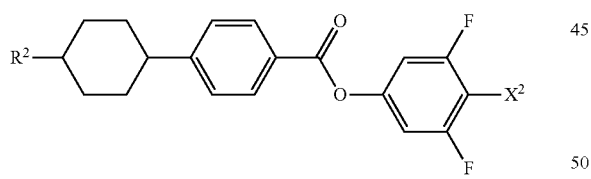
(3-40) 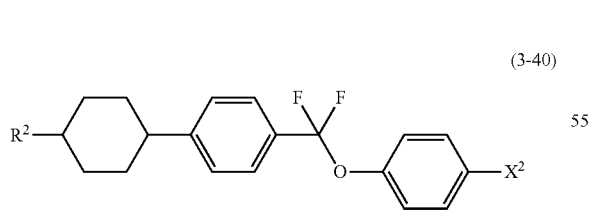
(3-41) 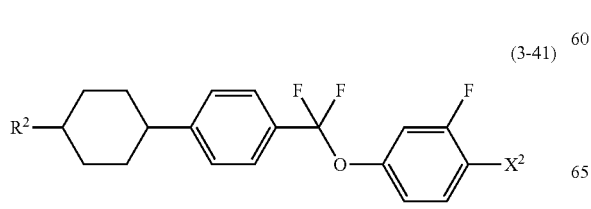
(3-42) 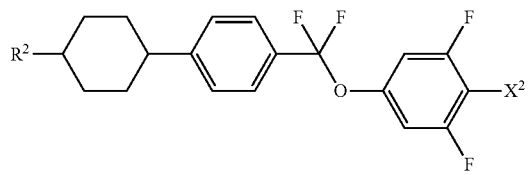
(3-43) 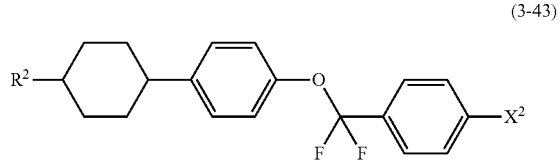
(3-44) 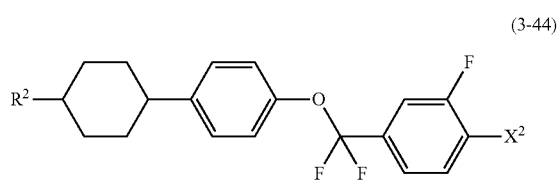
(3-45) 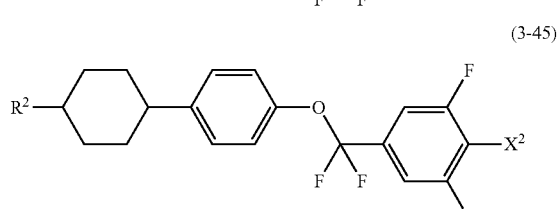
(3-46) 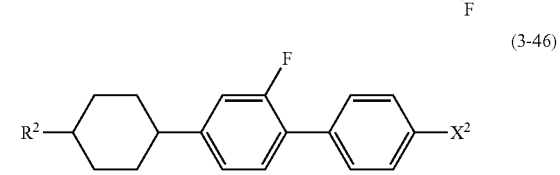
(3-47) 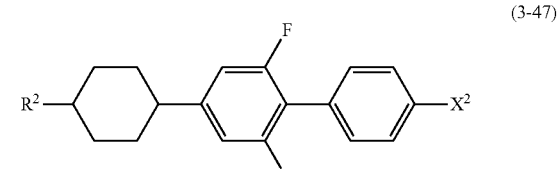
(3-48) 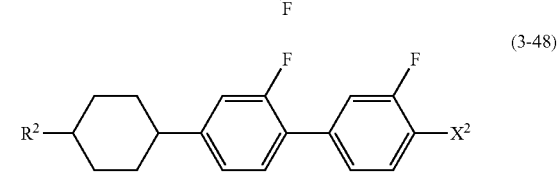
(3-49) 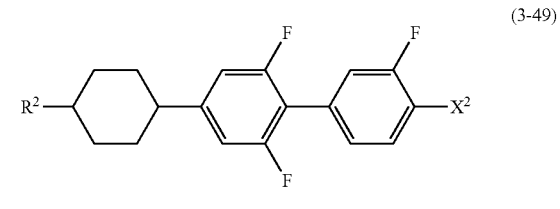
(3-50) 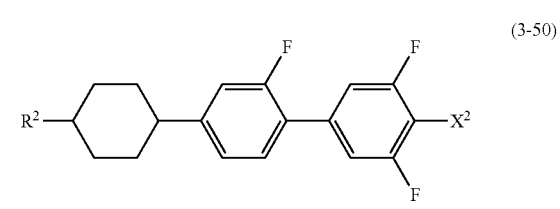

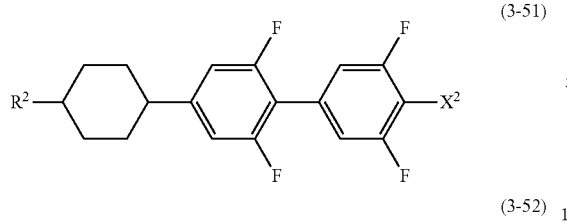 (3-51)
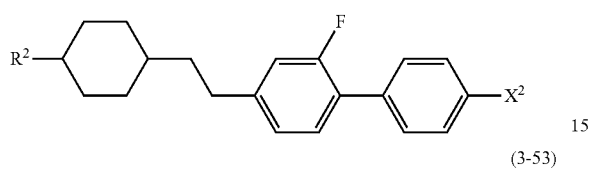 (3-52)
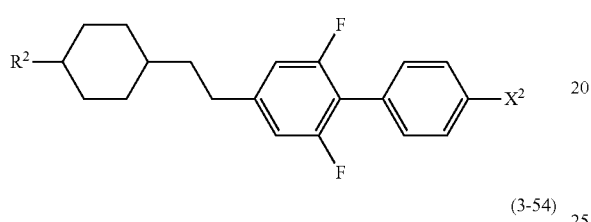 (3-53)
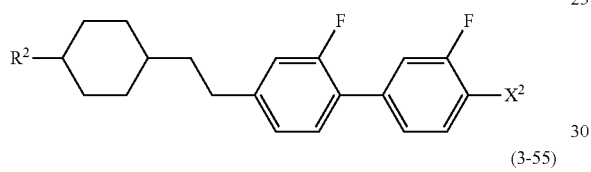 (3-54)
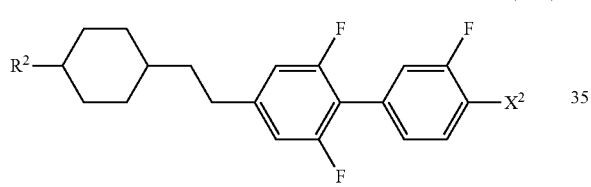 (3-55)
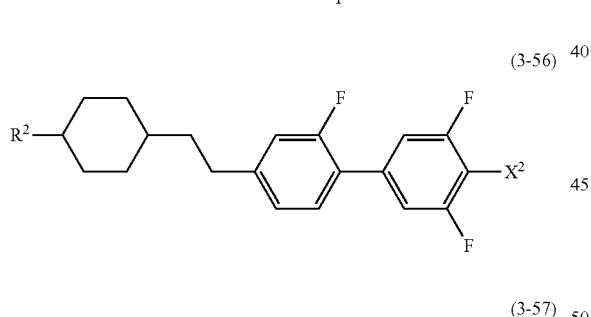 (3-56)
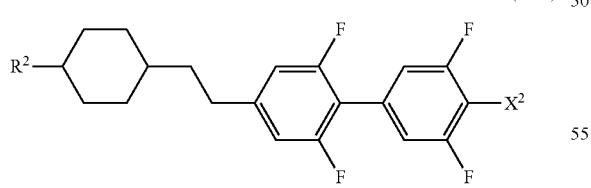 (3-57)
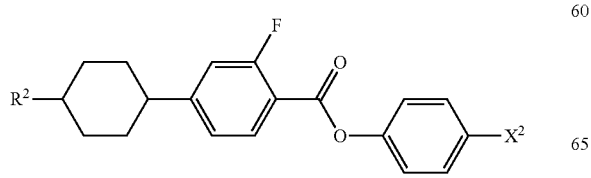 (3-58)
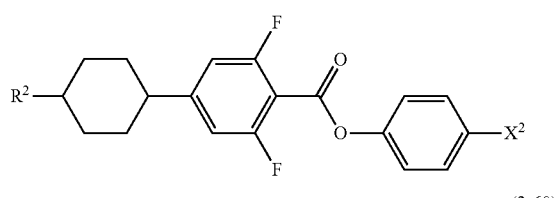 (3-59)
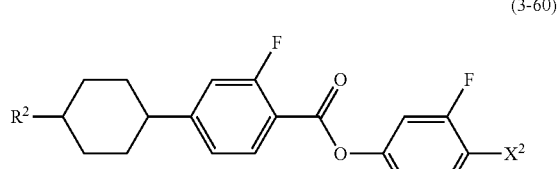 (3-60)
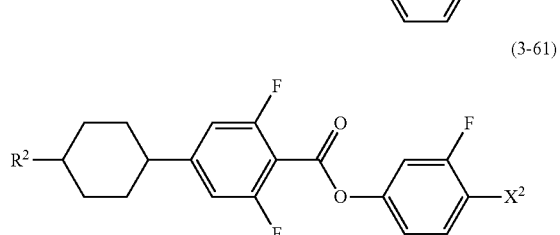 (3-61)
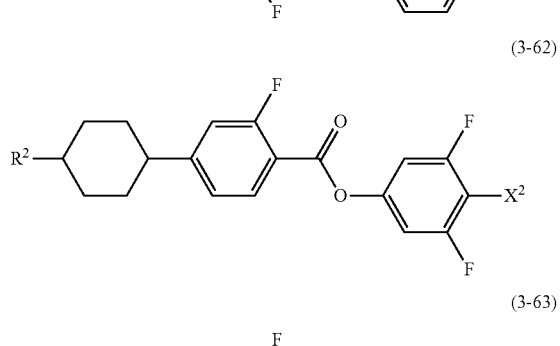 (3-62)
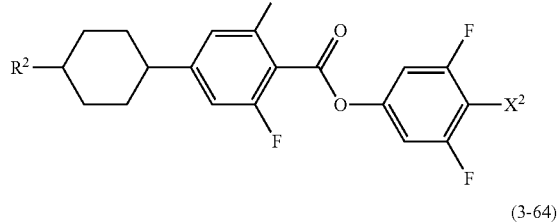 (3-63)
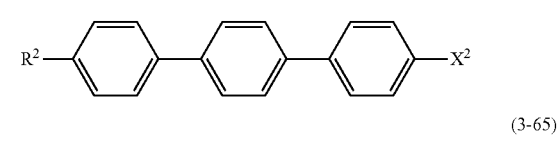 (3-64)
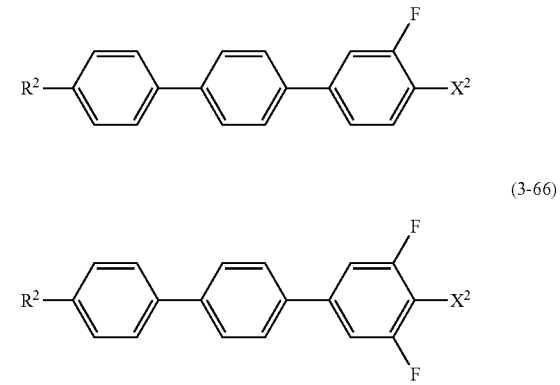 (3-65)
(3-66)

(3-67)
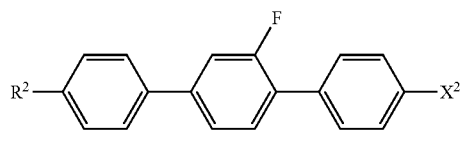
(3-68)
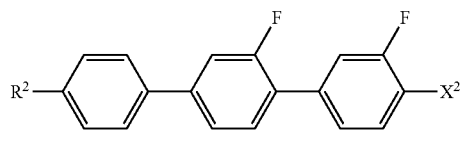
(3-69)
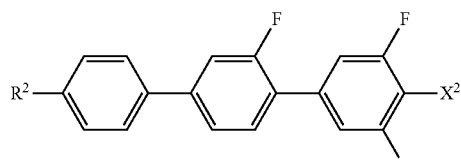
(3-70)
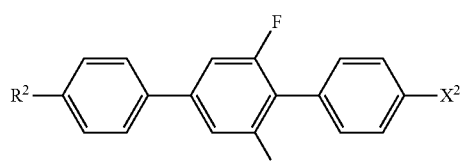
(3-71)
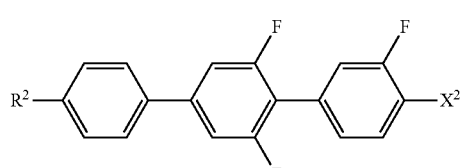
(3-72)
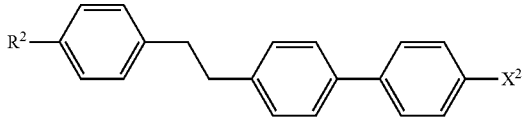
(3-73)
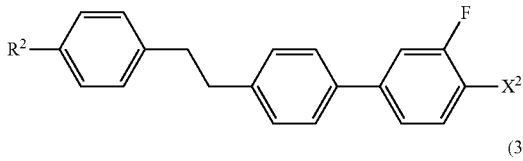
(3-74)
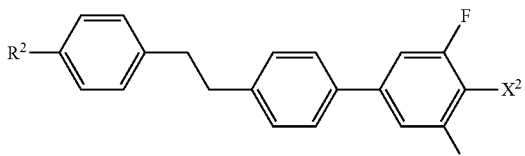
(3-75)
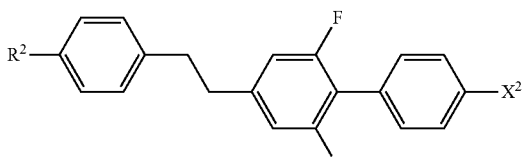
(3-76)
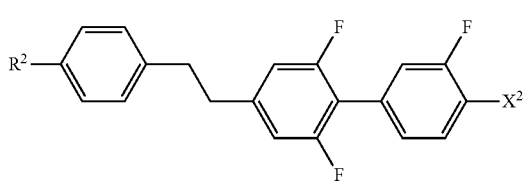
(3-77)
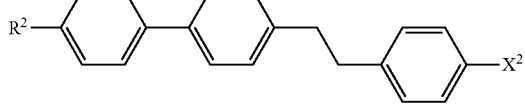
(3-78)
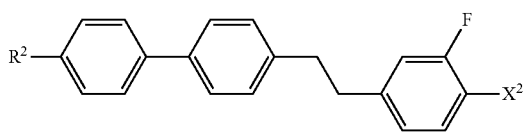
(3-79)
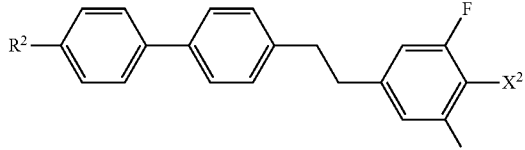
(3-80)
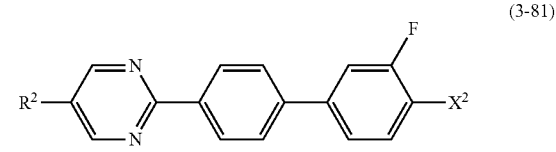
(3-81)
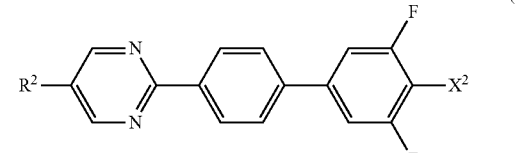
(3-82)
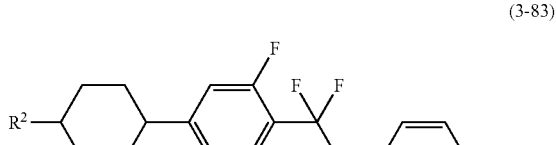
(3-83)
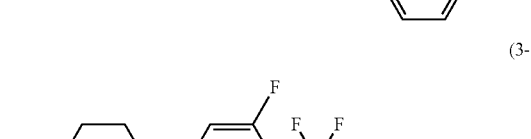
(3-84)
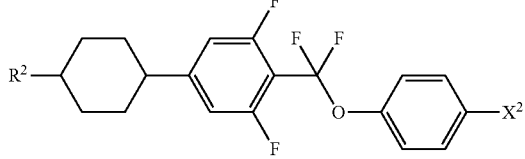

(3-85) 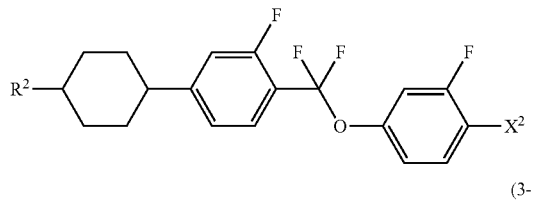
(3-86) 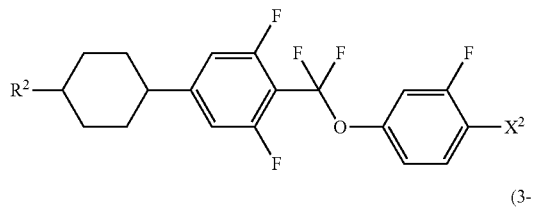
(3-87) 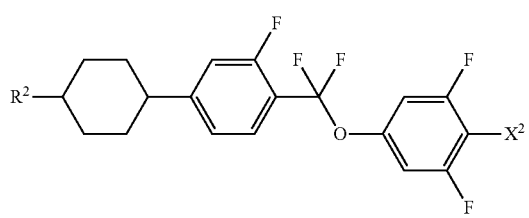
(3-88) 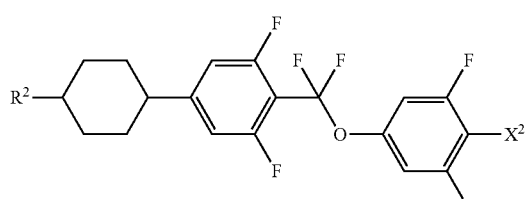
(3-89) 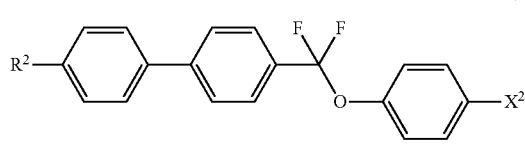
(3-90) 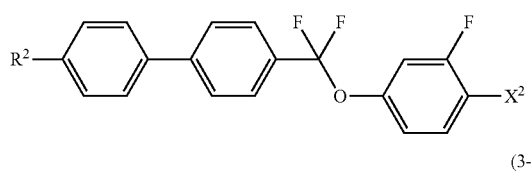
(3-91) 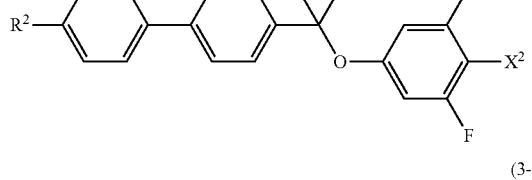
(3-92) 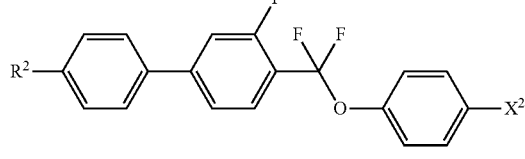
(3-93) 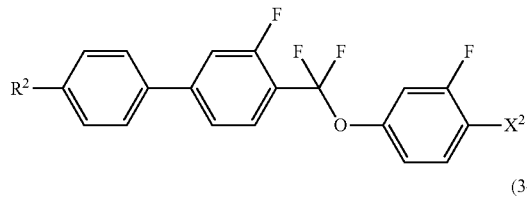
(3-94) 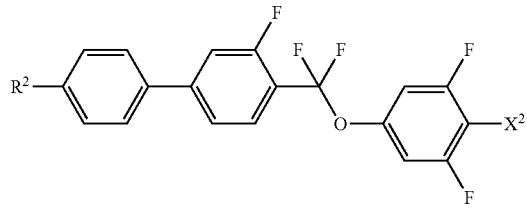
(3-95) 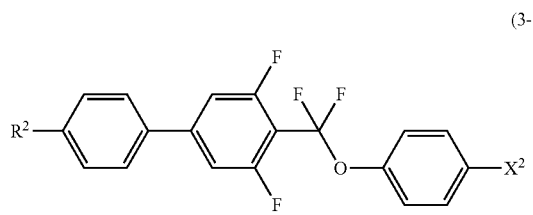
(3-96) 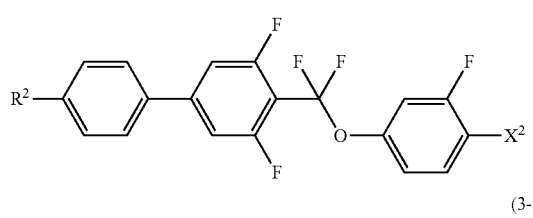
(3-97) 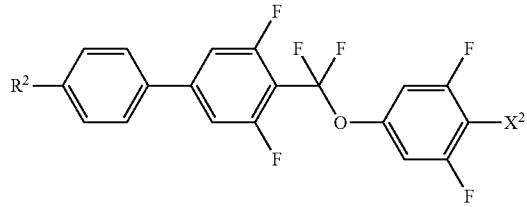
(3-98) 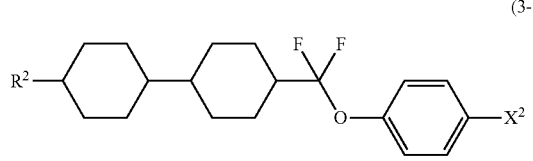
(3-99) 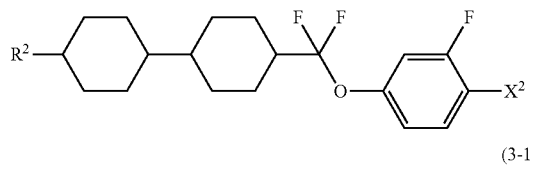
(3-100) 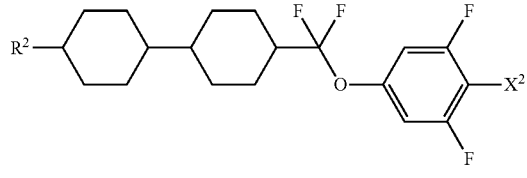

(3-101) 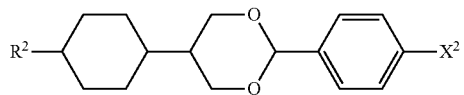
(3-102) 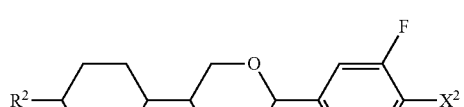
(3-103) 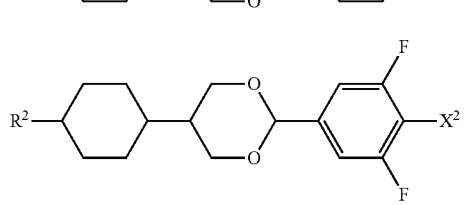
(3-104) 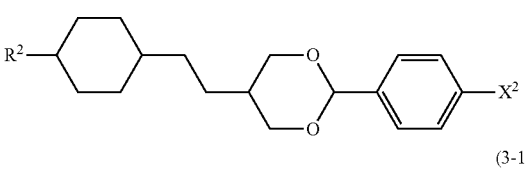
(3-105) 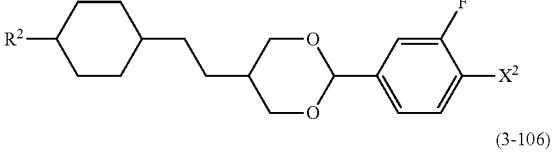
(3-106) 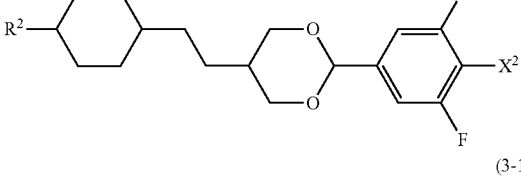
(3-107) 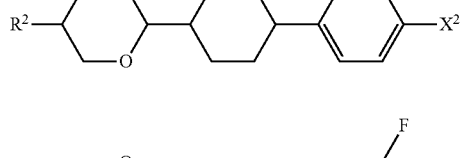
(3-108) 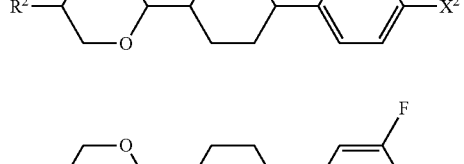
(3-109) 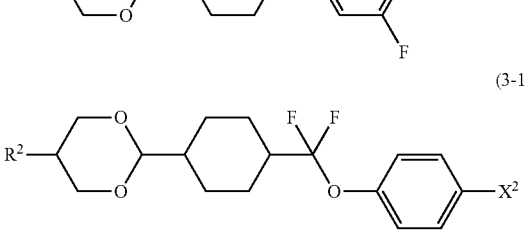
(3-110) 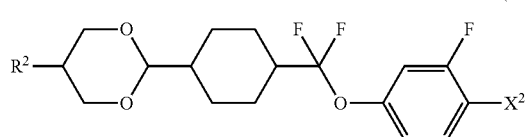
(3-111) 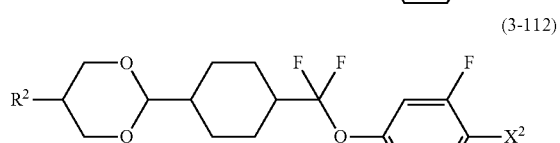
(3-112) 
(4-1) 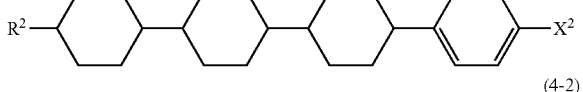
(4-2) 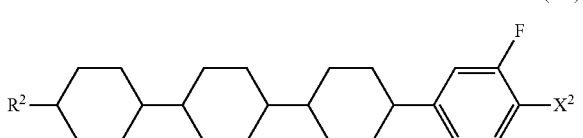
(4-3) 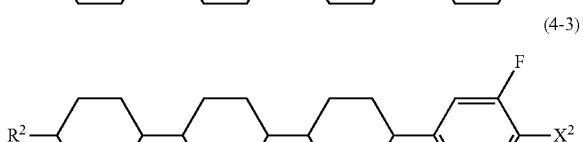
(4-4) 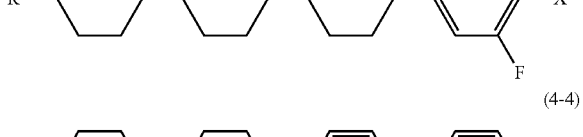
(4-5) 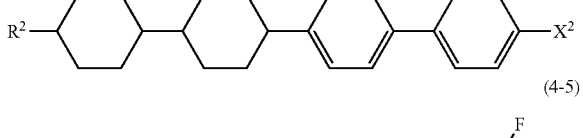
(4-6) 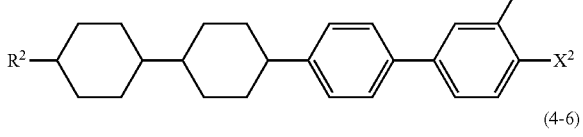
(4-7) 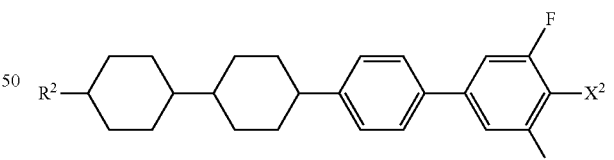
(4-8) 
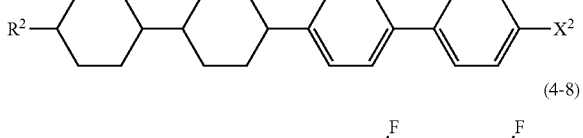
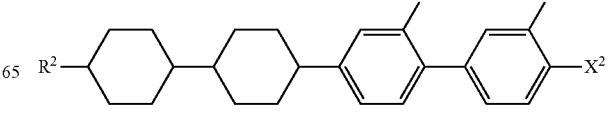

(4-9) 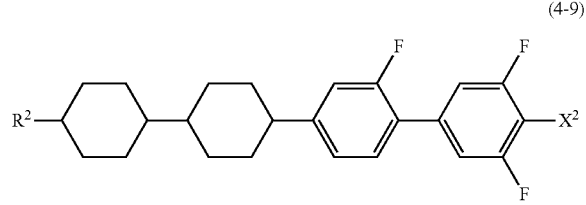
(4-10) 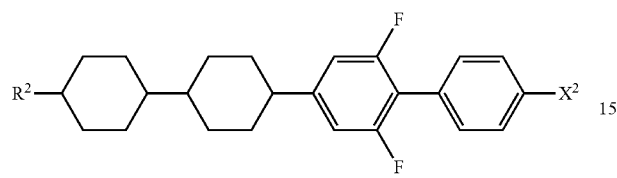
(4-11) 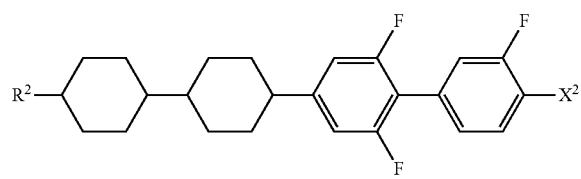
(4-12) 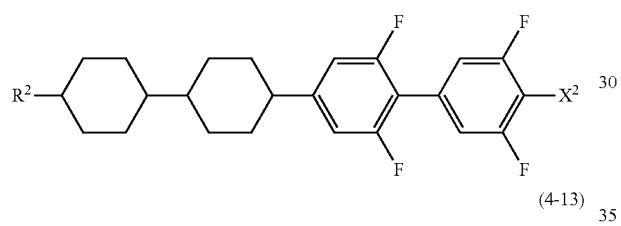
(4-13) 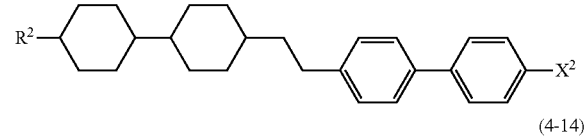
(4-14) 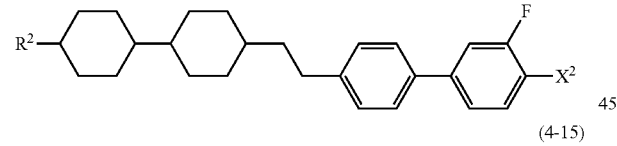
(4-15) 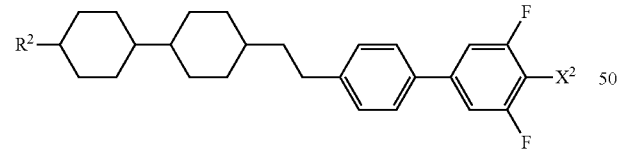
(4-16) 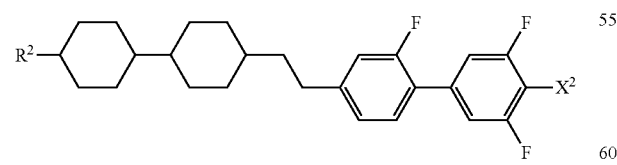
(4-17) 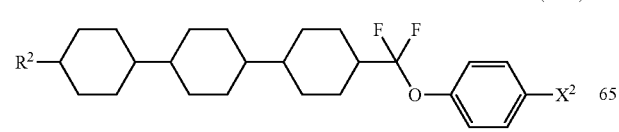
(4-18) 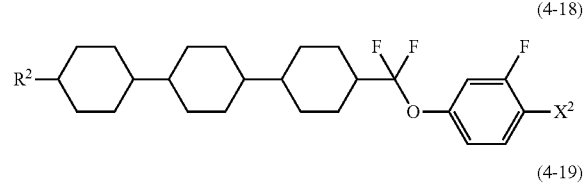
(4-19) 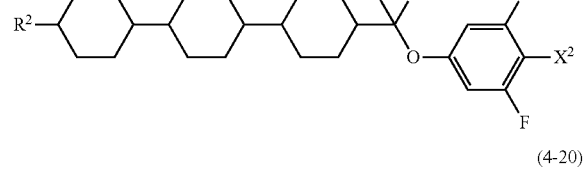
(4-20) 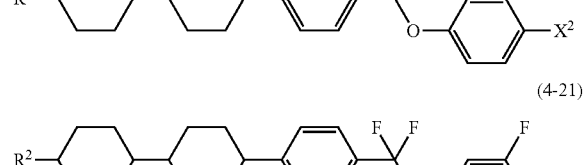
(4-21) 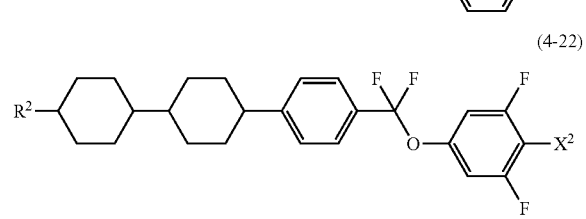
(4-22) 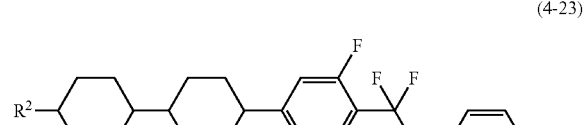
(4-23) 
(4-24) 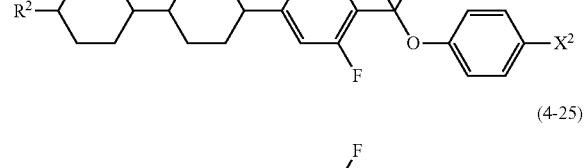
(4-25) 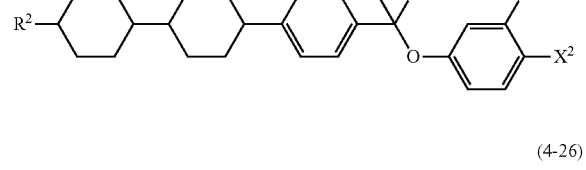
(4-26) 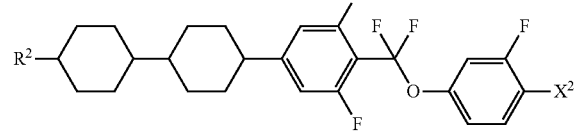

(4-27) 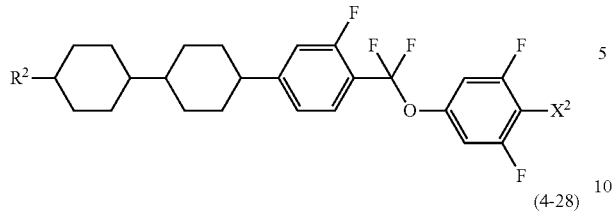
(4-28) 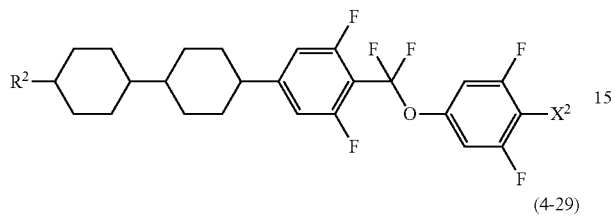
(4-29) 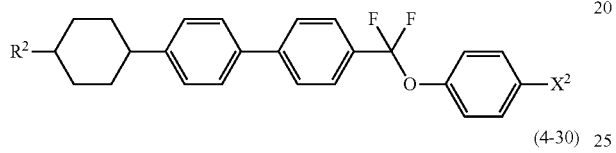
(4-30) 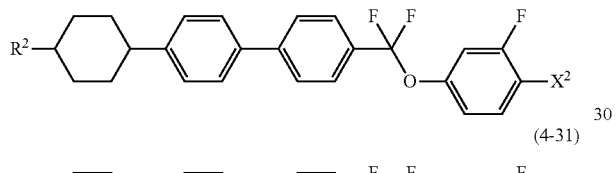
(4-31) 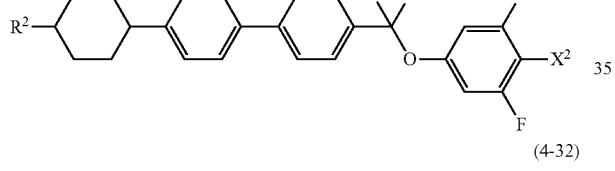
(4-32) 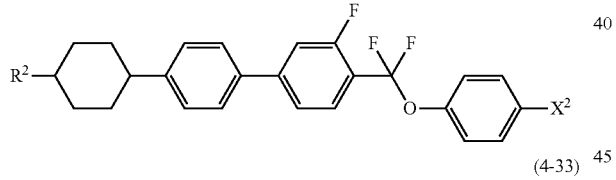
(4-33) 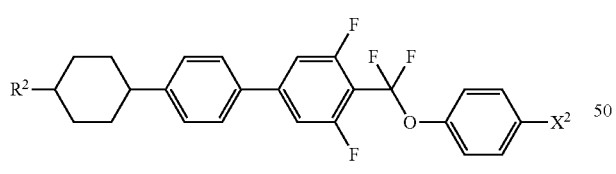
(4-34) 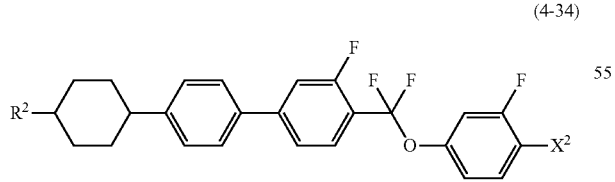
(4-35) 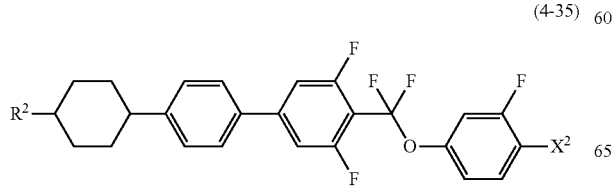
(4-36) 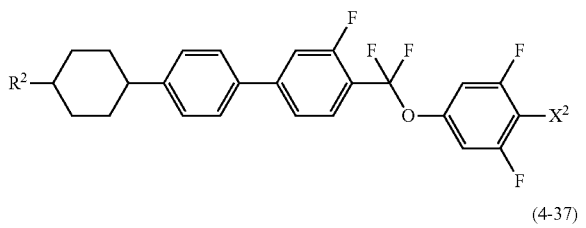
(4-37) 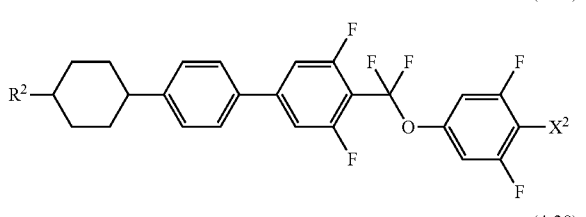
(4-38) 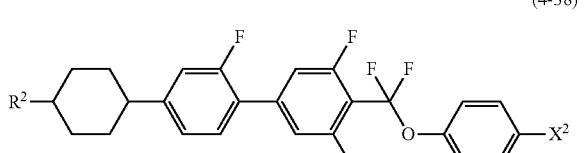
(4-39) 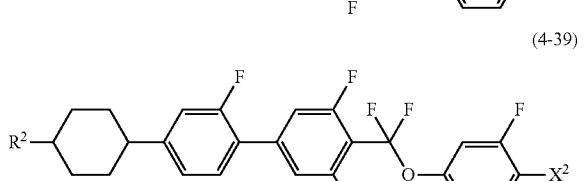
(4-40) 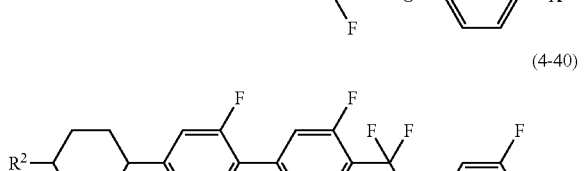
(4-41) 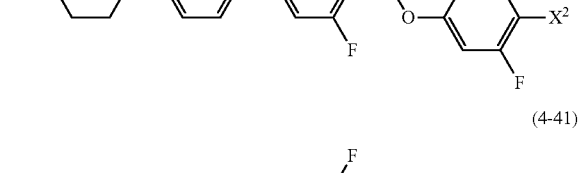
(4-42) 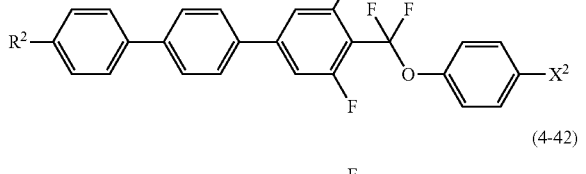
(4-43) 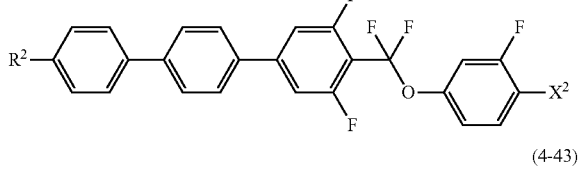
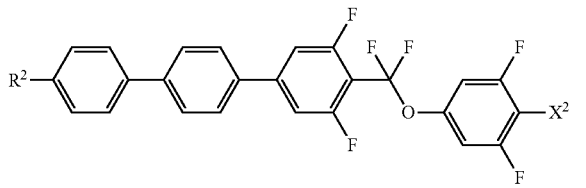

(4-44)
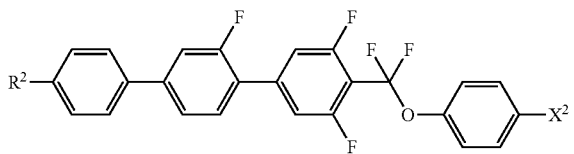

(4-45)
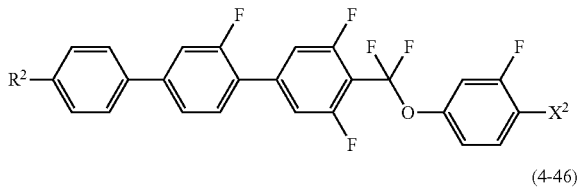

(4-46)
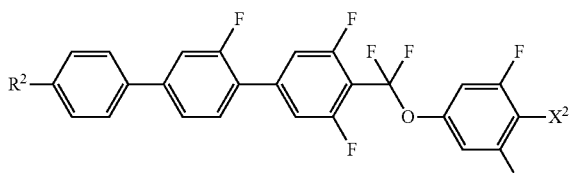

(4-47)
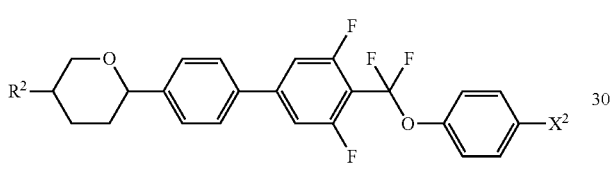

(4-48)
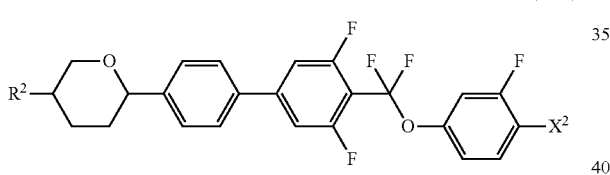

(4-49)
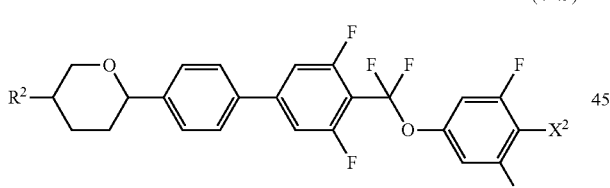

(4-50)
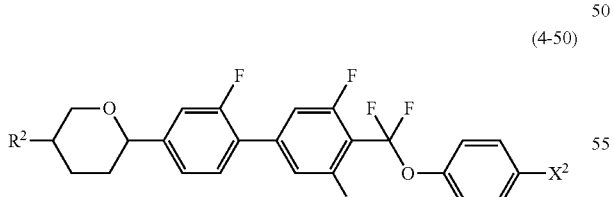

(4-51)
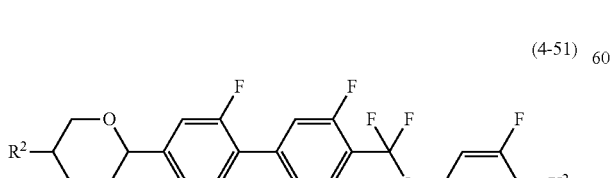

(4-52)
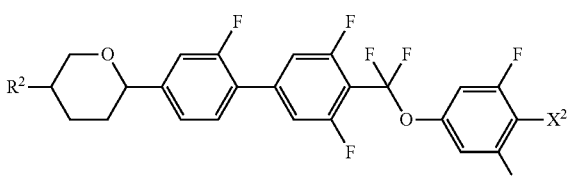

In these formulae, $R^2$ and $X^2$ are defined as above.

The compounds of formulae (2)-(4) (i.e., component B) have positive dielectric anisotropy and very good thermal or chemical stability, thus being useful in preparing a liquid crystal composition for TFTs. Relative to the total weight of the liquid crystal composition, the content of the component B in the liquid crystal composition of this invention is suitably 1-99 wt %, preferably 10-97 wt % and more preferably 40-95 wt %.

Preferred examples of the compound of formula (5) (i.e., component C) are formulae (5-1) to (5-62).

(5-1)
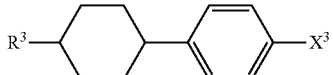

(5-2)

(5-3)
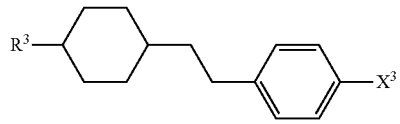

(5-4)
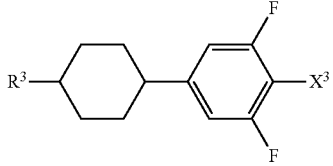

(5-5)
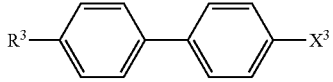

(5-6)
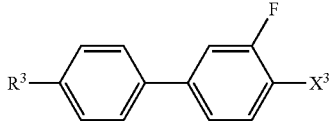

(5-7)
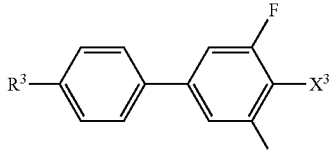

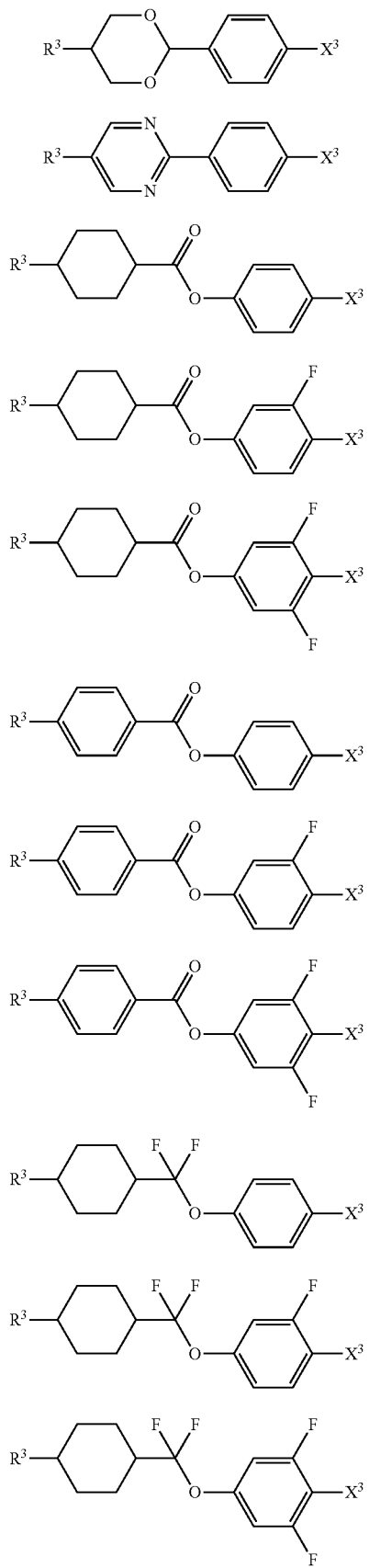
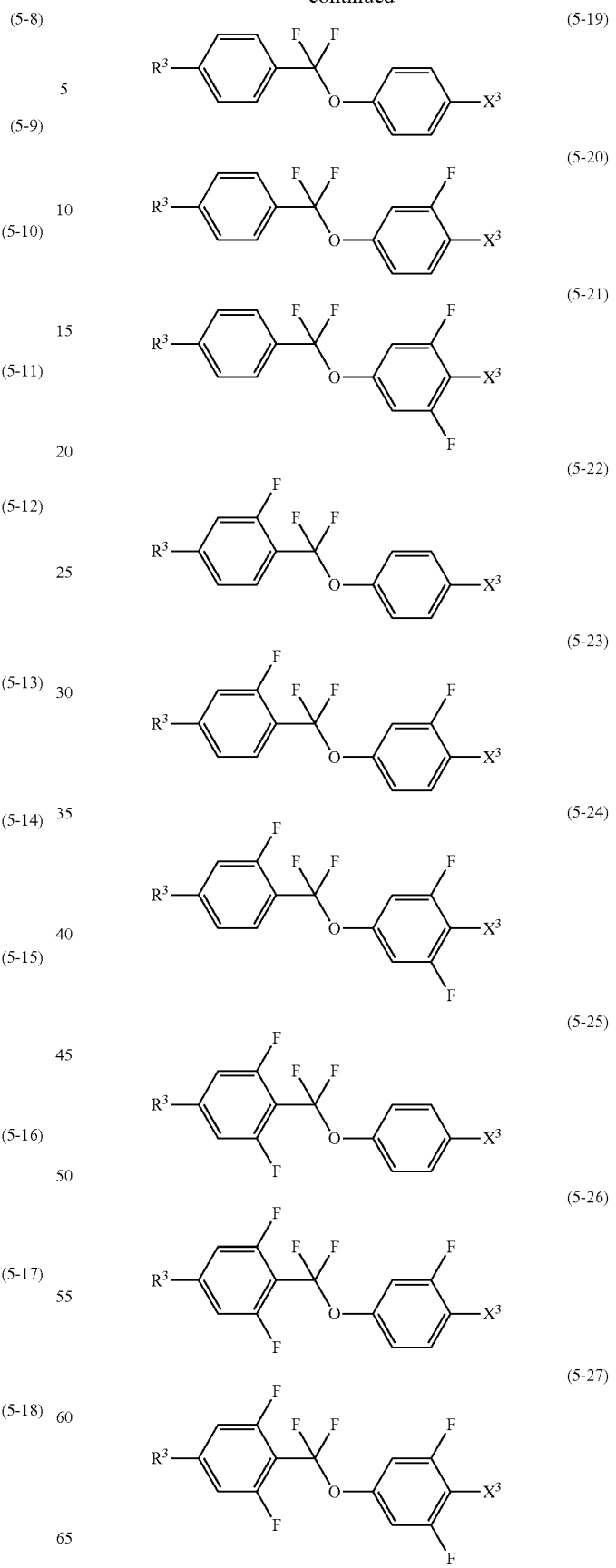

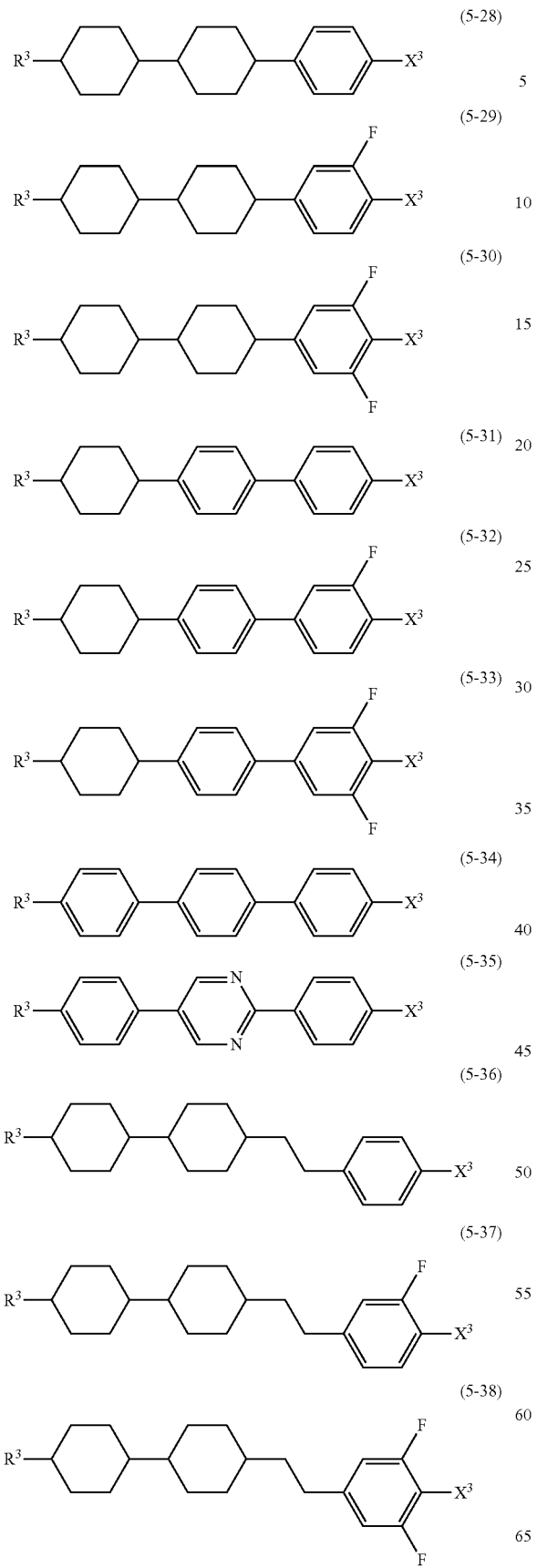
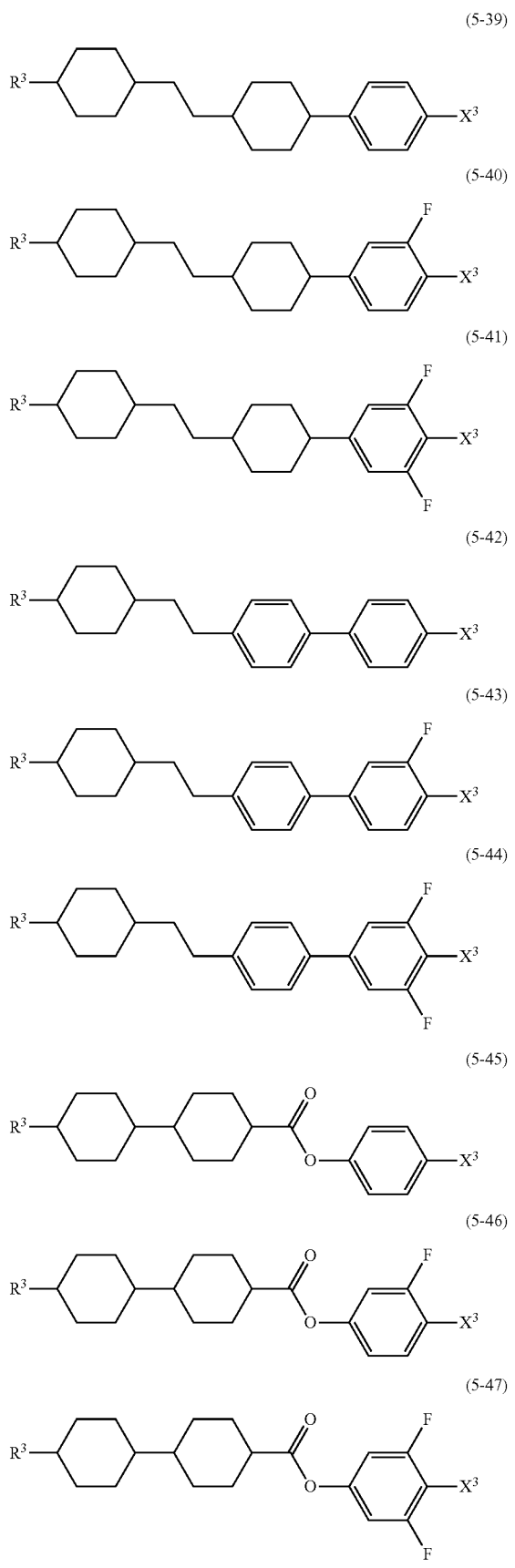

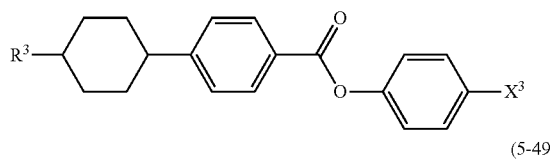
(5-48)

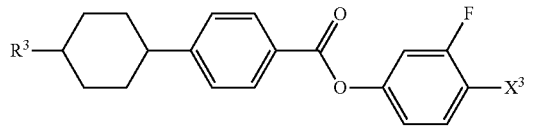
(5-49)

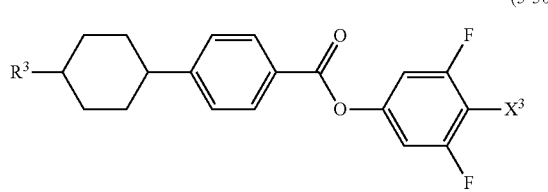
(5-50)

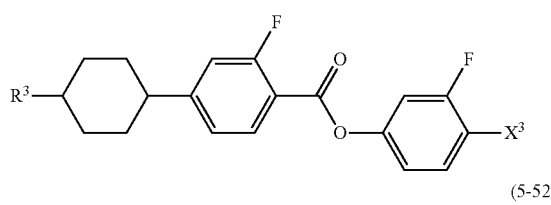
(5-51)

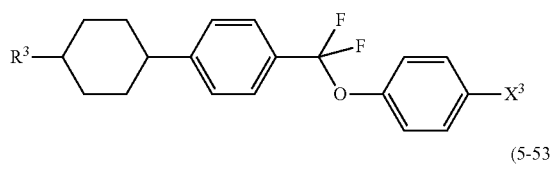
(5-52)

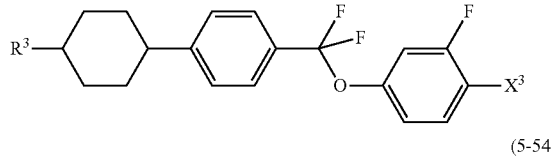
(5-53)

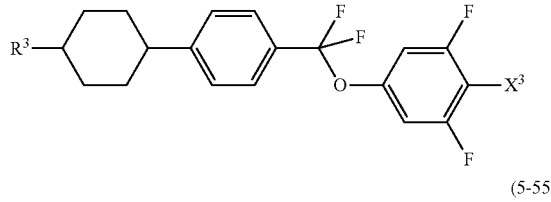
(5-54)

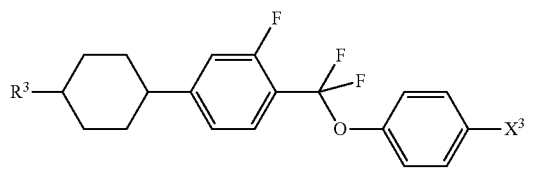
(5-55)

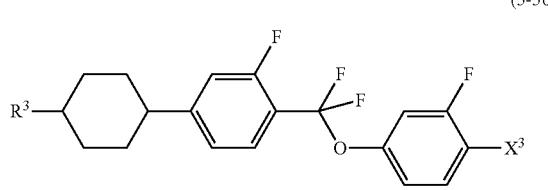
(5-56)

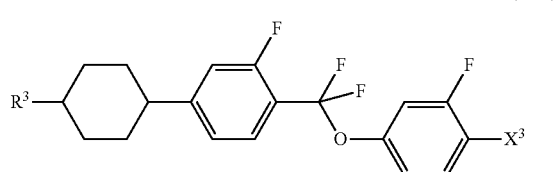
(5-57)

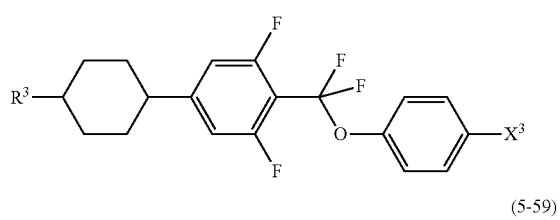
(5-58)

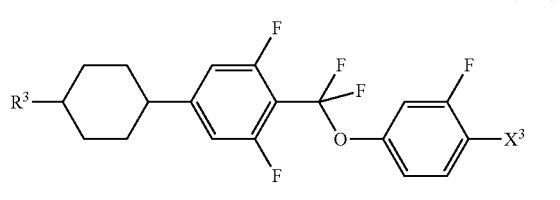
(5-59)

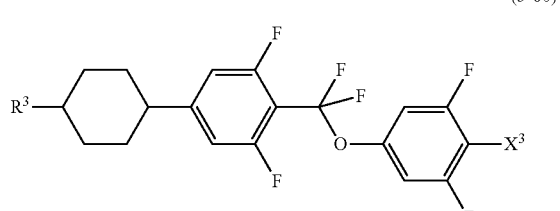
(5-60)

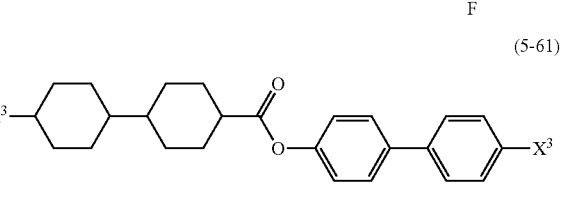
(5-61)

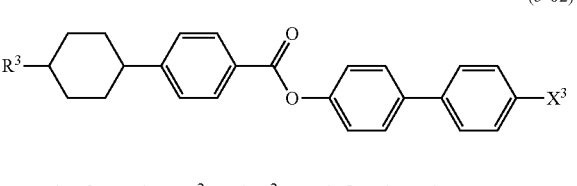
(5-62)

In the formulae, $R^3$ and $X^3$ are defined as above.

The compounds of formula (5) (i.e., component C) has a very large positive dielectric anisotropy. When the liquid crystal composition contains the component C, the driving voltage of the composition can be lowered, the viscosity and the optical anisotropy can be adjusted, and the temperature range of liquid crystal phase can be broadened.

Relative to the total weight of the composition, the content of the component C is preferably 0.1-99.9 wt %, more preferably 10-97 wt % and still more preferably 40-95 wt %. Further, the threshold voltage, the temperature range of liquid crystal phase, the optical anisotropy, the dielectric anisotropy, and the viscosity can be adjusted by mixing the components below.

Preferred examples of the compound of formula (6) (i.e., component D) are formulae (6-1)-(6-6).

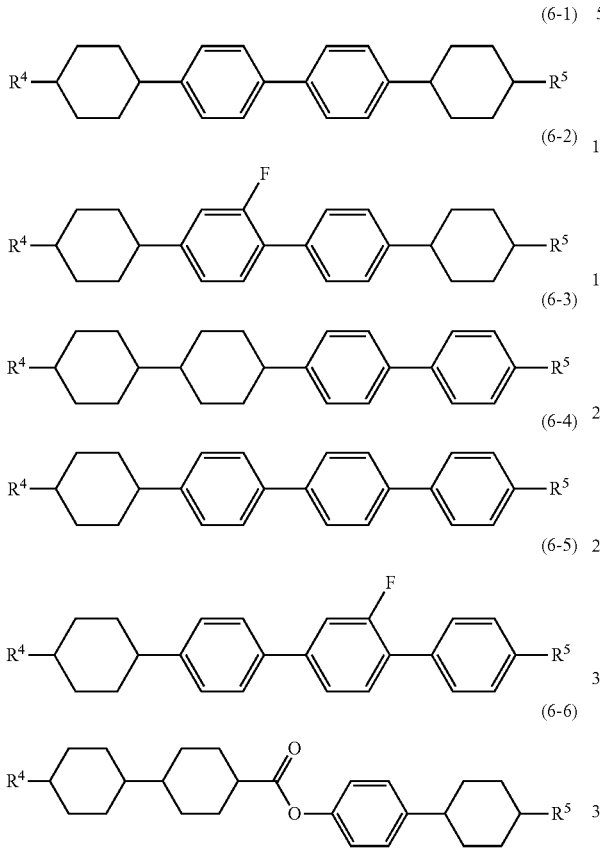

In the formulae, $R^4$ and $R^5$ are defined as above.

A compound of formula (6) (i.e., component D) has a dielectric anisotropy with a small absolute value and is nearly neutral. A compound of formula (6) has the effect of broadening the temperature range of the optically isotropic liquid crystal phase, such as increasing the clear point, or has the effect of adjusting the optical anisotropy.

If the content of the compounds of the component D is increased, the driving voltage of the liquid crystal composition is raised and the viscosity is lowered. Therefore, the compounds of the component D are expected to have a content as high as possible, provided that the desired driving voltage of the liquid crystal composition can be met. In the preparation of a liquid crystal composition for TFTs, the content of the component D is preferably 60 wt % or less, and more preferably 40 wt % or less, relative to the total weight of the composition.

The liquid crystal composition of this invention contains 0.1-99 wt % of at least one compound of formula (1) of this invention, which is beneficial to exhibition of good properties.

The liquid crystal composition of this invention generally can be prepared by a known method, for example, a method in which essential components are dissolved at high temperature.

3. Compounds (7)-(11)

A third aspect of this invention is a liquid crystal composition obtained by adding a component selected from the components E and F below to the component A.

A preferred component added to the component A is a mixture obtained by mixing the component E or F, wherein the component E includes at least one compound selected from the group consisting of compounds of formulae (7), (8), (9) and (10) shown above, and the component F includes at least one compound selected from the group consisting of compounds of formula (11) shown above.

Moreover, for each component of the liquid crystal composition used in this invention, an analogue containing isotopes of each element also can be used due to the small difference in physical properties.

For the component E, preferred examples of the compound of formula (7) are formulae (7-1) to (7-8), preferred examples of the compound of formula (8) are formulae (8-1) to (8-26), preferred examples of the compound of formula (9) are formulae (9-1) to (9-22), and preferred examples of the compound of formula (10) are formulae (10-1) to (10-5).

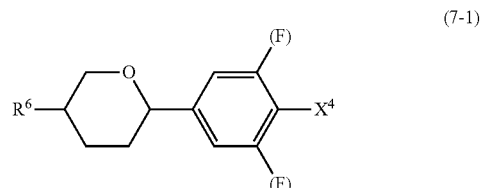

(7-1)

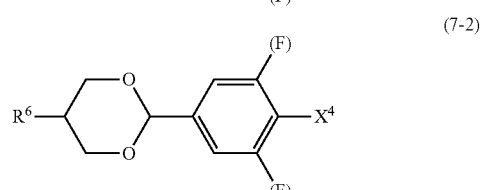

(7-2)

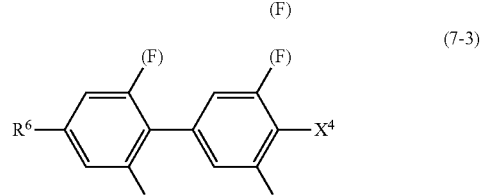

(7-3)

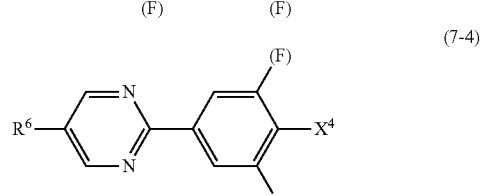

(7-4)

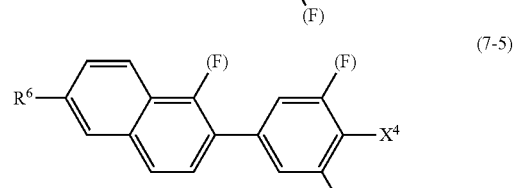

(7-5)

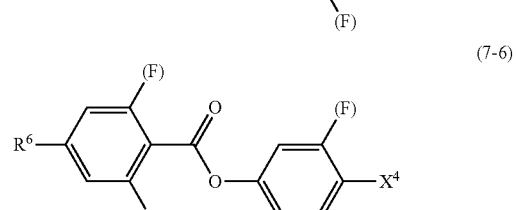

(7-6)

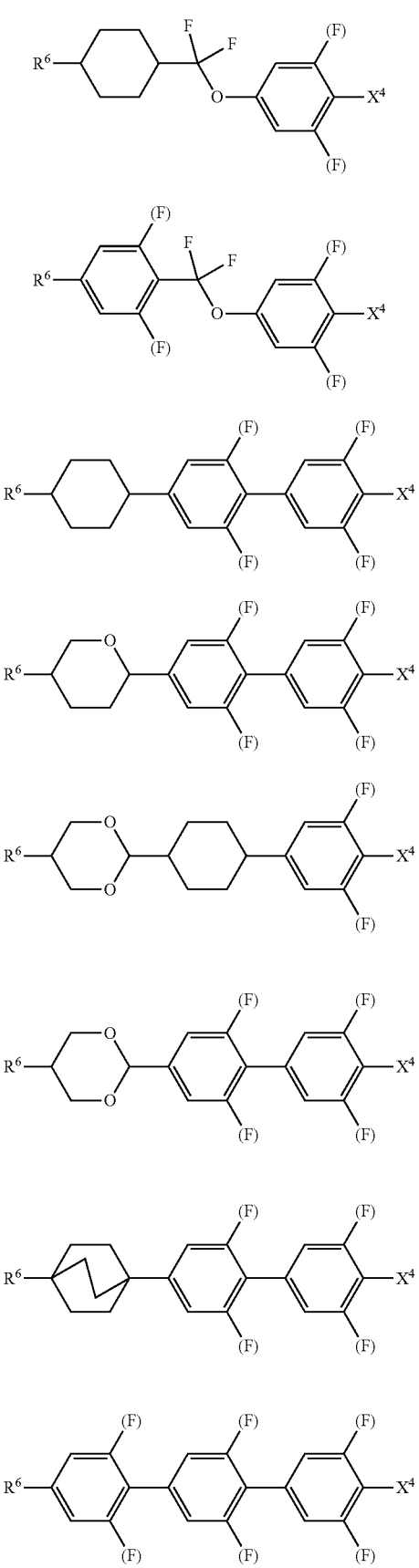
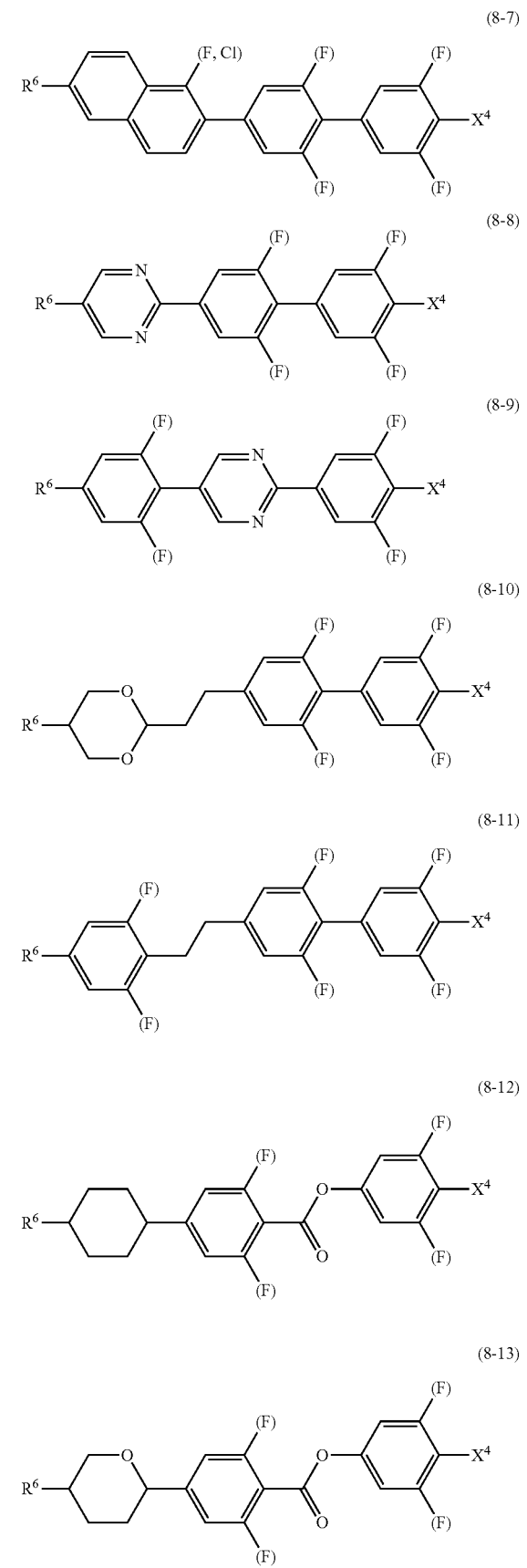

(8-14)
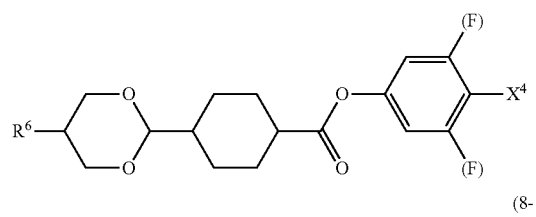
(8-15)
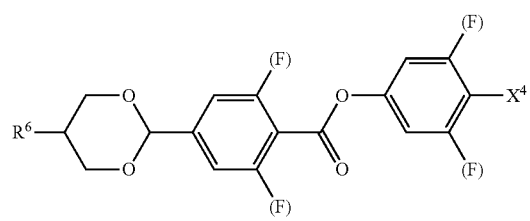
(8-16)
(8-17)
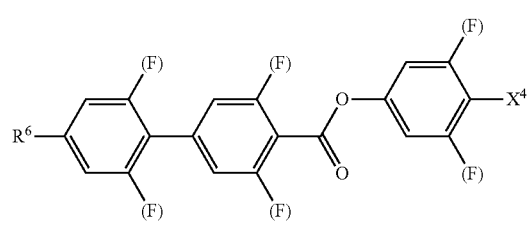
(8-18)
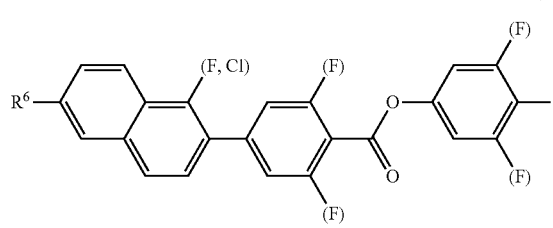
(8-19)
(8-20)
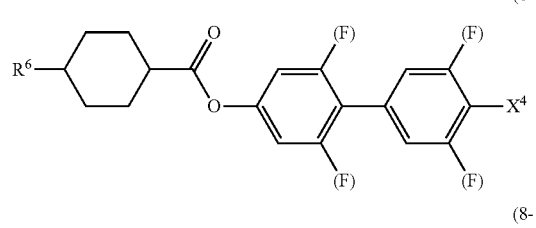
(8-21)
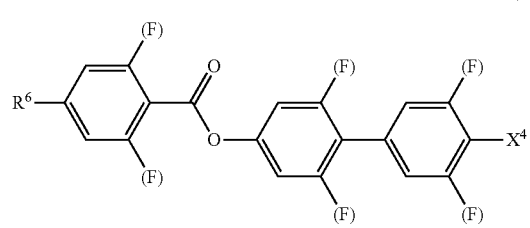
(8-22)
(8-23)
(8-24)
(8-25)
(8-26)
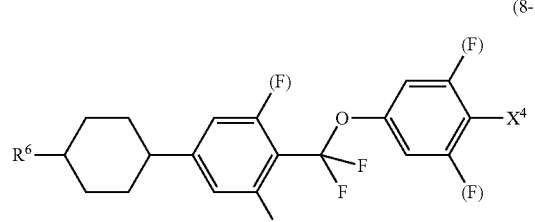
(9-1)

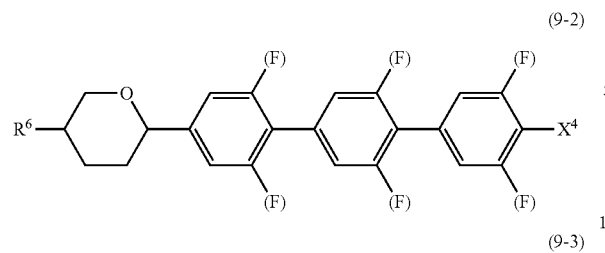
(9-2)
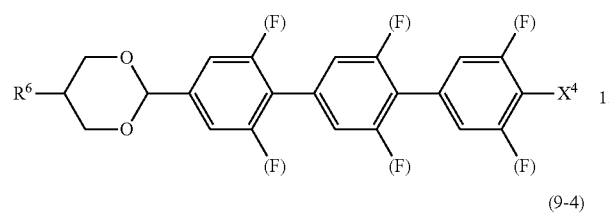
(9-3)
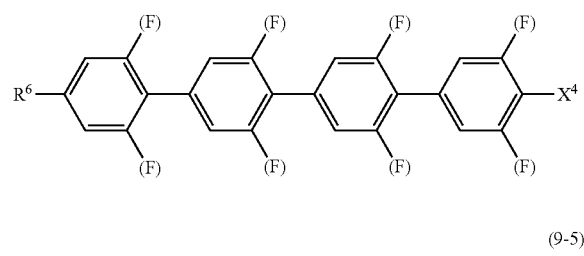
(9-4)
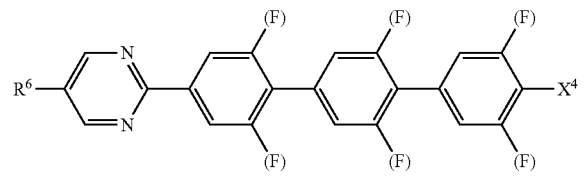
(9-5)
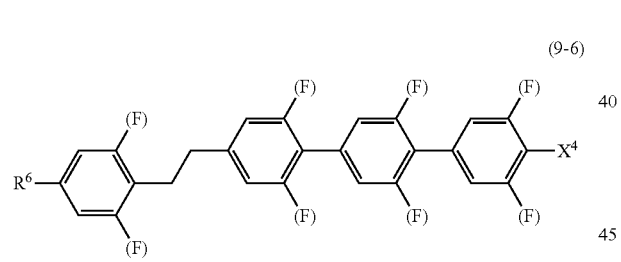
(9-6)
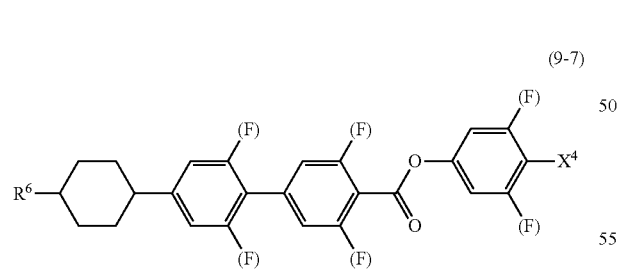
(9-7)
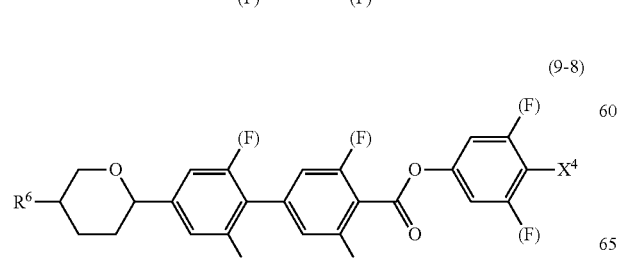
(9-8)
(9-9)
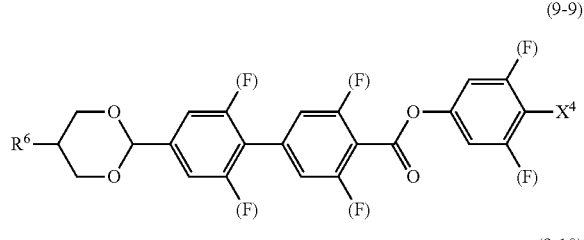
(9-10)
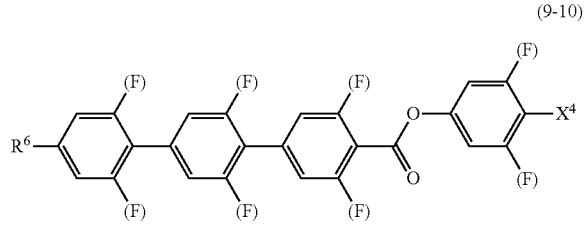
(9-11)
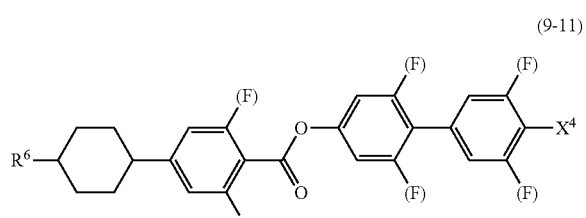
(9-12)
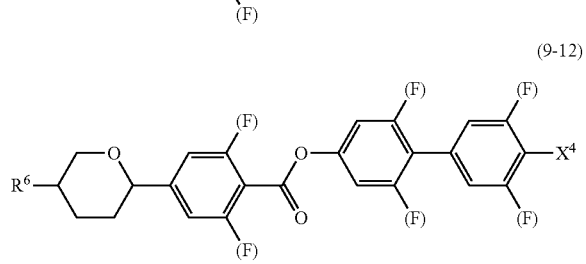
(9-13)
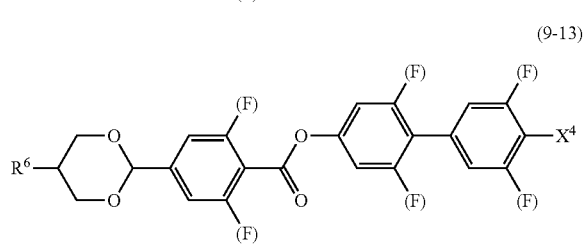
(9-14)
(9-15)

(9-16)
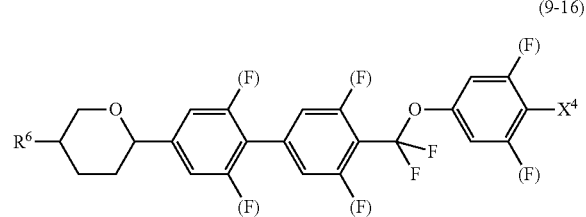

(9-17)
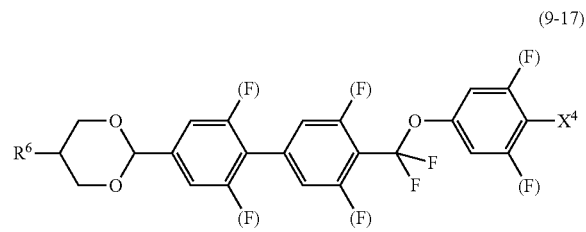

(9-18)
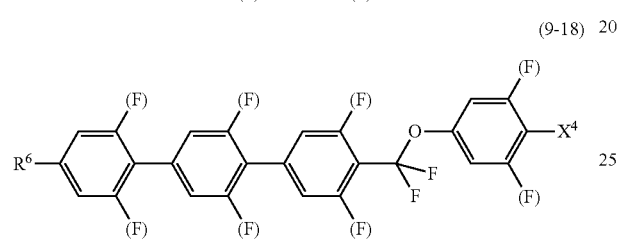

(9-19)
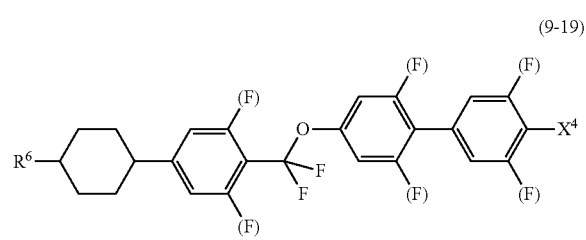

(9-20)
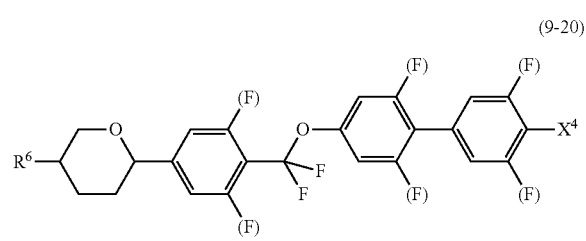

(9-21)
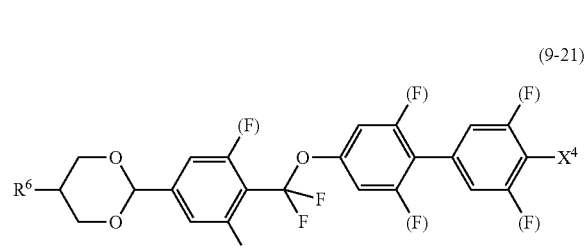

(9-22)
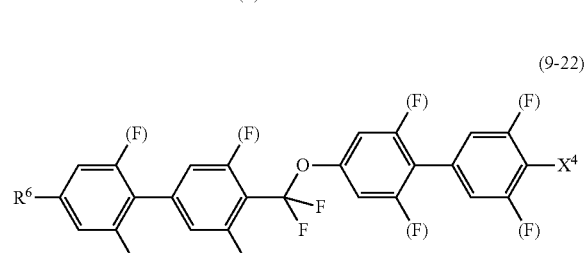

(10-1)
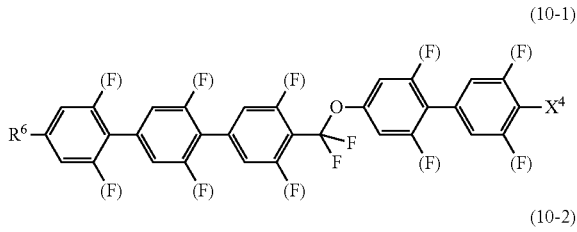

(10-2)
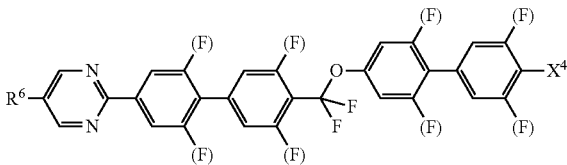

(10-3)
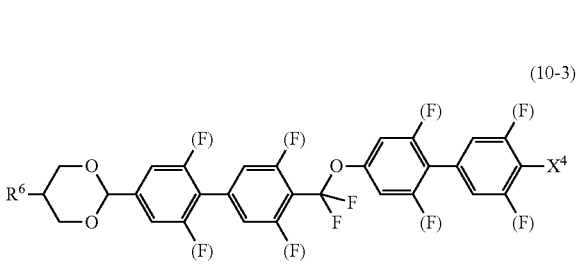

(10-4)
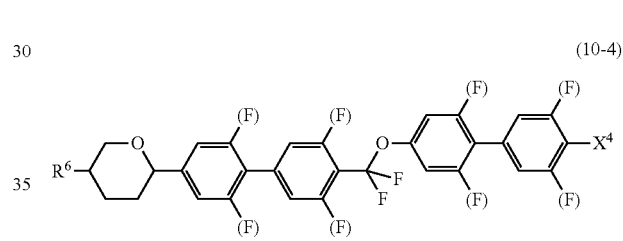

(10-5)
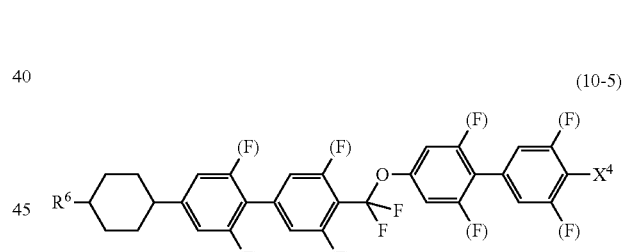

In the formulae, $R^6$ and $X^4$ are defined as above, (F) denotes hydrogen or fluorine, and (F, Cl) denotes hydrogen, fluorine or chlorine.

The compounds of formulae (7)-(10) (i.e., component E) have very large positive dielectric anisotropy and very good thermal and chemical stability, thus being suitable in preparing a liquid crystal composition used for active driving like TFT driving. In the liquid crystal composition of this invention, the content of the component E is suitably 1-99 wt %, preferably 10-97 wt % and more preferably 40-95 wt %, relative to the total weight of the liquid crystal composition. Further, when the liquid crystal composition further contains a compound of formula (6) (i.e., component D), the clear point and the viscosity can be adjusted.

Preferred examples of the compound of formula (11) shown above (i.e., component F) are formulae (11-1) to (11-37).

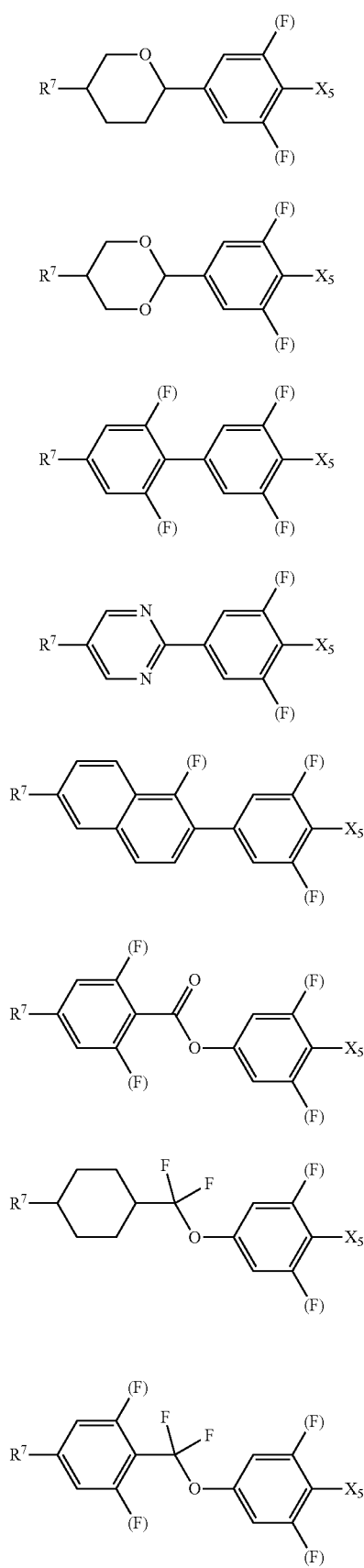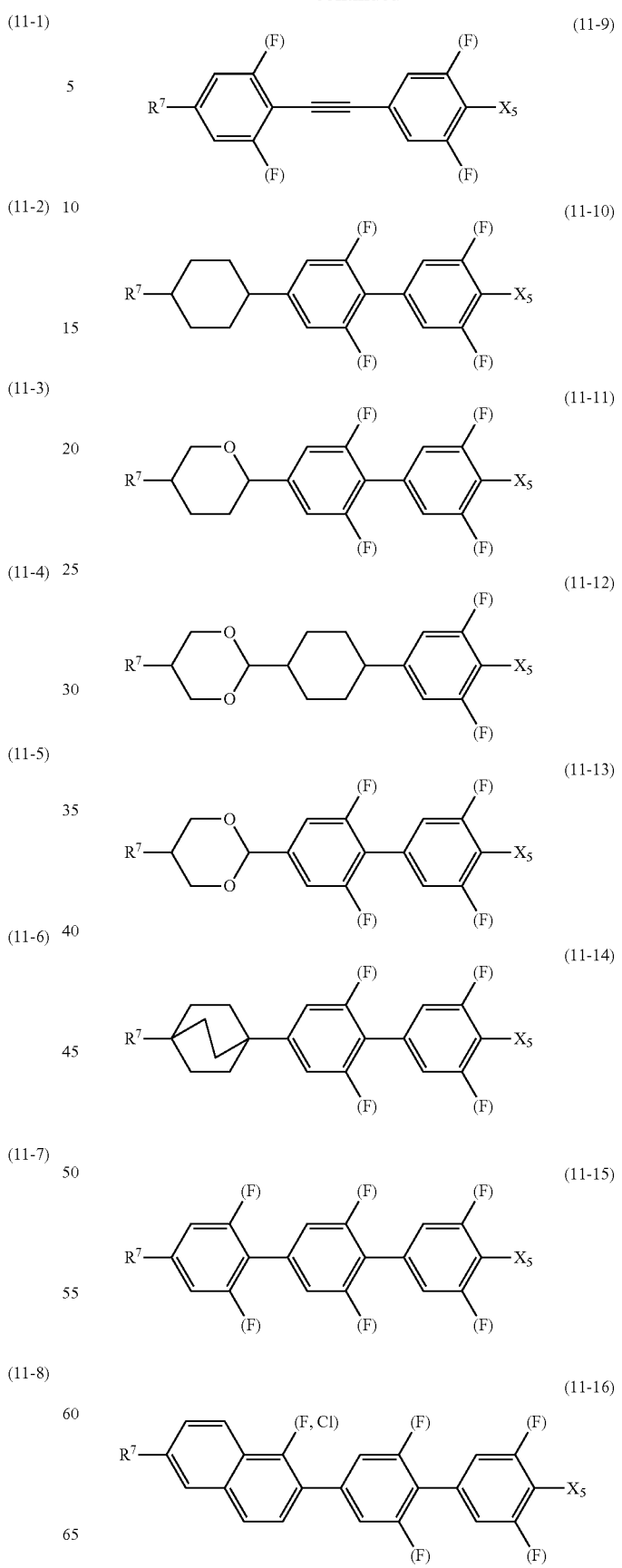

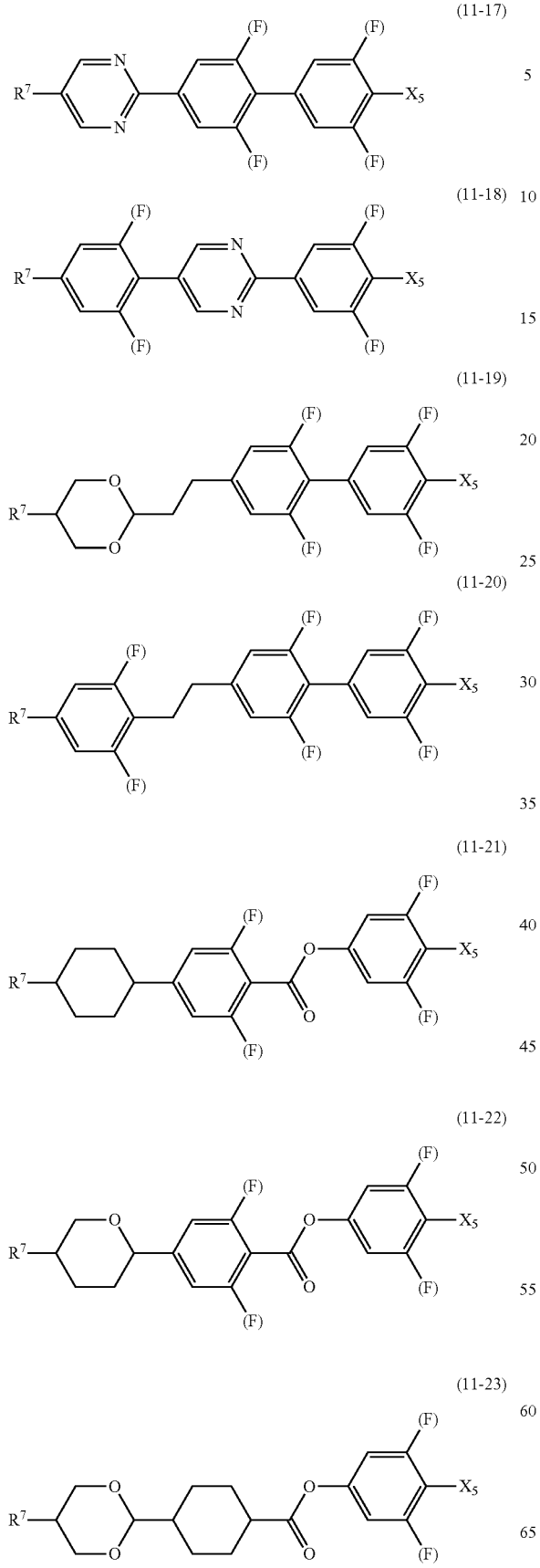

-continued

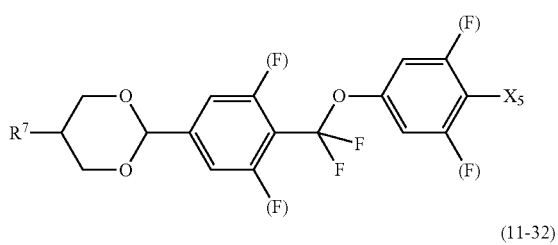
(11-31)

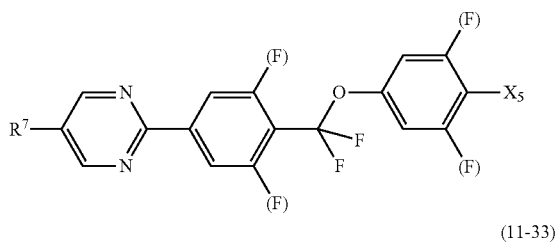
(11-32)

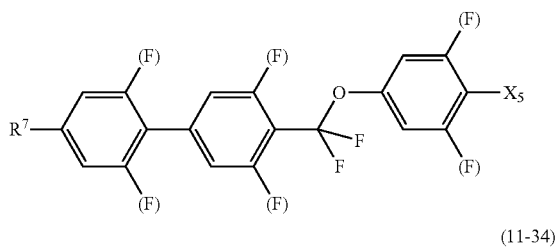
(11-33)

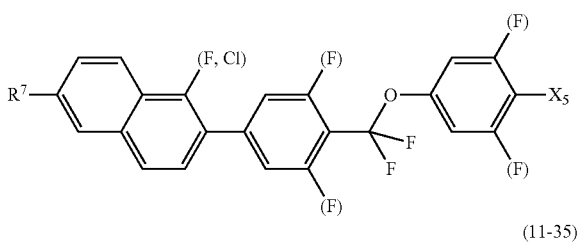
(11-34)

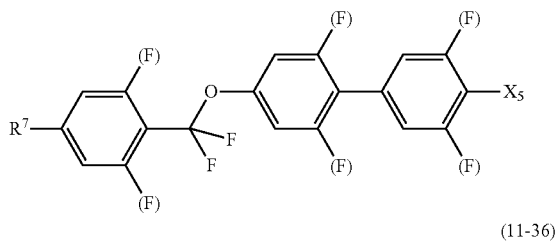
(11-35)

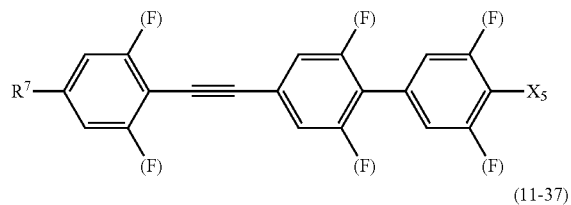
(11-36)

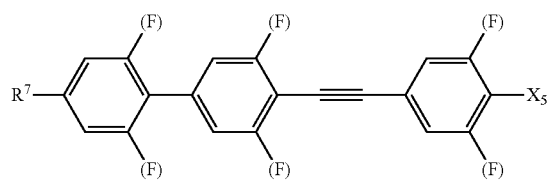
(11-37)

In the formulae, $R^7$, $X^5$, (F) and (F, Cl) are defined as above.

These compounds of formula (11) (i.e., component F) have very large positive dielectric anisotropy, thus being mainly used to lower the driving voltage of devices driven in an optically isotropic liquid crystal phase, polymer dispersed LCD (PDLCD), polymer network LCD (PNLCD), polymer-stabilized cholesteric LCD (PSCLCD) and so on. When the liquid crystal composition contains the component F, the driving voltage of the composition can be lowered, the viscosity and the optical anisotropy can also be adjusted, and the temperature range of the liquid crystal phase can be broadened. Moreover, the component F can also be used to improve the steepness of the voltage-transparency curve.

The content of the component F is preferably 0.1-99.9 wt %, more preferably 10-97 wt % and still more preferably 40-95 wt %, relative to the total weight of the composition.

4. Composition Having Optically Isotropic Liquid Crystal Phase 4-1. Components of Composition Having Optically Isotropic Liquid Crystal Phase A fourth aspect of this invention is a composition containing a compound of formula (1) and a chiral dopant, which is a liquid crystal composition useful in an optical device driven in an optically isotropic liquid crystal phase and exhibiting an optically isotropic liquid crystal phase.

The compound of formula (1) has a low clear point, a large dielectric anisotropy and a large optical anisotropy, and the content of the compound of formula (1) can be 5-100 wt %, preferably 5-80 wt % and more preferably 10-70 wt %, relative to the total weight of the achiral liquid crystal composition without a chiral dopant.

The content of the chiral dopant is preferably 1-40 wt %, more preferably 3-25 wt % and still more preferably 5-15 wt %, relative to the total weight of the liquid crystal composition. A liquid crystal composition in which the content of the chiral dopant is in the above range can have an optically isotropic liquid crystal phase and is preferred.

The chiral dopant contained in the liquid crystal composition may be a single species, or a mixture of two or more species.

4-2. Chiral Dopant

The chiral dopant contained in the optically isotropic liquid crystal composition is preferably a compound with a high helical twisting power. When a compound with a high helical twisting power is used, the addition amount required for obtaining a desired pitch is reduced, thus preventing the driving voltage from being raised and being advantageous in practice. Specifically, the compounds of formulas (K1)-(K5) below are preferred.

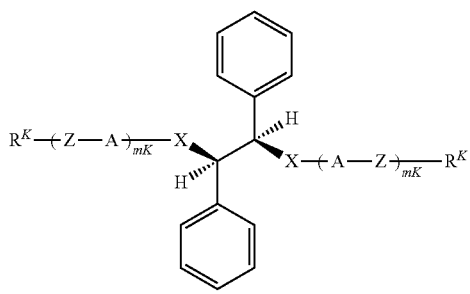
(K1)

-continued

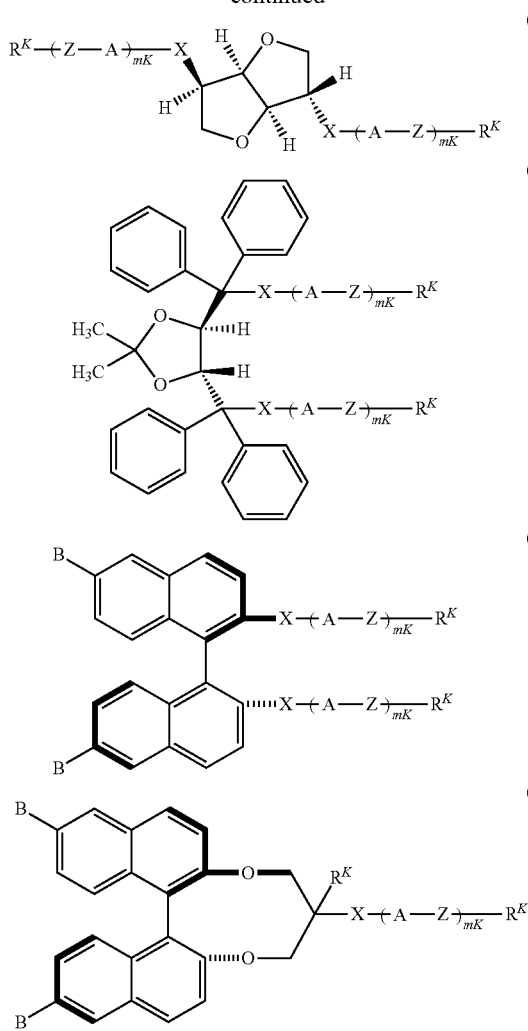

In formulae (K1)-(K5), the plural $R^K$ are independently hydrogen, halogen, —N=C=O, —N=C=S, or a $C_{1-20}$ alkyl in which arbitrary —CH$_2$— may be substituted with —O—, —S—, —COO—, —OCO—, —CH=CH—, —CF=CF— or —C≡C— and arbitrary hydrogen may be substituted with halogen; the plural A are independently an aromatic or non-aromatic 3- to 8-membered ring or a fused ring of 9 or more carbons, and in these rings arbitrary hydrogen may be substituted with halogen, $C_{1-3}$ alkyl or $C_{1-3}$ haloalkyl, —CH$_2$— may be substituted with —O—, —S— or —NH—, and —CH= may be substituted with —N=; the plural B are independently hydrogen, halogen, $C_{1-3}$ alkyl, $C_{1-3}$ haloalkyl, an aromatic or non-aromatic 3- to 8-membered ring or a fused ring of 9 or more carbons, and in these rings arbitrary hydrogen may be substituted with halogen, $C_{1-3}$ alkyl or $C_{1-3}$ haloalkyl, —CH$_2$— may be substituted with —O—, —S— or —NH—, and —CH= may be substituted with —N=; the plural Z are independently a single bond, or $C_{1-8}$ alkylene in which arbitrary —CH$_2$— may be substituted with —O—, —S—, —COO—, —OCO—, —CSO—, —OCS—, —N=N—, —CH=N—, —N=CH—, —CH=CH—, —CF=CF— or —C≡C— and arbitrary hydrogen may be substituted with halogen; X is a single bond, —COO—, —OCO—, —CH$_2$O—, —OCH$_2$—, —CF$_2$O—, —OCF$_2$— or —CH$_2$CH$_2$—; and mK is 1-4.

Among the compounds, the chiral dopant added in the liquid crystal composition is preferably selected from formulae (K2-1)-(K2-8) covered by formula (K2), formulae (K4-1)-(K4-6) covered by formula (K4), and formulae (K5-1)-(K5-3) covered by formula (K5).

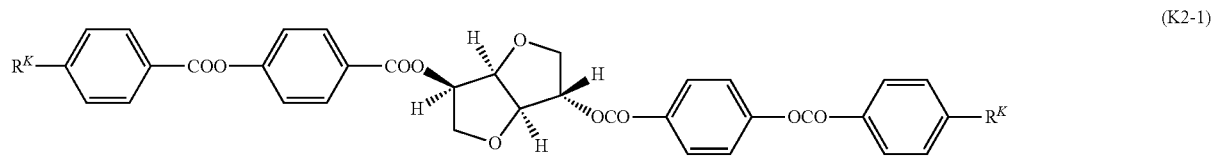

(K2-1)

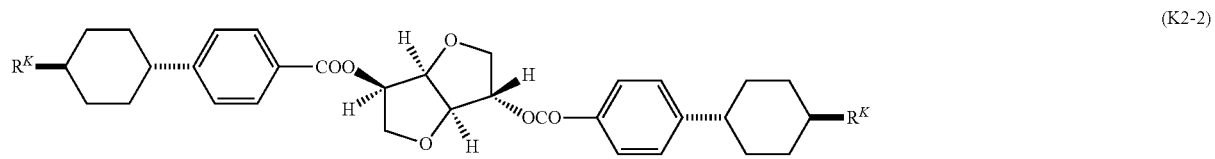

(K2-2)

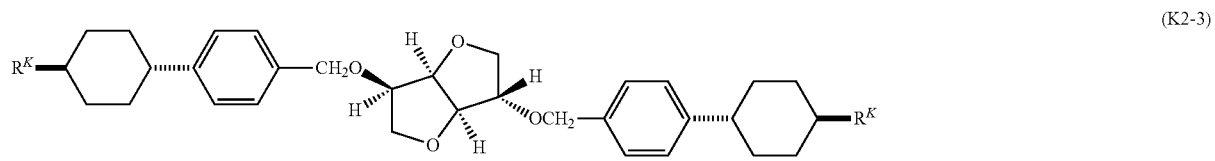

(K2-3)

(K2-4)
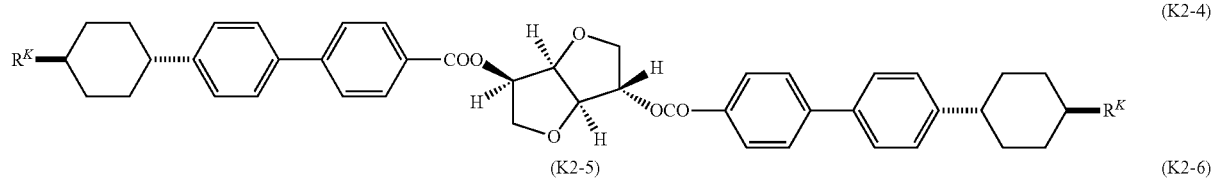
(K2-5) (K2-6)
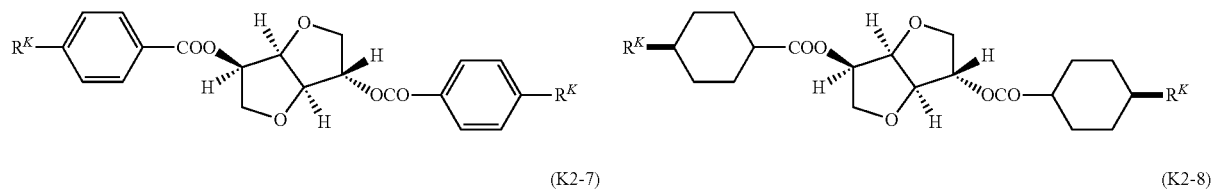
(K2-7) (K2-8)
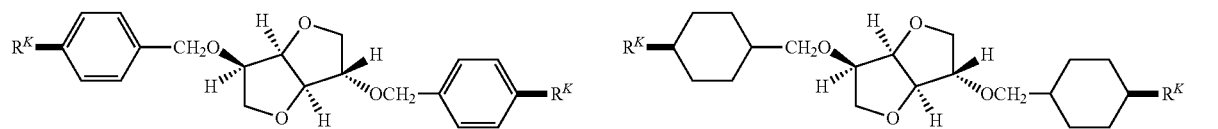
(K4-1) (K4-2)
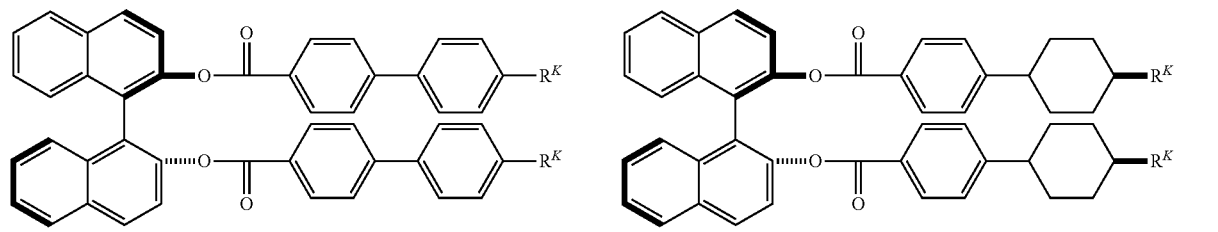
(K4-3)
(K4-4) (K4-5)
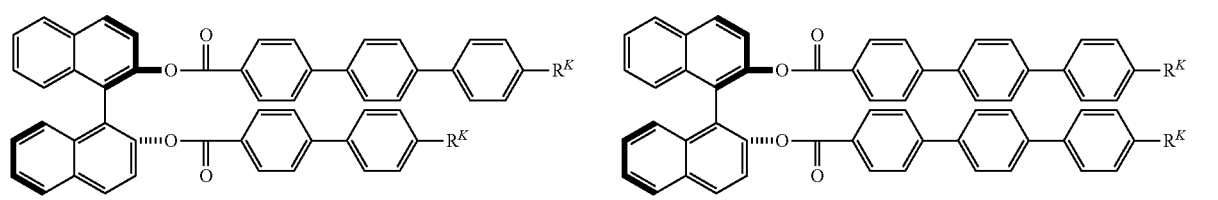
(K4-6) (K5-1)
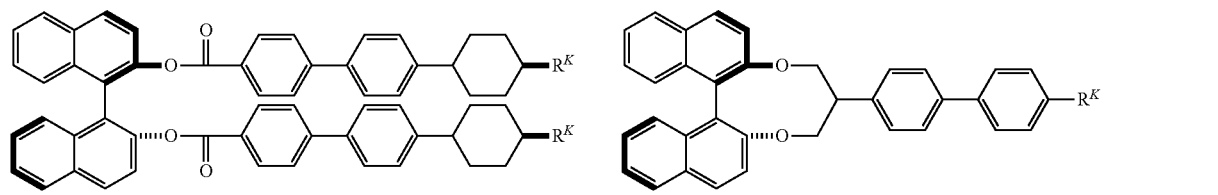

-continued (K5-2)
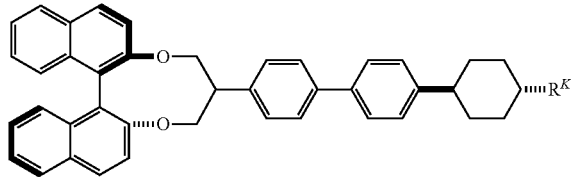

(K5-3)
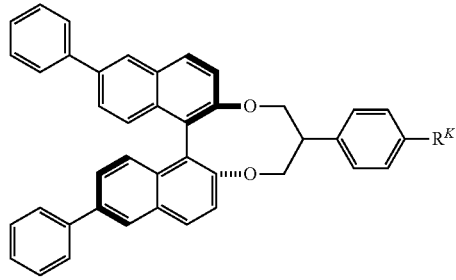

In the formulae, the plural $R^K$ are independently $C_{3-10}$ alkyl in which —$CH_2$-adjacent to a ring may be substituted with —O— and arbitrary —$CH_2$— may be substituted with —CH=CH—.

4-3. Optically Isotropic Liquid Crystal Phase

That a liquid crystal composition has optical isotropy means that the composition exhibits optical isotropy because of macroscopically isotropic arrangement of the liquid crystal molecules but has microscopic liquid crystal order. The pitch corresponding to the microscopic liquid crystal order of the liquid crystal composition (sometimes referred to as "pitch", hereinafter) is preferably 700 nm or less, more preferably 500 nm or less and still more preferably 350 nm or less.

Herein, the so-called "isotropic phase" refers to a commonly defined isotropic phase, i.e., disorder phase, or a phase that still exhibits isotropy due to fluctuation even when a region with a non-zero local order parameter is generated. For example, an isotropic phase formed at the high temperature side of a nematic phase is equivalent to the isotropic phase in this specification. The chiral liquid crystal in this specification also has a similar definition. Moreover, "optically isotropic liquid crystal phase" in this specification means a phase that exhibits optical isotropy without fluctuation, an example of which is a phase having platelet tissue, i.e., a blue phase in narrow sense.

The optically isotropic liquid crystal composition of this invention has an optically isotropic liquid crystal phase. However, the typical platelet structure in a blue phase is not observed under a polarizing microscope sometimes. Therefore, in this specification, a phase exhibiting the platelet structure is designated as a blue phase, and an optically isotropic liquid crystal phase including a blue phase is designated as an optically isotropic liquid crystal phase. That is, the blue phase is included in the optically isotropic liquid crystal phase.

Generally, the blue phase can be divided into three types, blue phase I, blue phase II and blue phase III, which are all optically active and isotropic. In a blue phase I or II, two or more diffracted light produced by Bragg reflection from different lattice planes are observed. The blue phase is generally observed between the isotropic phase and the chiral nematic phase.

That the optically isotropic liquid crystal phase does not exhibit two or more colors of diffracted light means that a platelet structure observed in a blue phase I or II is not observed and the phase substantially exhibits a single color in the entire plane. For an optically isotropic liquid crystal phase not exhibiting two or more colors of diffracted light, brightness/darkness of the color is not necessarily even in plane.

An optically isotropic liquid crystal phase not exhibiting two or more colors of diffracted light has the advantage of inhibiting the intensity of the reflected light caused by Bragg reflection, or shifting toward the short wavelength side.

Furthermore, when a liquid crystal material reflecting visible light is used in a display device, sometimes a color variation problem may occur. However, for a liquid crystal not exhibiting two or more colors of diffracted light, the reflection of visible light may be eliminated in the pitch larger than that in the blue phase in narrow sense (a phase exhibiting the platelet structure), as a result of reflection wavelength shift toward the short wavelength side.

The optically isotropic liquid crystal composition of this invention can be obtained by adding a chiral dopant to a composition having a nematic phase, wherein the chiral dopant is preferably added in a concentration such that the pitch is 700 nm or less. Further, the composition having a nematic phase contains the compound of formula (1) and other necessary components. Moreover, the optically isotropic liquid crystal composition of this invention can alternatively be obtained by adding a chiral dopant to a composition having a chiral nematic phase but no optically isotropic liquid crystal phase. The composition having a chiral nematic phase but no optically isotropic liquid phase contains a compound of formula (1), an optically active compound and other necessary components, where the optically active compound is preferably added in a concentration such that the pitch is 700 nm or more, so as not to exhibit an optically isotropic liquid crystal phase. The optically active compounds to be added can be the above compounds with a high helical twisting power, that is, the compounds of formulae (K1)-(K5), (K2-1)-(K2-8) & (K5-1)-(K5-3). Moreover, the optically active compound added may not have a so high helical twisting power. Such an optically active compound is, for example, one added in a liquid crystal composition for a device driven in a nematic phase (TN mode or STN mode, etc.).

Examples of the optically active compound without a high helical twisting power are the following optically active compounds (Op-1)-(Op-13).

(Op-1)
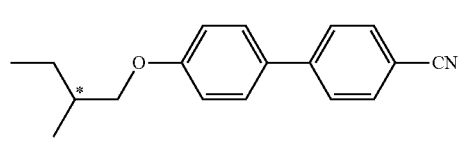

(Op-2)
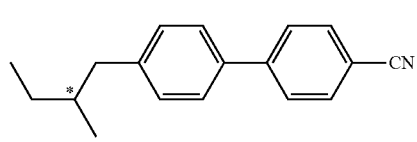

-continued
(Op-3)
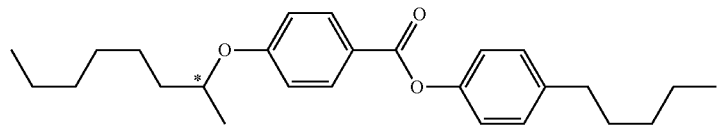
(Op-4)
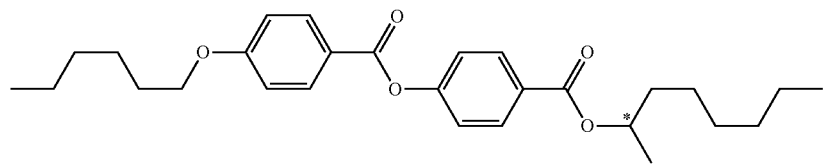
(Op-5)
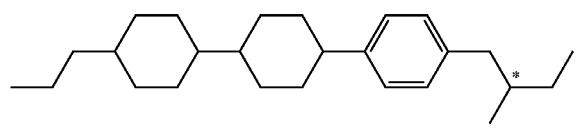
(Op-6)
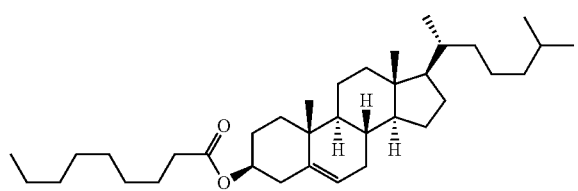
(Op-7)
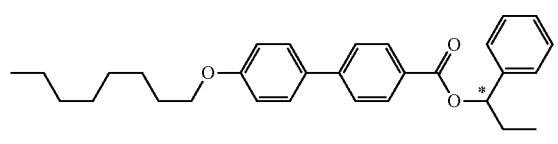
(Op-8)
(Op-9)
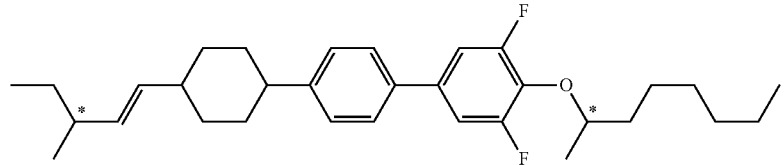
(Op-10)
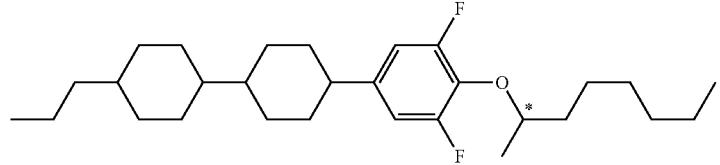
(Op-11)
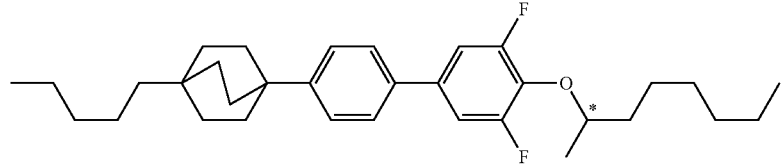
(Op-12)
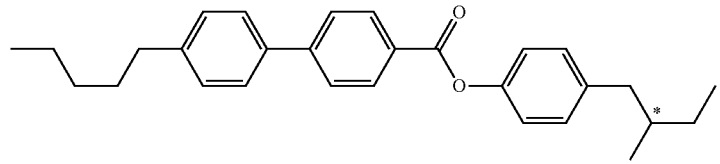

(Op-13)

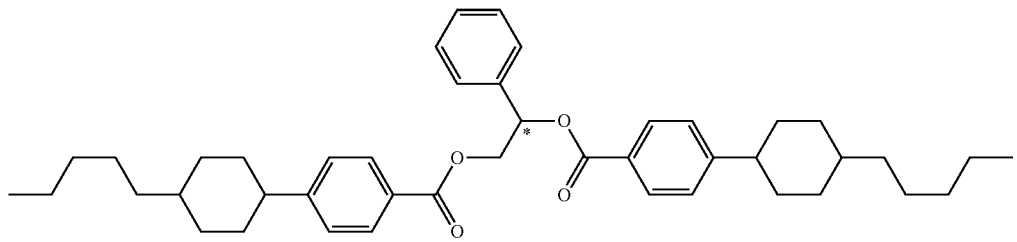

Moreover, the temperature range of the optically isotropic liquid crystal composition of this invention can be broadened by adding a chiral dopant to a liquid crystal composition having a wide temperature range of co-existence of a nematic phase or a chiral nematic phase and an isotropic phase for exhibiting an optically isotropic liquid crystal phase. For example, a composition exhibiting an optically isotropic liquid crystal phase in a wide temperature range can be prepared as follows. A liquid crystal compound having a high clear point is mixed with a liquid crystal compound having a low clear point to prepare a liquid crystal composition with a wide temperature range of co-existence of a nematic phase and an isotropic phase. Then, a chiral dopant is added to the liquid crystal composition.

For a liquid crystal composition with a wide co-existence temperature range of a nematic phase or chiral nematic phase and an isotropic phase, the difference between the upper-limit temperature and the lower-limit temperature of the co-existence is preferably 3-150° C. and more preferably 5-150° C. Moreover, the liquid crystal composition preferably has a difference of 3-150° C. between the upper-limit temperature and lower-limit temperature of the co-existence of the nematic phase and the isotropic phase.

When an electric field is applied to the liquid crystal medium of this invention in an optically isotropic liquid crystal phase, an electric birefringence occurs but the Kerr effect does not necessarily occur.

Because the electric birefringence of an optically isotropic liquid crystal phase increases with the pitch, the electric birefringence can be increased by adjusting the species and content of the chiral dopant to increase the pitch, as long as other optical properties, such as, transmittance and diffraction wavelength, etc., could be satisfied.

4-4. Other Components

Other compounds, such as polymer material, may be further added into the optically isotropic liquid crystal composition of this invention, so long as they do not affect the properties of the composition. In addition to the polymer material, the liquid crystal composition of this invention can also contain, for example, a dichroic dye or a photochromic compound. Examples of the dichroic dye include merocyanine dyes, styryl dyes, azo dyes, azomethine dyes, azoxy dyes, quinophthalone dyes, anthraquinone dyes, tetrazine dyes and so on.

5. Optically Isotropic Polymer/Liquid Crystal Composite material

A fifth aspect of this invention is a composite material of a polymer and a liquid crystal composition containing the compound of formula (1) and a chiral dopant, which exhibits optical isotropy. The composite material is an optically isotropic polymer/liquid crystal composite material that can be used in an optical device driven in an optically isotropic liquid crystal phase. The scope of the optically isotropic polymer/liquid crystal composite material includes the polymer-stabilized blue phase of Non-Patent Reference 1 obtained by polymerizing a mixture of a monomer and a liquid crystal in blue phase, and a quasi-isotropic liquid crystal of Non-Patent Reference 2 obtained by polymerizing a mixture of a monomer and a liquid crystal in an isotropic phase. Such a polymer/liquid crystal composite material includes, for example, the liquid crystal composition of the above [1]-[30] (liquid crystal composition CLC) and a polymer.

The "polymer/liquid crystal composite material" of this invention has no particular limitation, as long as it is a composite containing both a liquid crystal material and a polymer, wherein the polymer may be partially or entirely not dissolved in the liquid crystal material, such that the polymer is separated from the liquid crystal material. Furthermore, in this specification, a nematic phase refers to one in narrow sense but does not include a chiral nematic phase, unless specifically indicated.

The optically isotropic polymer/liquid crystal composite material according to a preferred aspect of this invention can exhibit an optically isotropic liquid crystal phase in a wide temperature range. Moreover, the polymer/liquid crystal composite material according to a preferred aspect of this invention has very high response speed. Further, based on such effects, the polymer/liquid crystal composite material according to a preferred aspect of this invention is useful in an optical device such as a display device.

5-2. Polymer

Though the composite material of this invention can be produced by mixing an optically isotropic liquid crystal composition with a pre-polymerized polymer, it is preferably produced by mixing a low molecular-weight monomer, macromonomer, or oligomer, etc. (generally referred to as "monomers", hereinafter) of the polymer with the liquid crystal composition CLC and polymerizing the mixture. In this specification, the mixture containing the monomers and the liquid crystal composition is referred to as "polymerizable monomer/liquid crystal mixture", which may optionally contain a polymerization initiator, a curing agent, a catalyst, a stabilizer, a dichroic dye or a photochromic compound, etc., without compromising the effects of this invention. For example, the polymerizable monomer/liquid crystal mixture of this invention may also optionally contain 0.1-20 weight parts of a polymerization initiator relative to 100 weight parts of the polymerizable monomer.

The polymerization temperature is preferably such that the polymer/liquid crystal composite material exhibits high transparency and isotropy, and more preferably such that the mixture of the monomer and the liquid crystal material exhibits an isotropic phase or a blue phase, while the polymerization is carried out in the isotropic phase or optically isotropic liquid crystal phase. That is, the temperature is preferably set such that after the polymerization, the polymer/liquid crystal composite material substantially does not scatter light of wavelength longer than that of visible light and exhibits optical isotropy.

For example, a low molecular weight monomer, macromonomer or oligomer can be used as a raw material of the polymer for forming the composite material of this invention. In this specification, the raw material monomer of the polymer covers low molecular weight monomer, macromonomer and oligomer, etc. Further, the obtained polymer preferably has a 3D cross-linked structure, and thus the raw material monomer of the polymer is preferably a multi-functional monomer with 2 or more polymerizable functional groups. The polymerizable functional groups have no particular limitation, and include, for example, acryloyl, methacryloyl, glycidyl, epoxy, oxetanyl, vinyl, etc. In view of the polymerization rate, acryloyl and methacryloyl are preferred. It is preferred that the raw material monomer of the polymer contains 10 wt % or more of the monomer having two or more polymerizable functional groups, since such obtained composite material of this invention easily exhibits high transparency and isotropy.

Moreover, in order to obtain a preferred composite material, the polymer preferably has a mesogen moiety. A part or all of the raw material monomers of the polymer used can have a mesogen moiety.

5-2-1. Mono- and Di-functional Monomer Having Mesogen moiety

The mono- or di-functional monomer having a mesogen moiety has no particular limitation in structure, and can be, for example, a compound of formula (M1) or (M2).

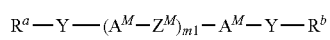  (M1)

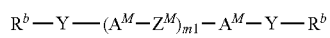  (M2)

(M3-1)

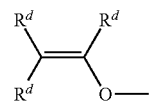

(M3-2)

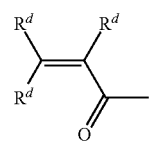

(M3-3)

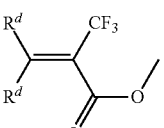

(M3-4)

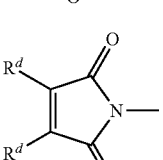

(M3-5)

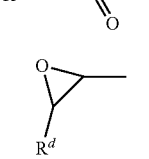

(M3-6)

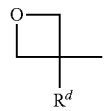

(M3-7)

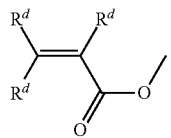

In formula (M1), the plural $R^a$ are independently hydrogen, halogen, —C≡N, —N=C=O, —N=C=S, or $C_{1-20}$ alkyl in which arbitrary —$CH_2$— may be substituted with —O—, —S—, —CO—, —COO—, —OCO—, —CH=CH—, —CF=CF— or —C≡C— and arbitrary hydrogen may be substituted with halogen or —C≡N. The plural $R^b$ are independently a polymerizable group selected from formulae (M3-1)-(M3-7).

Preferred examples of $R^a$ are hydrogen, halogen, —C≡N, —$CF_3$, —$CF_2H$, —$CFH_2$, —$OCF_3$, —$OCF_2H$, $C_{1-20}$ alkyl, $C_{1-19}$ alkoxy, $C_{2-21}$ alkenyl and $C_{2-21}$ alkynyl. More preferred examples of $R^a$ are —C≡N, $C_{1-20}$ alkyl and $C_{1-19}$ alkoxy.

In formula (M2), the plural $R^b$ are independently a polymerizable group selected from formulae (M3-1)-(M3-7).

In formulae (M3-1)-(M3-7), the plural $R^d$ are independently hydrogen, halogen, or $C_{1-5}$ alkyl in which arbitrary hydrogen may be substituted by halogen. Preferred examples of $R^d$ are hydrogen, halogen and methyl. More preferred examples of $R^d$ are hydrogen, fluorine and methyl.

Further, formulae (M3-2), (M3-3), (M3-4) and (M3-7) are preferably polymerized by free radical polymerization. Formulae (M3-1), (M3-5) and (M3-6) are preferably polymerized by cationic polymerization. The above polymerizations are all active polymerizations, and are initiated when a small amount of free radical or cationic active species is generated in the reaction system. In order to accelerate the generation of the active species, a polymerization initiator can be used. Light or heat can be used in order to generate the active species.

In formulae (M1) and (M2), the plural $A^M$ are independently aromatic or non-aromatic 5- or 6-membered ring or a fused ring of 9 or more carbons, and in the rings —$CH_2$— may be substituted with —O—, —S—, —NH— or —$NCH_3$—, —CH= may be substituted with —N= and hydrogen may be substituted with halogen, $C_{1-5}$ alkyl or $C_{1-5}$ haloalkyl. Specific examples of preferred $A^M$ are 1,4-cyclohexylene, 1,4-cyclohexenylene, 1,4-phenylene, naphthalene-2,6-diyl, tetrahydronaphthalene-2,6-diyl, fluorene-2,7-diyl or bicyclo[2.2.2]octan-1,4-diyl. In these rings, arbitrary —$CH_2$— may be substituted with —O—, arbitrary —CH= may be substituted with —N=, and arbitrary hydrogen may be substituted with halogen, $C_{1-5}$ alkyl or $C_{1-5}$ haloalkyl.

In consideration of the stability of the compound, —$CH_2$—O—$CH_2$—O— with oxygen not adjacent to one another is preferred to —$CH_2$—O—O—$CH_2$— with oxygen adjacent to one another. The same rule also applies to sulfur.

Among the rings, particularly preferred examples of $A^M$ are 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 2-trifluoromethyl-1,4-phenylene, 2,3-bis(trifluoromethyl)-1,4-phenylene, naphthalene-2,6-diyl, tetrahydronaphthalene-2,6-diyl, fluorene-2,7-diyl, 9-methylfluorene-2,7-diyl, 1,3-dioxan-2,5-diyl, pyridin-2,5-diyl and pyrimidin-2,5-diyl. Moreover, the stereo-configuration of 1,4-cyclohexyl and 1,3-dioxan-2,5-diyl is in the trans-form superior to in the cis-form.

Because 2-fluoro-1,4-phenylene and 3-fluoro-1,4-phenylene are identical in structure, the latter is not exemplified. This rule also applies to the relationship between 2,5-difluoro-1,4-phenylene and 3,6-difluoro-1,4-phenylene, etc.

In formulae (M1) and (M2), the plural Y are independently a single bond, or $C_{1-20}$ alkylene in which arbitrary —$CH_2$— may be substituted with —O—, —S—, —CH=CH—, —COO— or —COO—. Preferred examples of Y are single bond, —$(CH_2)_{m2}$—, —$O(CH_2)_{m2}$— and —$(CH_2)_{m2}O$—, wherein m2 is an integer of 1-20. Particularly preferred examples of Y are single bond, —$(CH_2)_{m2}$—, —$O(CH_2)_{m2}$— and —$(CH_2)_{m2}O$—, wherein m2 is an integer of 1-10. In consideration of the stability of the compound, —Y—$R^a$ and —Y—$R^b$ are preferably those not having —O—O—, —O—S—, —S—O— or —S—S—.

In formulae (M1) and (M2), the plural $Z^M$ are independently a single bond, —$(CH_2)_{m3}$—, —$O(CH_2)_{m3}$—, —$(CH_2)_{m3}O$—, —$O(CH_2)_{m3}O$—, —CH=CH—, —C≡C—, —COO—, —OCO—, —$(CF_2)_2$—, —$(CH_2)_2$COO—, —OCO—$(CH_2)_2$—, —CH=CH—COO—, —OCO—CH=CH—, —C≡C—COO—, —OCO—C≡C—, —CH=CH—$(CH_2)_2$—, —$(CH_2)_2$—CH=CH—, —CF=CF—, —C≡C—CH=CH—, —CH=CH—C≡C—, —$OCF_2$—$(CH_2)_2$—, —$(CH_2)_2$—$CF_2O$—, —$OCF_2$— or —$CF_2O$—, wherein m3 is an integer of 1-20.

Preferred examples of $Z^M$ are single bond, —$(CH_2)_{m3}$—, —$O(CH_2)_{m3}$—, —$(CH_2)_{m3}O$—, —CH=CH—, —C≡C—, —COO—, —OCO—, —$(CH_2)_2$—COO—, —OCO—$(CH_2)_2$—, —CH=CH—COO—, —OCO—CH=CH—, —$OCF_2$— and —$CF_2O$—.

In formulae (M1) and (M2), m1 is an integer of 1-6 and preferably an integer of 1-3. When m1 is 1, they are bicyclic compounds having two rings, for example, two 6-membered rings. When m1 is 2 or 3, they are tricyclic or tetracyclic compounds. For example, when m1 is 1, the two $A^M$ can be identical or different. Moreover, for example, when m1 is 2, the three $A^M$ (or two $Z^M$) can be identical or different. When m1 is 3-6, it is also the case. The case also applies to $R^a$, $R^b$, $R^d$, $Z^M$, $A^M$ and Y.

Even the compound (M1) of formula (M1) and the compound (M2) of formula (M2) containing an isotope in an amount higher than its natural abundance, such as $^2H$ (deuterium) and $^{13}C$, are useful, due to the identical properties.

More preferred examples of the compounds (M1) and (M2) are compounds (M1-1)-(M1-41) and (M2-1)-(M2-27) of formulae (M1-1)-(M1-41) and (M2-1)-(M2-27). In these compounds, $R^a$, $R^b$, $R^d$, $Z^M$, $A^M$, Y and p are defined as in the cases of formulae (M1) and (M2) in the above aspects of this invention.

Each partial structure of the compounds (M1-1)-(M1-41) and (M2-1)-(M2-27) is described as follows. The partial structure (a1) represents 1,4-phenylene in which arbitrary hydrogen atom is substituted by fluorine. The partial structure (a2) represents 1,4-phenylene in which arbitrary hydrogen may be substituted by fluorine. The partial structure (a3) represents 1,4-phenylene in which arbitrary hydrogen may be substituted with fluorine or methyl. The partial structure (a4) represents fluorenylene in which the hydrogen atom at position 9 may be substituted with methyl.

(a1)

(a2)

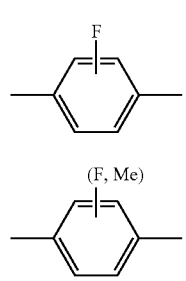
(a3)

(a4)

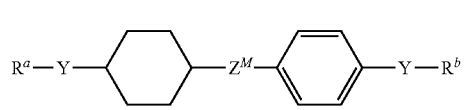
(M1-1)

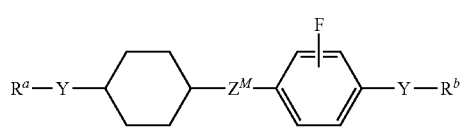
(M1-2)

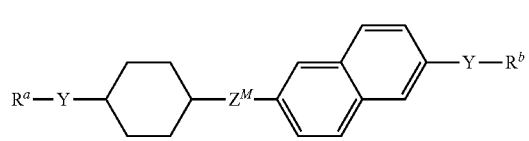
(M1-3)

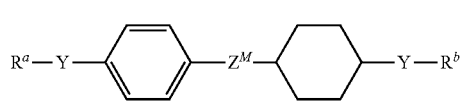
(M1-4)

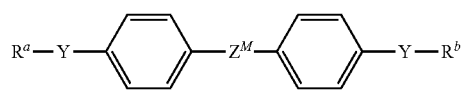
(M1-5)

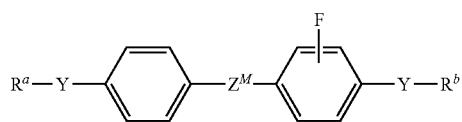
(M1-6)

(M1-7) 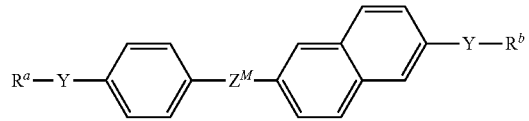
(M1-8) 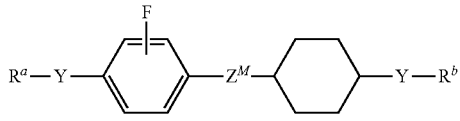
(M1-9) 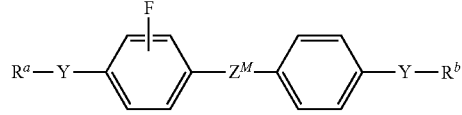
(M1-10) 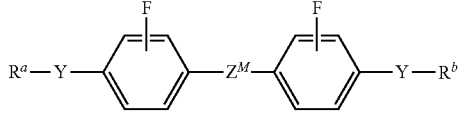
(M1-11) 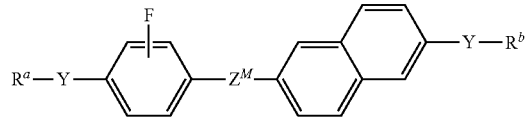
(M1-12) 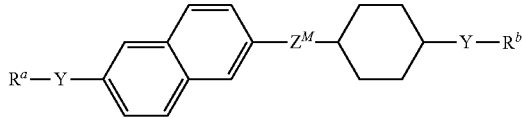
(M1-13) 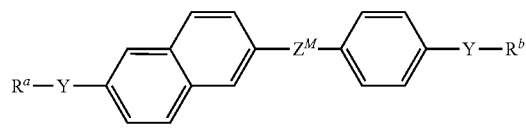
(M1-14) 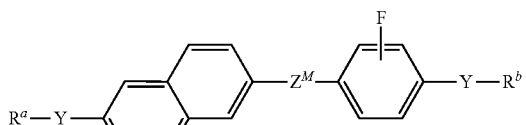
(M1-15) 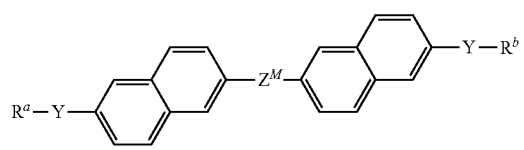
(M1-16) 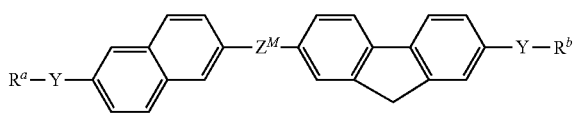
(M1-17) 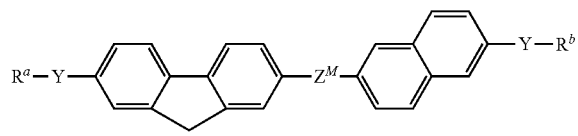
(M1-18) 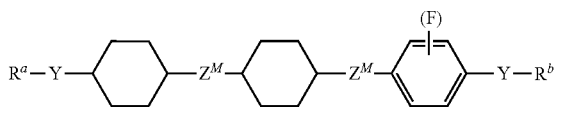
(M1-19) 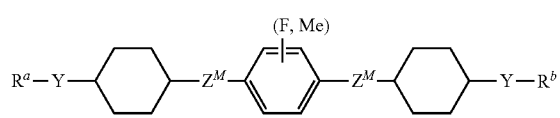
(M1-20) 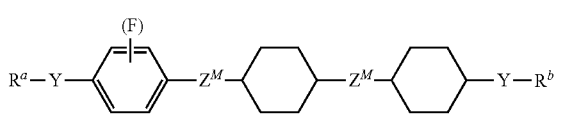
(M-21) 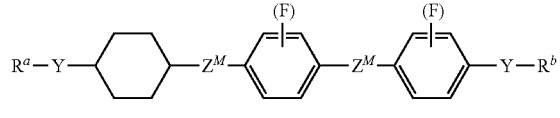
(M1-22) 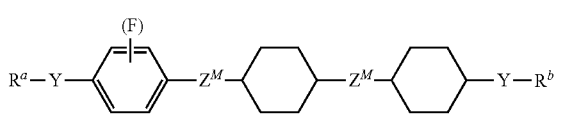
(M1-23) 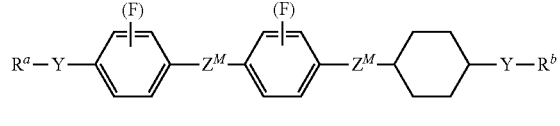
(M1-24) 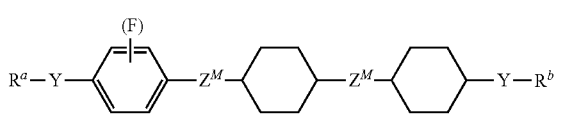
(M1-25) 
(M1-26) 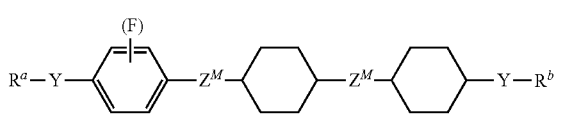

-continued
(M1-27)
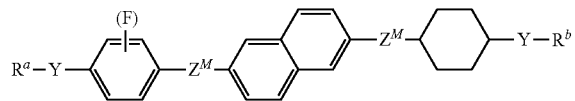
(M1-28)
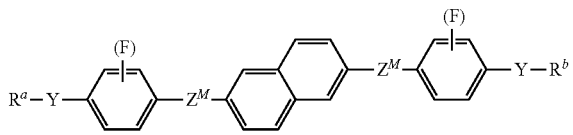
(M1-29)
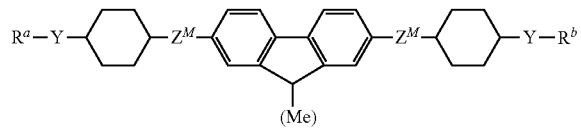
(M1-30)
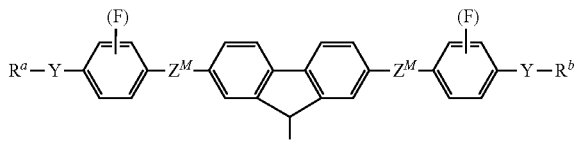
(M1-31)
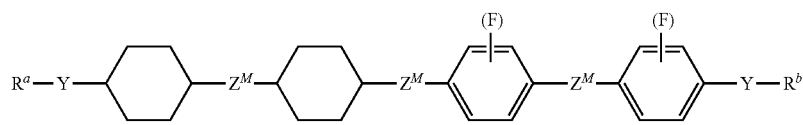
(M1-32)
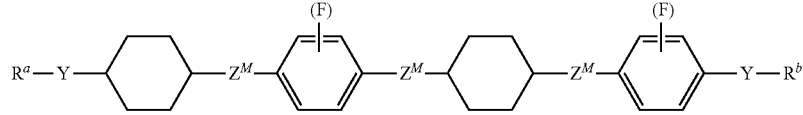
(M1-33)
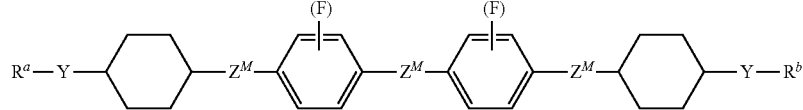
(M1-34)
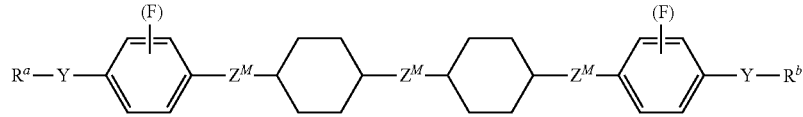
(M1-35)
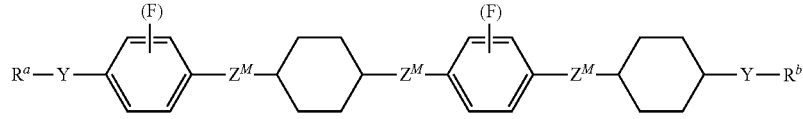
(M1-36)
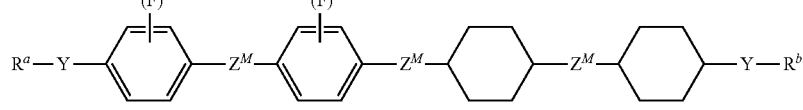
(M1-37)
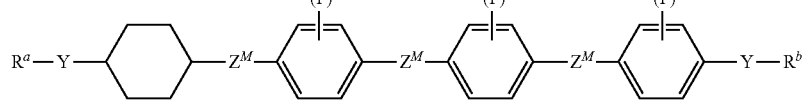
(M1-38)
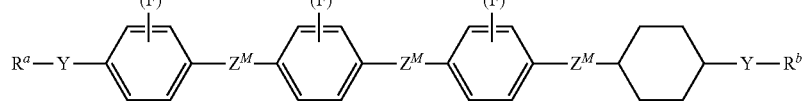
(M1-39)
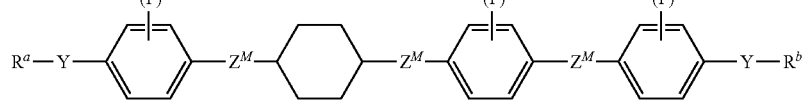

(M1-40) 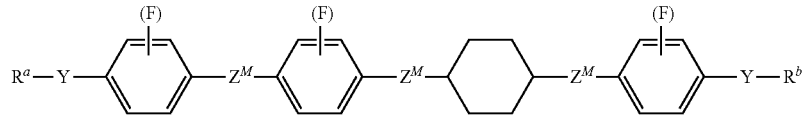
(M1-41) 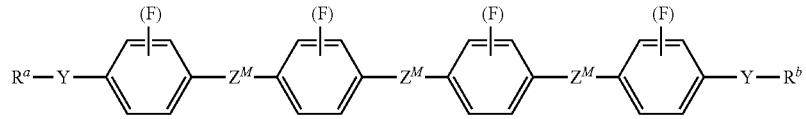
(M2-1) 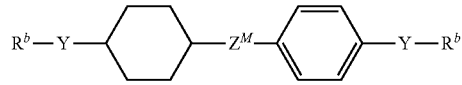
(M2-2) 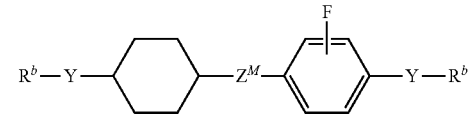
(M2-3) 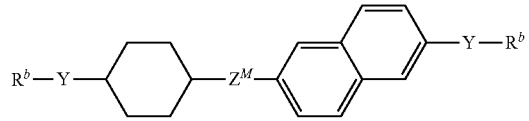
(M2-4) 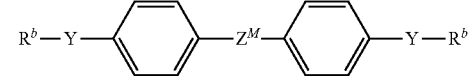
(M2-5) 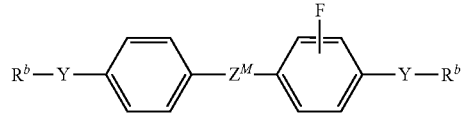
(M2-6) 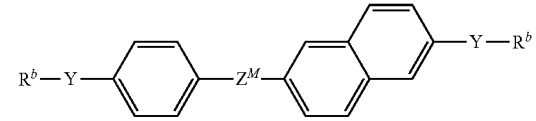
(M2-7) 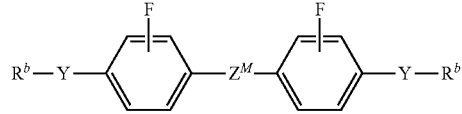
(M2-8) 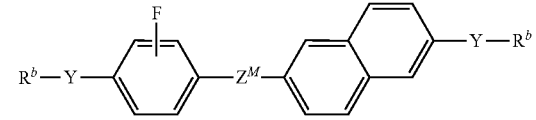
(M2-9) 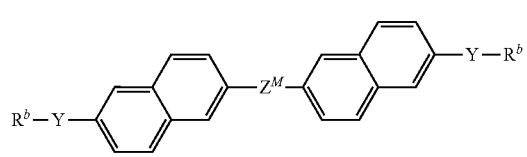
(M2-10) 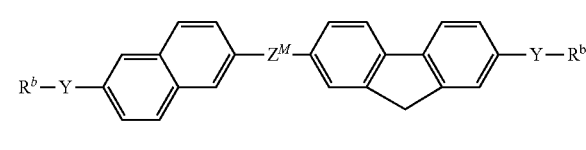
(M2-11) 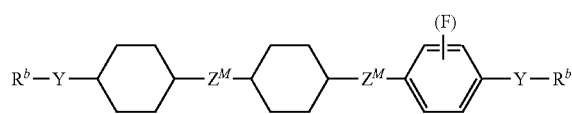
(M2-12) 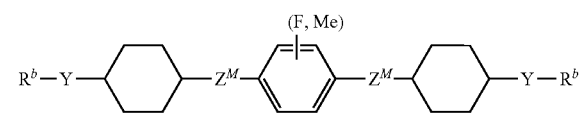
(M2-13) 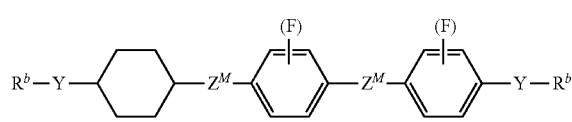
(M2-14) 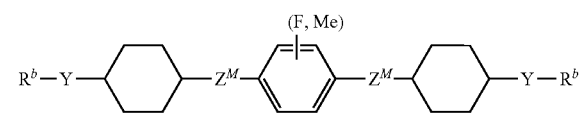
(M2-15) 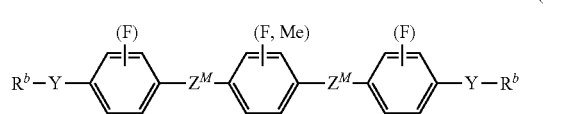
(M2-16) 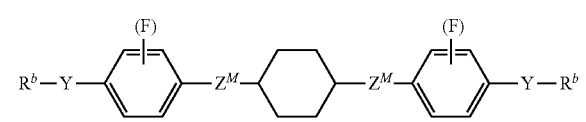
(M2-17) 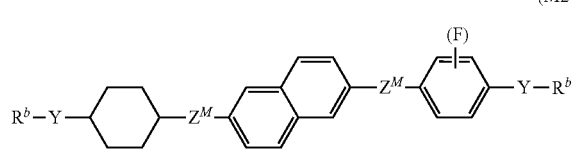
(M2-18) 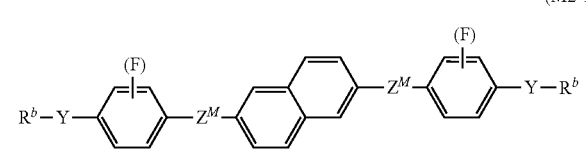

(M2-19)
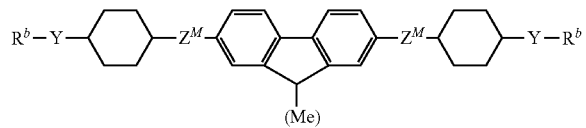

(M2-20)
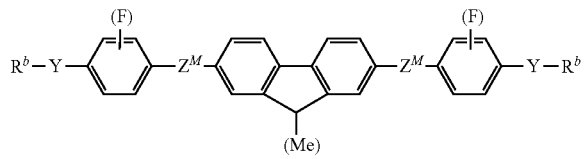

(M2-21)
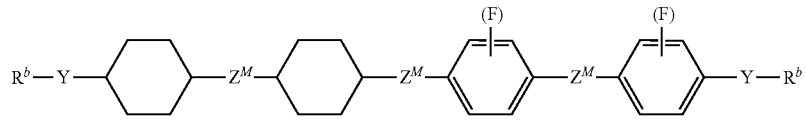

(M2-22)
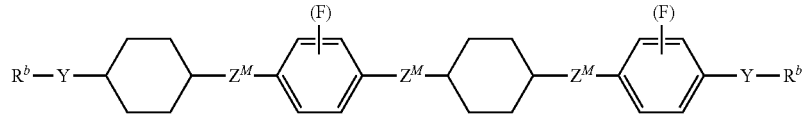

(M2-23)
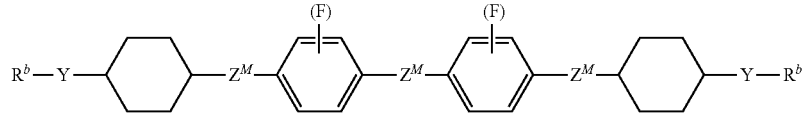

(M2-24)
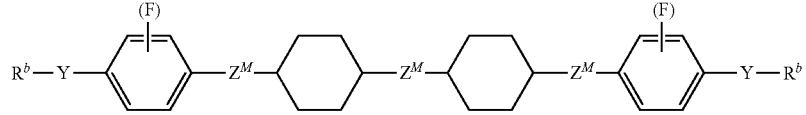

(M2-25)
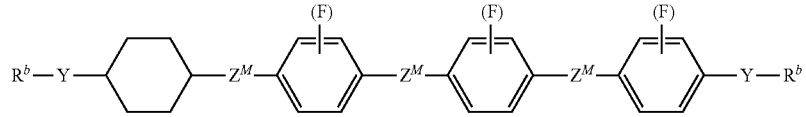

(M2-26)
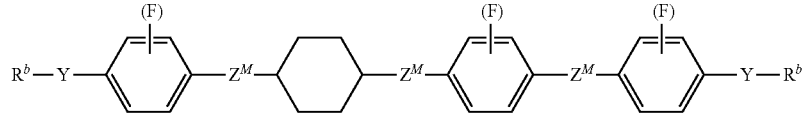

(M2-27)
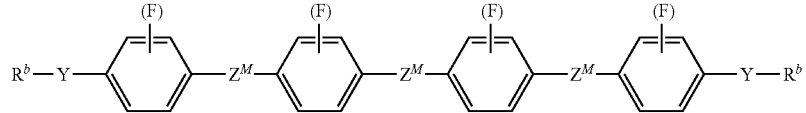

A monomer having no mesogen moiety and a polymerizable compound having a mesogen moiety other than the monomers (M1) and (M2) can be used, if required.

In order to optimize the optical isotropy of the polymer/liquid crystal composite material of this invention, a monomer having a mesogen moiety and three or more polymerizable groups can be used. The monomer having a mesogen moiety and three or more polymerizable groups is preferably a known compound, for example, (M4-1)-(M4-3), and more specifically, the compounds described in Japanese Patent Publication Nos. 2000-327632, 2004-182949 and 2004-59772. In (M4-1)-(M4-3), $R^b$, $Z^M$, Y and (F) are defined as above.

(M4-1)
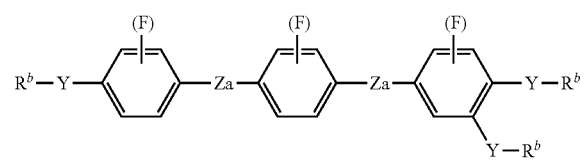

(M4-2)
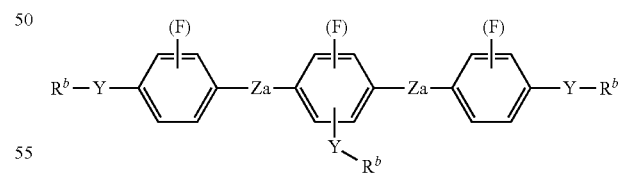

(M4-3)
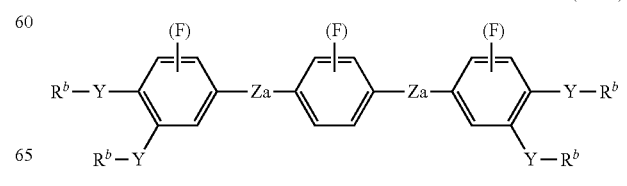

5-2-2. Monomer Having No Mesogen Moiety and Having Polymerizable Group

Examples of the monomer having no mesogen moiety and having a polymerizable group are linear or branched acrylates of 1-30 carbons, linear or branched diacrylates of 1-30 carbons, and monomers having three or more polymerizable groups, for example, but not limited to, glycerol propoxylate (1PO/OH)triacrylate, pentaerythritol propoxylate triacrylate, pentaerythritol triacrylate, trihydroxylmethylpropane ethoxylate triacrylate, trihydroxylmethylpropane propoxylate triacrylate, trihydroxylmethylpropane triacrylate, di(trihydroxylmethylpropane)tetraacrylate, pentaerythritol tetraacrylate, di(pentaerythritol)pentaacrylate, di(pentaerythritol) hexaacrylate and trihydroxylmethylpropane triacrylate.

5-2-3. Polymerization Initiator

The polymerization used to produce the polymer forming the composite material of this invention has no particular limitation, and can be, for example, photo-radical polymerization, thermo-radical polymerization and photo-cationic polymerization, etc.

Examples of the photo-radical polymerization initiator for photo-radical polymerization are DAROCUR™ 1173 and 4265 (both are trade names, from Ciba Specialty Chemicals), and IRGACURE™ 184, 369, 500, 651, 784, 819, 907, 1300, 1700, 1800, 1850 and 2959 (all are trade names, from Ciba Specialty Chemicals).

Preferred examples of the initiators causing radical polymerization with heating and being useful in thermo-radical polymerization are benzoyl peroxide, diisopropyl peroxydicarbonate, t-butyl peroxy(2-ethylhexanoate), t-butyl peroxypivalate, t-butyl peroxydiisobutyrate, lauroyl peroxide, dimethyl 2,2'-azobisisobutyrate (MAIB), di-t-butyl peroxide (DTBPO), azobisisobutyronitrile (AIBN) and azobiscyclohexanecarbonitrile (ACN), etc.

Examples of the photo-cationic polymerization initiator useful for photo-cationic polymerization are diaryliodonium salt (DAS) and triarylsulfonium salt (TAS), etc.

Examples of DAS are diphenyliodonium tetrafluoroborate, diphenyliodonium hexafluorophosphonate, diphenyliodonium hexafluoroarsenate, diphenyliodonium trifluoromesylate, diphenyliodonium trifluoroacetate, diphenyliodonium p-toluenesulfonate, diphenyliodonium tetrakis(pentafluorophenyl)borate, 4-methoxyphenylphenyliodonium tetrafluoroborate, 4-methoxyphenylphenyliodonium hexafluorophosphonate, 4-methoxyphenylphenyliodonium hexafluoro arsenate, 4-methoxyphenylphenyliodonium trifluoromesylate, 4-methoxyphenylphenyliodonium trifluoro acetate and 4-methoxyphenylphenyliodonium p-toluenesulfonate.

DAS can be sensitized by adding a photosensitizer, such as thioxanthone, phenothiazine, chlorothioxanthone, xanthone, anthracene, diphenyl anthracene and rubrene, etc.

Examples of TAS are triphenylsulfonium tetrafluoroborate, triphenylsulfonium hexafluorophosphonate, triphenylsulfonium hexafluoroarsenate, triphenylsulfonium trifluoromesylate, triphenylsulfonium trifluoroacetate, triphenylsulfonium p-toluenesulfonate, triphenylsulfonium tetrakis(pentafluorophenyl)borate, 4-methoxyphenyldiphenylsulfonium tetrafluoroborate, 4-methoxy phenyldiphenylsulfonium hexafluorophosphonate, 4-methoxyphenyldiphenylsulfonium hexafluoroarsenate, 4-methoxyphenyldiphenylsulfonium trifluoromesylate, 4-methoxyphenyldiphenylsulfonium trifluoroacetate, and 4-methoxyphenyldiphenylsulfonium p-toluenesulfonate, etc.

Specific examples of the photo-cationic polymerization initiator are Cyracure™ UVI-6990, Cyracure™ UVI-6974 and Cyracure™ UVI-6992 (all are trade names, from UCC Corporation), Adeka Optomer™ SP-150, SP-152, SP-170 and SP-172 (all are trade names, from ADEKA Corporation), Rhodorsil Photoinitiator™ 2074 (trade name, from RHODIA JAPAN Corporation), IRGACURE™ 250 (trade name, from Ciba Specialty Chemicals) and UV-9380C (trade name, from GE Toshiba Silicones Co. Ltd), etc.

5-2-4 Curing Agents and Other Components

In preparing the polymer forming the composite material of this invention, in addition to the monomers and polymerization initiator mentioned above, one or two or more other suitable component(s), for example, curing agent, catalyst and stabilizer, can be further added.

The latent curing agents known in the art and commonly used as epoxy resin curing agents can be used. Examples of the latent curing agents for epoxy resins are amine curing agents, Novolac curing agents, imidazole curing agents and anhydride curing agents, etc. Examples of the amine curing agents are aliphatic polyamines such as diethylenetriamine, triethylenetetraamine, tetraethylenepentaamine, m-xylenediamine, trimethyl hexamethylenediamine, 2-methyl hexamethylenediamine and diethylamino-propylamine; alicyclic polyamines such as isophorone diamine, 1,3-diaminomethylcyclohexane, bis(4-aminocyclohexyl)methane, norbornanediamine, 1,2-diamino-cyclohexane and Laromin; and aromatic polyamines such as diaminodiphenylmethane, diaminodiphenylethane and m-phenylenediamine, etc.

Examples of the Novolac curing agents are phenol-Novolac resin and bisphenol-Novolac resin, etc. Examples of the imidazole curing agents are 2-methylimidazole, 2-ethylhexylimidazole, 2-phenylimidazole and 1-cyanoethyl-2-phenylimidazolium trimellitate, etc.

Examples of the anhydride curing agents are tetrahydrophthalic anhydride, hexahydrophthalic anhydride, methyltetrahydrophthalic anhydride, methylhexahydrophthalic anhydride, methylcyclohexene tetracarboxylic dianhydride, phthalic anhydride, trimellitic anhydride, pyromellitic anhydride, and benzophenonetetracarboxylic dianhydride, etc.

Further, a curing promoter can further be used to facilitate the curing reaction of the curing agent and a polymerizable compound with glycidyl, epoxy or oxetanyl. Examples of the curing promoter are tertiary amines such as benzyldimethylamine, tris(dimethylaminomethyl)phenol, and dimethylcyclohexylamine; imidazoles such as 1-cyanoethyl-2-ethyl-4-methylimidazole and 2-ethyl-4-methylimidazole; organophosphorus compounds such as triphenylphosphine; quaternary phosphosium salts such as tetraphenylphosphosium bromide; diazobicyclo alkenes such as 1,8-diazobicyclo [5.4.0]undecene-7 and organic acid salts thereof; quaternary ammonium salts such as tetraethylammonium bromide and tetrabutylammonium bromide; boron compounds such as boron trifluoride and triphenyl borate, etc. These curing promoters can be used alone or in a combination of two or more.

Moreover, a stabilizer is preferably added to prevent undesired polymerization, for example, during storage. The stabilizer can be any compound known to those of ordinary skill in the art, and the representative examples thereof are 4-ethoxyphenol, hydroquinone and butylated hydroxytoluene (BHT), etc.

5-3. Content of Liquid Crystal Composition

The content of the liquid crystal composition in the polymer/liquid crystal composite material of this invention is preferably as high as possible, so long as it is within a range in which the composite material can exhibit an optically isotropic liquid crystal phase. This is due to the fact that the electric birefringence of the composite material of this invention is greater when the content of the liquid crystal composition is higher.

In the polymer/liquid crystal composite material of this invention, the content of the liquid crystal composition is preferably 60-99 wt %, more preferably 60-95 wt % and particularly preferably 65-95 wt %, relative to the composite material. The content of the polymer is preferably 1-40 wt %, more preferably 5-40 wt % and particularly preferably 5-35 wt %, relative to the composite material.

5-4. Other Components

The polymer/liquid crystal composite material of this invention can also contain, for example, a dichroic dye and a photochromic compound, without compromising the effects of this invention.

This invention is further described in detail with reference to examples, but is not limited thereto. Furthermore, "%" denotes "wt %", unless specifically indicated.

6. Optical Device

A sixth aspect of this invention is an optical device that contains the liquid crystal composition or the polymer/liquid crystal composite material (both sometimes collectively referred to as "liquid crystal medium", hereinafter,) and is driven in an optically isotropic liquid crystal phase.

The liquid crystal medium is optically isotropic in absence of an electric field and exhibits an optical anisotropy in presence of an electric field, such that optical modulation can be achieved with an electric field.

The structure of the LCD device is, for example, as shown in FIG. 1, in which the electrodes on the comb-like electrode substrate are structured such that the electrode 1 extending from the left side and the electrode 2 extending from the right side are alternatively arranged. When there is a potential difference between the electrode 1 and the electrode 2, the comb-like electrode substrate is provided with an electric field in two directions (upward and downward), as shown in FIG. 1.

EXAMPLES

The resulting compound is characterized by nuclear magnetic resonance (NMR) spectrum using $^1$H-NMR analysis and gas chromatogram obtained from gas chromatography (GC) analysis. The analysis methods are firstly described below.

$^1$H-NMR analysis: $^1$H-NMR analysis was carried out in DRX-500 (manufactured by Bruker BioSpin Co., Ltd). In the measurement, a sample prepared in an example was dissolved in a deuterated solvent, such as $CDCl_3$, capable of dissolving the sample, and then measured with a NMR apparatus at 500 MHz at room temperature in 24 times of accumulation. In the resulting NMR spectrum, "s" denotes singlet, "d" denotes doublet, "t" denotes triplet, "q" denotes quartet, and "m" denotes multiplet. Tetramethylsilane (TMS) was used as the standard of the chemical shift (δ) of zero.

GC analysis: GC analysis was carried out using a GC apparatus Model GC-14B (manufactured by Shimazu). The column was the capillary column CBP1-M25-025 (length=25 m, inner diameter=0.22 mm, film thickness=0.25 µm) made by Shimazu, and the stationary liquid phase was dimethylpolysiloxane (without polarity). The carrier gas was helium, and the flow rate was adjusted to 1 ml/min. The sample evaporation chamber was set at 300° C., and the detector (FID) was set at 300° C.

A sample was dissolved in toluene to give a solution of 1 wt %, and then 1 µl of the solution was injected into the sample evaporation chamber.

The recorder used was Chromatopac Model C-R6A (manufactured by Shimazu) or an equivalent thereof. The resulting gas chromatogram exhibited peak retention times and peak areas corresponding to the component compounds.

The solvent for diluting the sample was, for example, chloroform or hexane, etc. The column used was, for example, the capillary column DB-1 (length=30 m, inner diameter=0.32 mm, film thickness=0.25 µm, made by Agilent Technologies Inc.), HP-1 (length=30 m, inner diameter=0.32 mm, film thickness=0.25 µm, made by Agilent Technologies Inc.), Rtx-1 (length=30 m, inner diameter=0.32 mm, film thickness=0.25 µM, made by Restek Corporation) or BP-1 (length=30 m, inner diameter=0.32 mm, film thickness=0.25 µm, made by SGE International Pty. Ltd.).

The area ratio of the peaks in the gas chromatogram correspond to the ratio of the contents of the component compounds. Generally, the weight percentages of the component compounds in the analyzed sample are not completely identical to the area percentages of the peaks. However, in this invention, when the columns above are used, the correction coefficient is substantially 1. Therefore, the weight percentages of the component compounds in the analyzed sample are substantially equivalent to the area percentages of the peaks. This is because there is no significant difference among the correction coefficients of the component compounds. In order to more accurately calculate the ratios of the liquid crystal compounds in the liquid crystal composition with GC, the internal standard method for GC can be used. GC measurements were simultaneously performed on an accurately weighed specified amount of a liquid crystal compound component (detected component) and a liquid crystal compound as standard (standard), and the relative intensity was previously calculated as peak area ratio of the detected component to the standard. If a correction was done by using the relative intensity expressed as peak area ratio of each component to the standard, then the ratio of the contents of the liquid crystal compounds in the liquid crystal composition can be more accurately calculated with GC analysis.

Samples for Determining Characteristic Values of Liquid Crystal Compounds

Upon measuring the characteristic values of a liquid crystal compound, there are two methods, i.e., taking a pure compound as a sample, and mixing a compound in a mother liquid crystal to form a sample.

When a sample prepared by mixing a compound with a mother liquid crystal is measured, the following method is used for the measurement. Firstly, the resulting liquid crystal compound was mixed with the mother liquid crystal in a ratio of 15 wt %:85 wt % to prepare a sample, and then the characteristic value of the compound is calculated from the measured value obtained with the extrapolation method expressed by the equation below.

[Extrapolated Value]=(100×[measured value of the sample]−[wt % of the mother liquid crystal]×[measured value of the mother liquid crystal])/[wt % of the liquid crystal compound]

While a smectic phase or a crystal was deposited at the above ratio of the liquid crystal compound to the mother liquid crystal at 25° C., the ratio of the liquid crystal compound to the mother liquid crystal is changed to 10 wt %:90 wt %, 5 wt %:95 wt %, 1 wt %:99 wt % in order. The composition without deposition of a smectic phase or a crystal at 25° C. was measured for characteristic values, and the characteristic values of the liquid crystal compound is further calculated by the extrapolation method expressed by the equation above.

There are numerous mother liquid crystals that can be used for the measurement. For example, the composition of the mother liquid crystal A is as follows (in wt %).
Mother Liquid Crystal A:

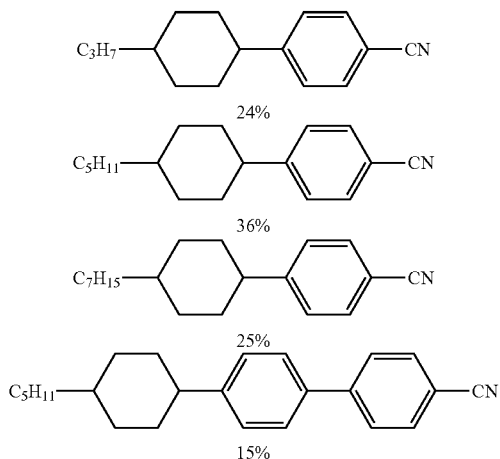

Method for Measuring Characteristic Values of Liquid Crystal Compounds

The measurement of the characteristic values was carried out with the methods below. These methods are mainly those described in EIAJ•ED-2521A of the Standard of Electric Industries Association of Japan, or modifications of the same. Moreover, the TN device used in the measurement was not equipped with TFT.

With respect to the determined values, in case that the liquid crystal compound itself is used as a sample, the obtained values are recorded as experimental data. In case that a mixture of the liquid crystal compound and a mother liquid crystal is used as a sample, the extrapolated values obtained with the extrapolation method are recorded as experimental data.

The phase structure and the phase transition temperature (° C.) were measured using the methods (1) and (2) below.

(1) A compound was placed on a hot plate (Hot Stage, Model FP-52, made by Mettler, Corp.) in a melting point measuring apparatus equipped with a polarization microscope, and the phase behavior and its change were observed by the polarization microscope while the sample was heated at a rate of 3° C./min, to determine the type of the liquid crystal phase.

(2) A scanning calorimetry DSC-7 system or Diamond DSC system (made by Perkin-Elmer Corp.) was used, at a heating or cooling rate of 3° C./min, and the on-set temperature of the endothermic peak or the exothermic peak accompanying with the phase change of the sample was calculated with the extrapolation method, so as to determine the phase transition temperature.

Hereinafter, crystal is expressed by K. In a case where two types of crystals are to be distinguished from each other, they are expressed by $K_1$ and $K_2$. A smectic phase is expressed by Sm, a nematic phase is expressed by N, and a liquid (isotropic phase) is expressed by I. In case that a smectic B phase and a smectic A phase are distinguished from each other in the smectic phase, they are expressed by SmB and 5 mA. BP represents a blue phase or an optically isotropic liquid crystal phase. Biphase co-existence is often expressed by (N*+I) or (N*+BP). Specifically, (N*+I) represents a phase in which an isotropic phase and a chiral nematic phase coexist, and (N*+BP) represents a phase in which a BP phase or an optically isotropic liquid crystal phase and a chiral nematic phase coexist. "Un" represents a non-optically isotropic unidentified phase. For the expression of the phase transition temperatures, for example, "K 50.0 N 100.0 I" means that the phase transition temperature (KN) from the crystal to the nematic phase is 50.0° C. and the phase transition temperature (NI) from the nematic phase to the liquid is 100.0° C. This also applies to other expressions.

The upper-limit temperature of a nematic phase ($T_{NI}$, ° C.): a sample (a mixture of a liquid crystal compound and a mother liquid crystal) was placed on a hot plate (Hot Stage, Model FP-52, made by Mettler Corp.) in a melting point measuring apparatus equipped with a polarization microscope, and observed by the polarization microscope while the sample was heated at a rate of 1° C./min. The temperature at which a part of the sample started to change from a nematic phase to an isotropic liquid was recorded as the upper-limit temperature of the nematic phase, which is sometimes abbreviated to "upper-limit temperature" below.

Low-temperature compatibility: samples were prepared by mixing a mother liquid crystal with a liquid crystal compound in a manner such that the contents of the latter were 20 wt %, 15 wt %, 10 wt %, 5 wt %, 3 wt % and 1 wt %, respectively, and then placed into glass bottles. The glass bottles were kept in a freezer at −10° C. or −20° C. for a certain period of time, and presence or absence of a crystal or a smectic phase was observed for each sample.

Viscosity (η, determined at 20° C., mPa·s): the viscosity of a mixture of a liquid crystal compound and a mother liquid crystal is measured using an E-type viscometer.

Optical anisotropy (Δn): the measurement was carried out at 25° C. by using light of 589 nm, with an Abbe refractometer having a polarizing plate mounted on the ocular lens. After the surface of the main prism is rubbed in a direction, a sample (a mixture of a liquid crystal compound and a mother liquid crystal) was dripped onto the main prism. The refractive index $n_\parallel$ was determined when the polarizing direction was paralleled to the rubbing direction, and the refractive index $n_\perp$ was determined when the polarizing direction was perpendicular to the rubbing direction. The value of the optical anisotropy (Δn) was calculated according to the equation "$\Delta n = n_\parallel - n_\perp$".

Dielectric anisotropy (Δ∈, determined at 25° C.): a sample (a mixture of a liquid crystal compound and a mother liquid crystal) was injected into a liquid crystal cell with a distance (cell gap) of about 9 μm between two glass substrates and a twist angle of 80°. The liquid crystal cell was applied with a voltage of 20 V, and the dielectric constant ∈$_\parallel$ in the major-axis direction of the liquid crystal molecule was determined. Then, a voltage of 0.5 V was applied and the dielectric constant ∈$_\perp$ in the minor-axis direction of the liquid crystal molecule was determined. The value of the dielectric anisotropy was calculated according to the equation "Δ∈=∈$_\parallel$−∈$_\perp$".

Pitch (p, determined at 25° C., m): a pitch length was measured with selective reflection (Handbook of Liquid Crystal, p. 196, 2000, Maruzen). For the selective reflection wavelength λ, the relationship <n>p/λ=1 exists, wherein <n> denotes the average refractive index and can be calculated from the equation $<n>=\{(n_\parallel^2+n_\perp^2)/2\}^{1/2}$. The selective reflection wavelength was determined by a microspectrophotometer MSV-350 made by Japan Electronics Co., Ltd. The pitch was calculated by dividing the resulting reflection wavelength with the average refractive index <n>. When the concentration of the optically active compound is low, the pitch of a cholesteric liquid crystal having a reflection wavelength at the long wavelength side of visible light is proportional to the reciprocal of the concentration. Therefore, multiple points were measured in the pitch length of the liquid crystal having a selective reflection wavelength in the visible light region, and then the pitch was calculated by using a linear extrapolation method. The "optically active compound" is equivalent to the chiral dopant in this invention.

Example 1

Synthesis of Compound (S1-9)

Compound (S1-9) is a compound of formula (1-2A) in which $R^1$ is $C_3H_7$, $L^2$, $L^4$ and $L^5$ are all fluorine and $X^1$ is fluorine.

K 69.6 I (° C.)

The synthesis scheme is shown below.

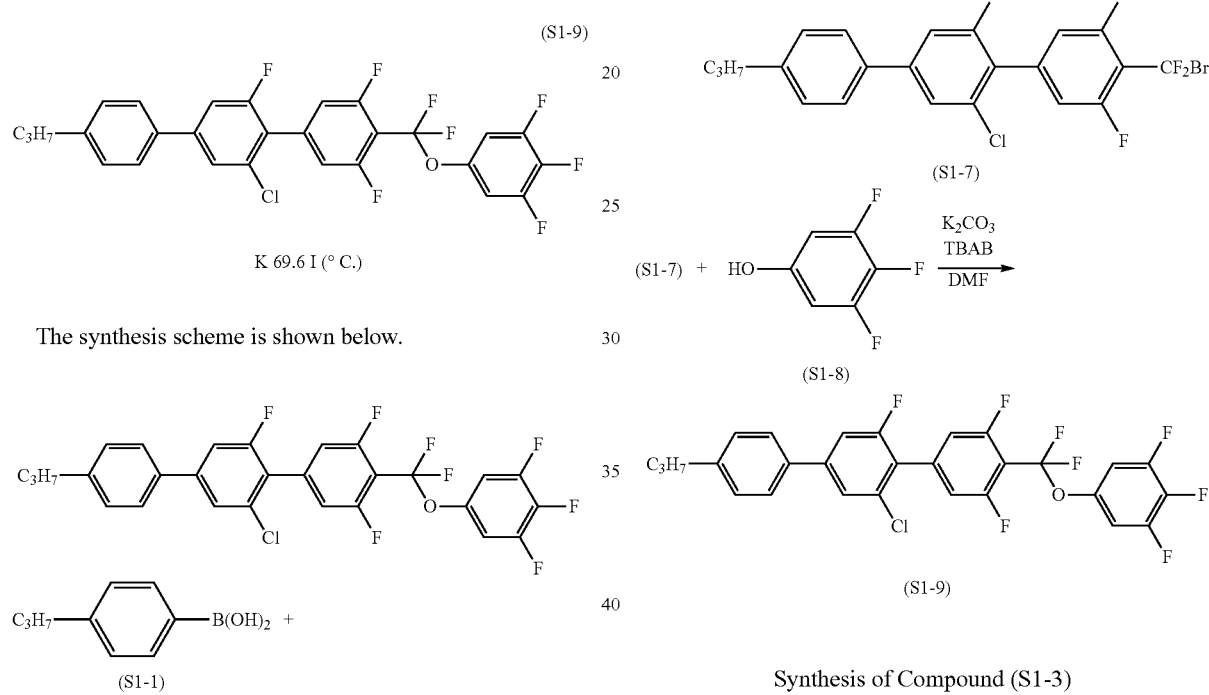

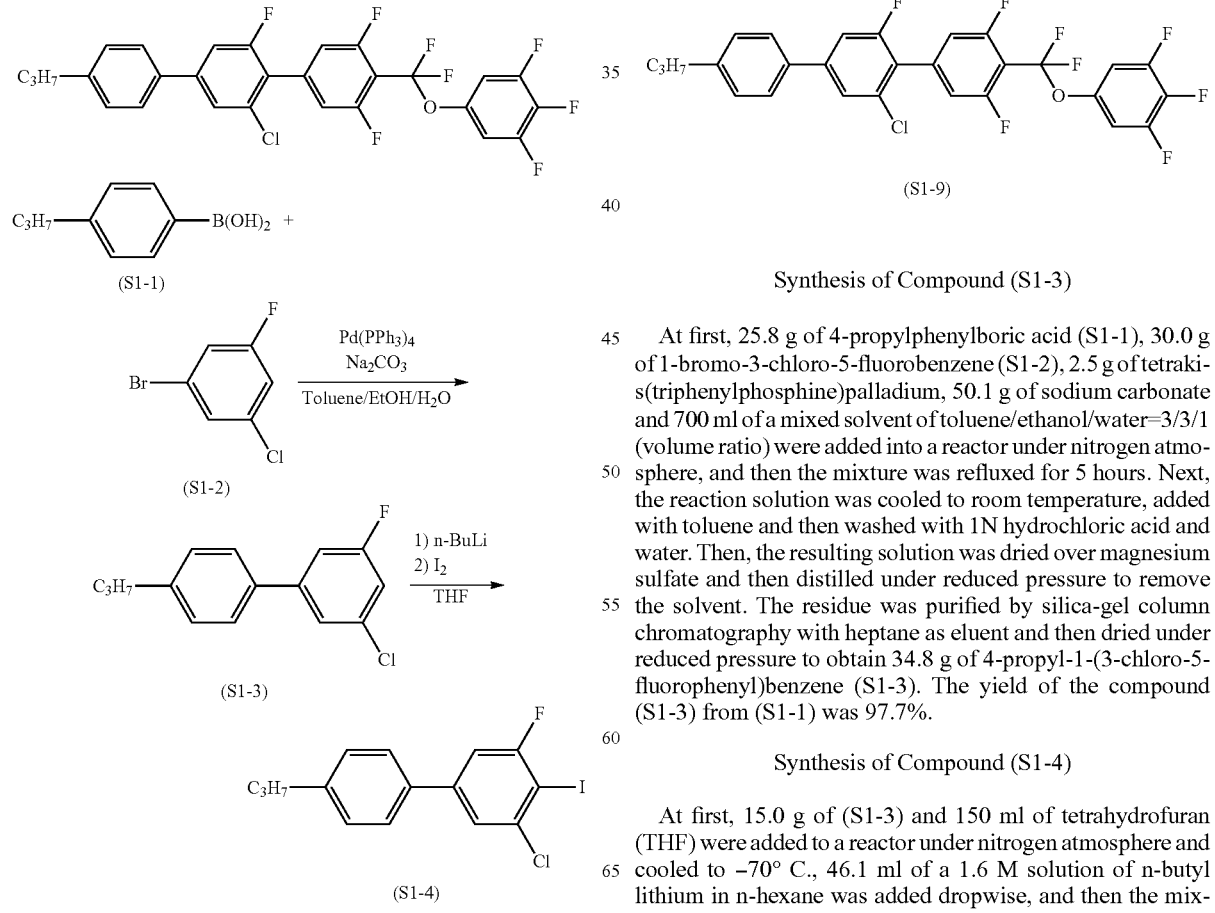

Synthesis of Compound (S1-3)

At first, 25.8 g of 4-propylphenylboric acid (S1-1), 30.0 g of 1-bromo-3-chloro-5-fluorobenzene (S1-2), 2.5 g of tetrakis(triphenylphosphine)palladium, 50.1 g of sodium carbonate and 700 ml of a mixed solvent of toluene/ethanol/water=3/3/1 (volume ratio) were added into a reactor under nitrogen atmosphere, and then the mixture was refluxed for 5 hours. Next, the reaction solution was cooled to room temperature, added with toluene and then washed with 1N hydrochloric acid and water. Then, the resulting solution was dried over magnesium sulfate and then distilled under reduced pressure to remove the solvent. The residue was purified by silica-gel column chromatography with heptane as eluent and then dried under reduced pressure to obtain 34.8 g of 4-propyl-1-(3-chloro-5-fluorophenyl)benzene (S1-3). The yield of the compound (S1-3) from (S1-1) was 97.7%.

Synthesis of Compound (S1-4)

At first, 15.0 g of (S1-3) and 150 ml of tetrahydrofuran (THF) were added to a reactor under nitrogen atmosphere and cooled to −70° C., 46.1 ml of a 1.6 M solution of n-butyl lithium in n-hexane was added dropwise, and then the mixture was stirred for 1 hour at the temperature. Next, 100 ml of a solution of 8.4 g iodine in THF was added dropwise at −70° C., and the mixture was stirred for 5 hr at the temperature. Afterwards, the reaction solution was warmed to room temperature, and poured into an aqueous sodium thiosulfate solution. Then, the product was extracted with ethyl acetate, and the organic layer was washed with an aqueous sodium thiosulfate solution and water. Next, the organic layer was dried over magnesium sulfate and distilled under reduced pressure to remove the solvent. Afterwards, the product was purified by silica-gel column chromatography with a mixed solution of heptane/toluene=3/1 as eluent, and then dried under reduced pressure, to obtain 22.4 g of 4-propyl-1-(3-chloro-5-fluoro-4-iodophenyl)benzene (S1-4). The yield of compound (S1-4) from (S1-3) was 99.3%.

Synthesis of Compound (S1-6)

At first, 22.3 g of (S1-4), 10.3 g of 3,5-difluorophenylboric acid (S1-5), 1.0 g of tetrakis(triphenylphosphine)palladium, 20.8 g of sodium carbonate and 490 ml of a mixed solvent of toluene/ethanol/water=3/3/1 (volume ratio) were added into a reactor under nitrogen atmosphere, and then the mixture was refluxed for 10 hours. Then, additional 1.0 g of tetrakis(triphenylphosphine)palladium was added, and the mixture was refluxed for another 10 hours. Next, the reaction solution was cooled to room temperature, added with toluene and then washed with 1N hydrochloric acid and water. Afterwards, the solution was dried over magnesium sulfate and distilled under reduced pressure to remove the solvent. Then, the product was purified by silica-gel column chromatography with heptane as eluent and dried under reduced pressure to obtain 24.9 g of 4-propyl-1-(3-chloro-5-fluorophenyl)benzene (S1-6). The yield of the compound (S1-6) from (S1-4) was 91.1%.

Synthesis of Compound (S1-7)

At first, 15.0 of the compound (S1-6) and 150 ml of THF were added in a reactor under nitrogen atmosphere, and then the mixture was cooled to −74° C. Next, 31.8 ml of 1.60 M solution of n-butyl lithium in n-hexane was added dropwise at a temperature ranging from −74° C. to −60° C., and the mixture was stirred for 60 min. Afterwards, 20.0 ml of a solution of 12.2 g dibromodifluoromethane in THF was added dropwise at a temperature ranging from −75° C. to −70° C., and the mixture was warmed to 25° C. and stirred for 60 min. Then, the reaction mixture was poured into 150 ml of ice water and mixed. Then, the mixture was extracted by adding 100 ml of toluene and separating the organic layer from the aqueous layer, and the organic layer was washed with saline and dried over anhydrous magnesium sulfate. The resulting solution was concentrated under reduced pressure, and then the residue was separated by silica-gel column chromatography with a mixed solvent of heptane/toluene=4/1 as an eluent. Next, the solution was distilled to remove the solvent and then dried to obtain 19.4 g of (S1-7).

Synthesis of Compound (S1-9)

At first, 6.0 g of the compound (S1-7), 1.5 g of 3,4,5-trifluorophenol (S1-8), 2.8 g of potassium carbonate and 100 ml of N,N-dimethylformamide (DMF) were added into a reactor under nitrogen atmosphere, and the mixture was stirred at 90° C. for 120 min. After being cooled to 25° C., the reaction mixture was poured into 50 ml of ice water and mixed. Next, the mixture was extracted by adding 100 ml of toluene and separating the organic layer from the aqueous layer. The resulting organic layer was sequentially washed with saturated aqueous sodium bicarbonate solution, 0.5 N aqueous sodium hydroxide solution and saline, and then dried over anhydrous magnesium sulfate. The resulting solution was concentrated under reduced pressure, and then the residue was separated by silica-gel column chromatography with heptane as the eluent. Next, the product was further purified by recrystallization in a mixed solvent of heptane/Solmix A-11 and dried to obtain 2.2 g of (S1-9). The yield of (S1-9) from (S1-6) was 30.6%.

The phase transition temperature (° C.) of the compound (S1-9) is: K 69.6 I.

The resulting compound was identified as (S1-9) from the following chemical shift (δ, in ppm) data obtained with $^1$H-NMR analysis in which $CDCl_3$ was used as a solvent: 7.55 (m, 1H), 7.51 (d, 2H), 7.33 (dd, 1H), 7.30 (d, 2H), 7.10 (d, 2H), 7.03-7.00 (m, 2H), 2.66 (t, 2H), 1.73-1.64 (m, 2H) and 0.98 (t, 3H).

Physical Properties of Liquid Crystal Compound (S1-9)

The four compounds designated as the above mother liquid crystal A were mixed to prepare the mother liquid crystal A having a nematic phase and the following physical properties: Upper-limit temperature $(T_{NI})$=71.7° C., $\Delta\epsilon$=11.0 and $\Delta n$=0.137.

Then, a liquid crystal composition B containing the mother liquid crystal A and (S1-9) obtained in Example 1 in a ratio of 85 wt % to 15 wt % was prepared, and the characteristic values were measured. The extrapolated characteristic values of (S1-9) calculated based on the measurements using the extrapolation method are as follows: $T_{NI}$=29.0° C., $\Delta\epsilon$=44.4 and $\Delta n$=0.150.

It is clear from the results that the liquid crystal compound (S1-9) is well compatible with other liquid crystal compounds and has a large dielectric anisotropy ($\Delta\epsilon$) and a large optical anisotropy ($\Delta n$).

Example 2

Synthesis of Compound (S2-2)

Compound (S2-2) is a compound of formula (1-2A) in which $R^1$ is $C_3H_7$, $L^2$, $L^4$ and $L^5$ are all fluorine and $X^1$ is —$CF_3$.

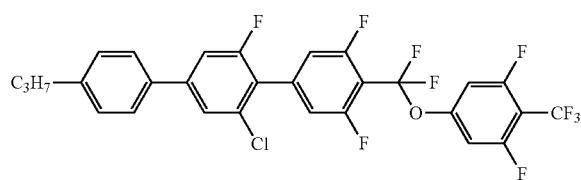

(S2-2)

K 98.9 I (° C.)

Synthesis of Compound (S2-2)

Synthesis of (S2-2) from (S1-6) was accomplished in a process similar to that for synthesizing (S1-9) from (S1-6) in Example 1, except that 3,5-difluoro-4-trifluoro-methylphenol (S2-1) was used instead of (S1-8). The yield of (S2-2) from (S1-6) was 27.2%. The phase transition temperature (° C.) of the compound (S2-2) is: K 98.9 I.

The resulting compound was identified as (S2-2) from the following chemical shift (δ, in ppm) data obtained with $^1$H-NMR analysis in which $CDCl_3$ was used as a solvent: 7.55

(m, 1H), 7.50 (d, 2H), 7.33 (dd, 1H), 7.30 (d, 2H), 7.10 (d, 2H), 7.01 (d, 2H), 2.66 (t, 2H), 1.72-1.67 (m, 2H) and 0.98 (t, 3H).

Physical Properties of Liquid Crystal Compound (S2-2)

The four compounds designated as the above mother liquid crystal A were mixed to prepare the mother liquid crystal A having a nematic phase. The physical properties of the mother liquid crystal A are as follows: $T_{NI}$=71.7° C., $\Delta\varepsilon$=11.0 and $\Delta n$=0.137.

Then, a liquid crystal composition C containing the mother liquid crystal A and (S2-2) obtained in Example 2 in a ratio of 95 wt % to 5 wt % was prepared, and the characteristic values were measured. The extrapolated characteristic values of (S2-2) calculated based on the measurements using the extrapolation method are as follows: $T_{NI}$=33.7° C., $\Delta\varepsilon$=57.7 and $\Delta n$=0.157.

It is clear from the results that the liquid crystal compound (S2-2) has a very large dielectric anisotropy ($\Delta\varepsilon$).

Example 3

Synthesis of Compound (S3-4)

Compound (S3-4) is a compound of formula (1-1B) in which $R^1$ is $C_3H_7$, $L^2$, $L^3$, $L^4$ and $L^5$ are all fluorine and $X^I$ is fluorine.

and 1100 ml of a mixed solvent of dimethoxyethane/water=2/1 (volume ratio) were added into a reactor under nitrogen atmosphere, and the mixture was heated to 80° C. and stirred for 4 hr. Next, the reaction solution was cooled to room temperature, added with toluene and then washed with 1N hydrochloric acid and water. Afterwards, the solution was dried over magnesium sulfate and distilled under reduced pressure to remove the solvent. Subsequently, the product was purified by silica-gel column chromatography with a mixed solvent of heptane/ethyl acetate=4/1 as the eluent and then dried under reduced pressure. The obtained residue was recrystallized in heptane to obtain 77.5 g of 3-fluoro-4-(3,4,5-trifluorophenyl)phenol (S3-3). The yield of (S3-3) from (S3-1) was 81.5%.

Synthesis of Compound (S3-4)

Synthesis of (S3-4) from (S1-6) was accomplished in a process similar to that for synthesizing (S1-9) from (S1-6) in Example 1, except that 3-fluoro-4-(3,4,5-trifluoro-phenyl)phenol (S3-3) was used instead of (S1-8). The yield of (S3-4) from (S1-6) was 31.4%. The phase transition temperature (° C.) of (S3-4) is: K 128.3 N 161.1 I.

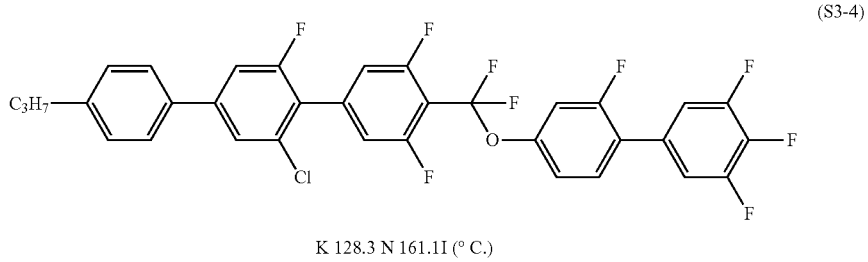

(S3-4)

K 128.3 N 161.1I (° C.)

The synthesis scheme is shown below.

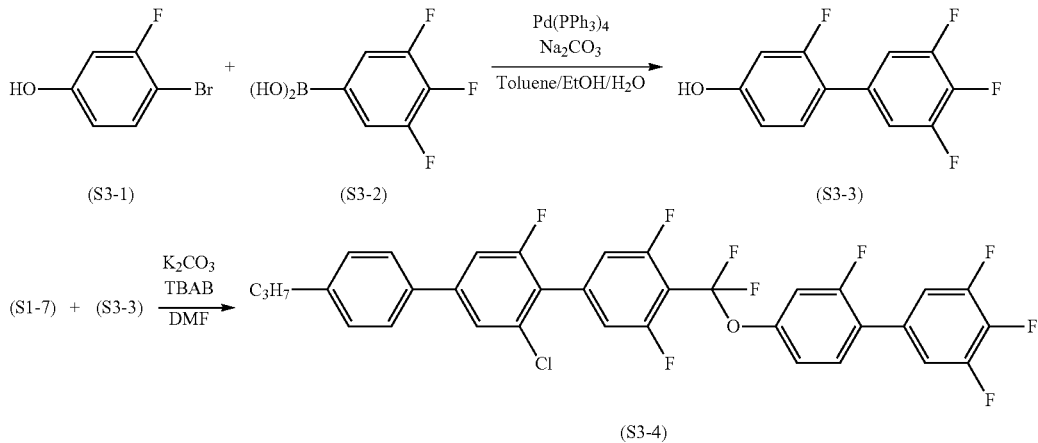

Synthesis of Compound (S3-3)

At first, 75.0 g of 4-bromo-3-fluorophenol (S3-1), 82.9 g of 3,4,5-trifluorophenyl-boric acid (S3-2), 13.6 g of tetrakis(triphenylphosphine)palladium, 108.5 g of sodium carbonate The resulting compound was identified as (S3-4) from the following chemical shift ($\delta$, in ppm) data obtained with $^1$H-NMR analysis in which CDCl$_3$ was used as a solvent: 7.55 (m, 1H), 7.51 (d, 2H), 7.39 (t, 1H), 7.33 (dd, 1H), 7.30 (d, 2H), 7.22-7.16 (m, 4H), 7.10 (d, 2H), 2.65 (t, 2H), 1.71-1.67 (m, 2H) and 0.98 (t, 3H).

115

Physical Properties of Liquid Crystal Compound (S3-4)

A liquid crystal composition D containing the mother liquid crystal A and (S3-4) obtained in Example 3 in a ratio of 95 wt % to 5 wt % was prepared, and the characteristic values were measured. The extrapolated characteristic values of (S3-4) calculated based on the measurements using the extrapolation method are as follows: $T_{NI}$=83.7° C., $\Delta\in$=47.7 and $\Delta n$=0.197.

It can be seen from the results that the liquid crystal compound (S3-4) has a high upper-limit temperature ($T_{NI}$), a large dielectric anisotropy ($\Delta\in$) and a large optical anisotropy ($\Delta n$).

Reference Example 1

Synthesis of Compound (S4-4)

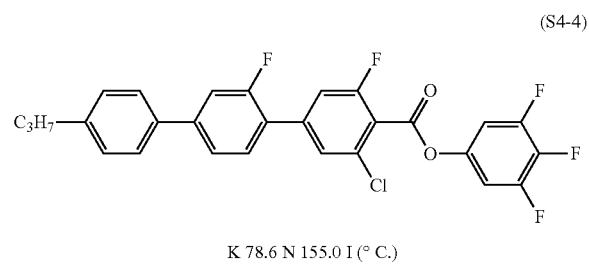

K 78.6 N 155.0 I (° C.)

The synthesis scheme is shown below.

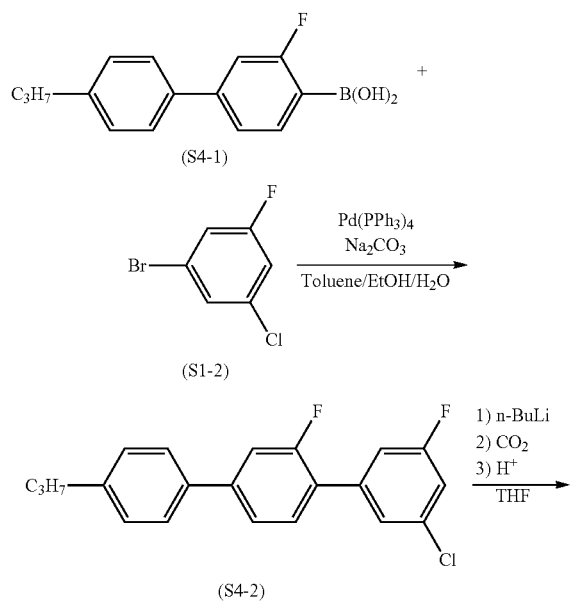

116

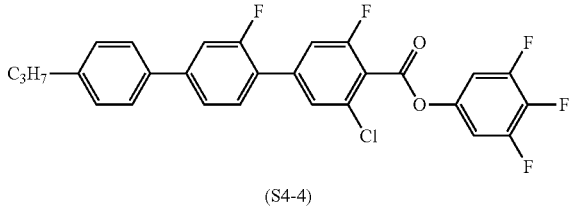

Synthesis of Compound (S4-2)

At first, 55.0 g of 4-(4-propylphenyl)-2-fluorophenylboric acid (S4-1), 40.6 g of 1-bromo-3-chloro-5-fluorobenzene (S1-2), 3.4 g of tetrakis(triphenylphosphine)-palladium, 67.8 g of sodium carbonate and 900 ml of a mixed solvent of toluene/ethanol/water=3/3/1 (volume ratio) were added into a reactor under nitrogen atmosphere, and the mixture was refluxed for 6 hr. Next, the reaction solution was cooled to room temperature, added with toluene and then washed with 1N hydrochloric acid and water. Afterwards, the solution was dried over magnesium sulfate and distilled under reduced pressure to remove the solvent. Then, the product was purified by silica-gel column chromatography with heptane as the eluent and then dried under reduced pressure. The obtained residue was recrystallized in a mixed solvent of ethanol/ethyl acetate=10/1, to obtain 47.7 g of (S4-2). The yield of (S4-2) from (S4-1) was 71.9%.

Synthesis of Compound (S4-3)

At first, 10.0 g of (S4-2) and 100 ml of THF were added into a reactor under nitrogen atmosphere and cooled to −74° C. Next, 22.3 ml of a 1.60 M solution of n-butyl lithium in n-hexane was added dropwise at a temperature ranging from −74° C. to −60° C., and the mixture was stirred for 60 min. Then, 6.4 g of crushed dry ice (carbon dioxide) was slowly added. Afterwards, the reaction solution was slowly warmed to 0° C., added with 50 ml of 6N HCl dropwise and then stirred for 1 hour. Next, the reaction solution was extracted by adding ethyl acetate and separating the organic layer from the aqueous layer, and the organic layer was washed with saline and then dried over anhydrous magnesium sulfate. The resulting solution was concentrated under reduced pressure, and then the residue was recrystallized in ethanol to obtain 6.8 g of (S4-3). The yield of (S4-3) from (S4-2) was 59.8%.

Synthesis of Compound (S4-4)

At first, 2.2 g of (S4-3), 0.88 g of 3,4,5-trifluorophenol (S1-8), 0.07 g of dimethylaminopyridine (DMAP) and 100 ml dichloromethane were added into a reactor under nitrogen atmosphere and cooled to 0° C. Next, 30 ml of dicyclohexylcarbo-diimide (DCC) solution in dichloromethane was added dropwise, and the mixture was stirred for 4 hr at the temperature, warmed to room temperature and stirred for 15 hr. Afterwards, the reaction solution was filtered under suction, and the filtrate was sequentially washed with 1N hydrochloric acid, saturated aqueous sodium bicarbonate solution and water and then dried over magnesium sulfate. The solution was concentrated under reduced pressure, and the residue was purified by silica-gel column chromatography with a mixture solvent of heptane/ethyl acetate=4/1 as the eluent and then recrystallized in a mixed solvent of heptane/ethyl acetate=10/1 to obtain 2.2 g of (S4-4). The yield of (S4-4) from (S4-3) was 75.2%.

The phase transition temperature (° C.) of (S4-4) is: K 78.6 N 155.0 I.

The resulting compound was identified as (S4-4) from the following chemical shift (δ, in ppm) data obtained with $^1$H-NMR analysis in which CDCl$_3$ was used as a solvent: 7.56-7.53 (m, 3H), 7.51-7.49 (m, 2H), 7.43 (d, 1H), 7.40 (d, 1H), 7.30 (d, 2H), 7.06-7.01 (m, 2H), 2.65 (t, 2H), 1.74-1.66 (m, 2H) and 0.99 (t, 3H).

Physical Properties of Liquid Crystal Compound (S4-4)

A liquid crystal composition E containing the mother liquid crystal A and (S4-4) obtained in Reference Example 1 in a ratio of 85 wt % to 15 wt % was prepared, and the characteristic values were measured. The extrapolated characteristic values of (S4-4) calculated based on the measurements using the extrapolation method are as follows: $T_{NI}$=93.7° C., $\Delta\varepsilon$=37.0 and $\Delta n$=0.204.

Reference Example 2

Synthesis of Compound (S5-2)

Reference Example 1, except that 4-chloro-3,5-difluorophenol (S5-1) was used instead of (S1-8). The yield of (S5-2) from (S4-3) was 90.3%. The phase transition temperature (° C.) of (S5-2) is: K 95.4 N 192.0 I.

The resulting compound was identified as (S5-2) from the following chemical shift (δ, in ppm) data obtained with $^1$H-NMR analysis in which CDCl$_3$ was used as a solvent: 7.56-7.54 (m, 3H), 7.50-7.49 (m, 2H), 7.44 (d, 1H), 7.40 (d, 1H), 7.30 (d, 2H), 7.06-7.03 (m, 2H), 2.66 (t, 2H), 1.73-1.66 (m, 2H) and 0.99 (t, 3H).

Physical Properties of Liquid Crystal Compound (S5-2)

A liquid crystal composition F containing the mother liquid crystal A and (S5-2) obtained in Reference Example 2 in a ratio of 85 wt % to 15 wt % was prepared, and the characteristic values were measured. The extrapolated characteristic values of (S5-2) calculated based on the measurements using the extrapolation method are as follows: $T_{NI}$=110.4° C., $\Delta\varepsilon$=33.7 and $\Delta n$=0.224.

Reference Example 3

Synthesis of Compound (S6-2)

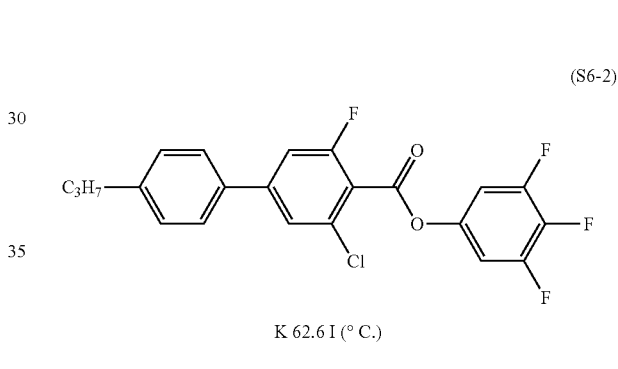

K 62.6 I (° C.)

The synthesis scheme is shown below.

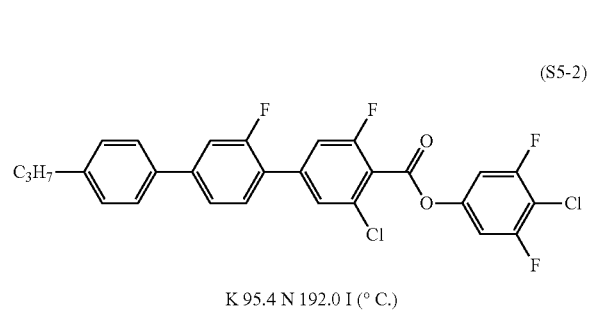

K 95.4 N 192.0 I (° C.)

The synthesis scheme is shown below.

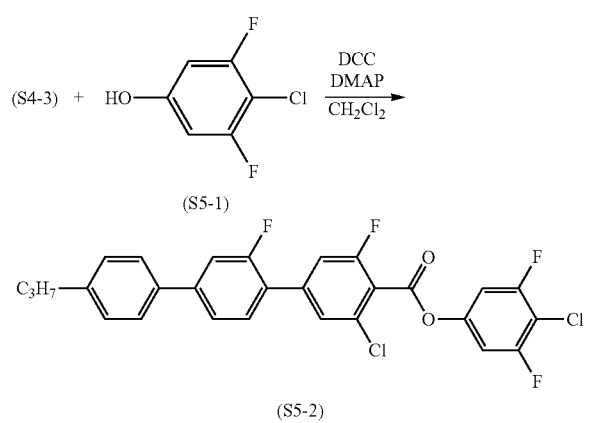

Synthesis of Compound (S5-2)

Synthesis of (S5-2) from (S4-3) was accomplished in a process similar to that for synthesizing (S4-4) from (S4-3) in

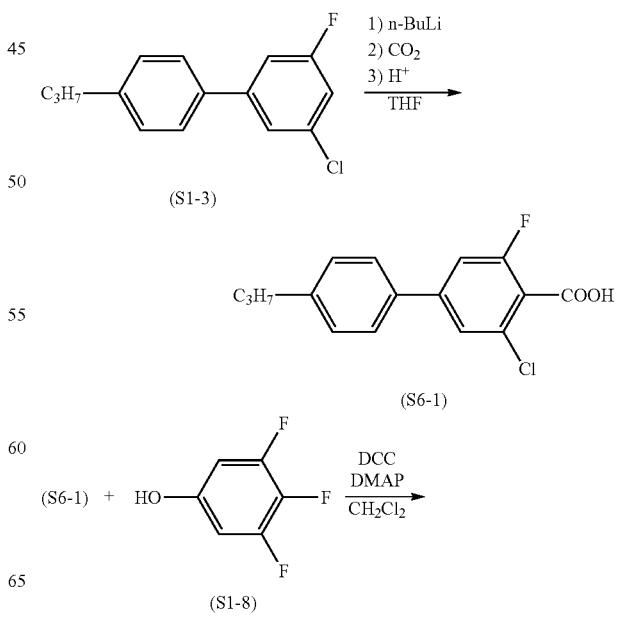

-continued

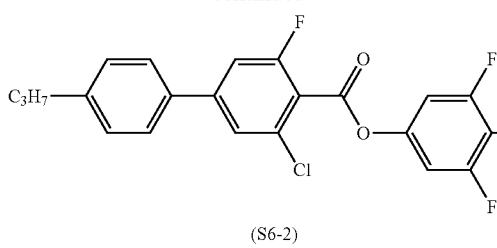

(S6-2)

Synthesis of Compound (S6-1)

Synthesis of (S6-1) from (S1-3) was accomplished in a process similar to that for synthesizing (S4-3) from (S4-2) in Reference Example 1, except that (S1-3) was used instead of (S4-2). The yield of (S6-1) from (S1-3) was 95.0%.

Synthesis of Compound (S6-2)

Synthesis of (S6-2) from (S6-1) was accomplished in a process similar to that for synthesizing (S4-4) from (S4-3) in Reference Example 1, except that (S6-1) was used instead of (S4-3). The yield of (S6-2) from (S6-1) was 77.5%. The phase transition temperature (° C.) of the resulting compound (S6-2) is as follows: K 62.6 I.

The resulting compound was identified as (S6-2) from the following chemical shift (δ, in ppm) data obtained with $^1$H-NMR analysis in which $CDCl_3$ was used as a solvent: 7.51-7.48 (m, 3H), 7.32 (dd, 1H), 7.29 (d, 2H), 7.02-6.99 (m, 2H), 2.65 (t, 2H), 1.71-1.66 (m, 2H) and 0.97 (t, 3H).

Physical Properties of Liquid Crystal Compound (S6-2)

A liquid crystal composition G containing the mother liquid crystal A and (S6-2) obtained in Reference Example 3 in a ratio of 85 wt % to 15 wt % was prepared, and the characteristic values were measured. The extrapolated characteristic values of (S6-2) calculated based on the measurements using the extrapolation method are as follows: $T_{NI}$=−9.6° C., $\Delta\epsilon$=28.3 and $\Delta n$=0.104.

Reference Example 4

Synthesis of Compound (S7-2)

The synthesis scheme is shown below.

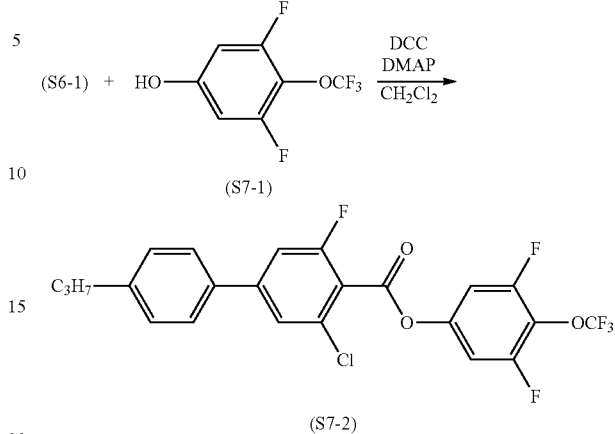

Synthesis of Compound (S7-2)

Synthesis of (S7-2) from (S6-1) is accomplished in a process similar to that for synthesizing (S6-2) from (S6-1) in Reference Example 3, except that 3,5-difluoro-4-trifluoromethoxyphenol (S7-1) was used instead of (S1-8). The yield of (S7-2) from (S6-1) was 74.4%. The phase transition temperature (° C.) of (S7-2) is: K 66.0 I.

The resulting compound was identified as (S7-2) from the following chemical shift (δ, in ppm) data obtained with $^1$H-NMR analysis in which $CDCl_3$ was used as a solvent: 7.53-7.49 (m, 3H), 7.33 (dd, 1H), 7.30 (d, 2H), 7.07-7.05 (m, 2H), 2.65 (t, 2H), 1.71-1.66 (m, 2H) and 0.98 (t, 3H).

Physical Properties of Liquid Crystal Compound (S7-2)

A liquid crystal composition H containing the mother liquid crystal A and (S7-2) obtained in Reference Example 4 in a ratio of 85 wt % to 15 wt % was prepared, and then the characteristic values were measured. The extrapolated characteristic values of (S7-2) calculated based on the measurements using the extrapolation method are as follows: $T_{NI}$=4.4° C., $\Delta\epsilon$=31.7 and $\Delta n$=0.110.

Reference Example 5

Synthesis of Compound (S8-1)

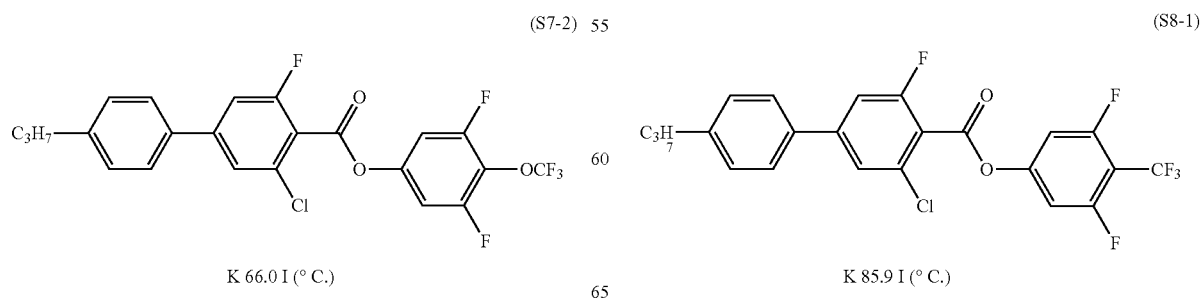

K 66.0 I (° C.)     K 85.9 I (° C.)

The synthesis scheme is shown below.

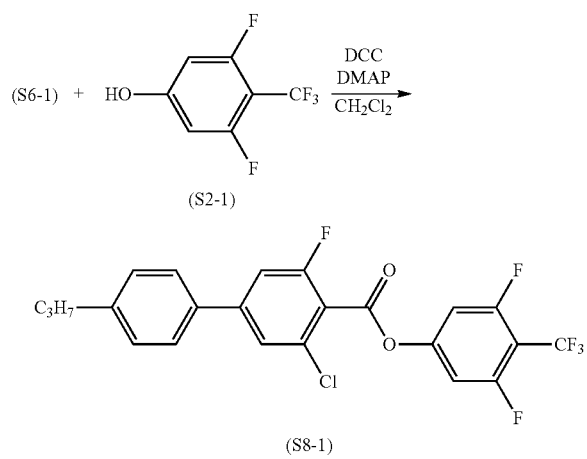

Synthesis of Compound (S8-1)

Synthesis of (S8-1) from (S6-1) was accomplished in a process similar to that for synthesizing (S6-2) from (S6-1) in Reference Example 3, except that 3,5-difluoro-4-trifluoromethylphenol (S2-1) was used instead of (S1-8). The yield of (S8-1) from (S6-1) was 82.9%. The phase transition temperature (° C.) of (S8-1) is: K 85.9 I.

The resulting compound was identified as (S8-1) from the following chemical shift (δ, in ppm) data obtained with $^1$H-NMR analysis in which $CDCl_3$ was used as a solvent: 7.53-7.48 (m, 3H), 7.33 (dd, 1H), 7.30 (d, 2H), 7.06-7.04 (m, 2H), 2.65 (t, 2H), 1.71-1.66 (m, 2H) and 0.97 (t, 3H).

Physical Properties of Liquid Crystal Compound (S8-1)

A liquid crystal composition I containing the mother liquid crystal A and (S8-1) obtained in Reference Example 5 in a ratio of 90 wt % to 10 wt % was prepared, and then the characteristic values were measured. The extrapolated characteristic values of (S8-1) calculated based on the measurements using the extrapolation method are as follows: $T_{NI}$=−6.3° C., Δ∈=40.7 and Δn=0.117.

Reference Example 6

Synthesis of Compound (S9-1)

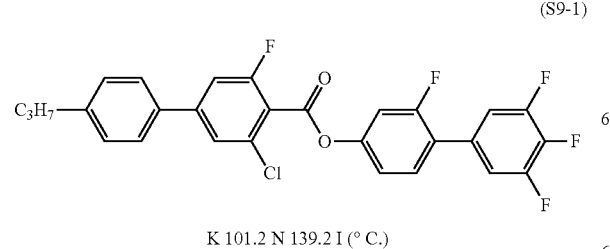

K 101.2 N 139.2 I (° C.)

The synthesis scheme is shown below.

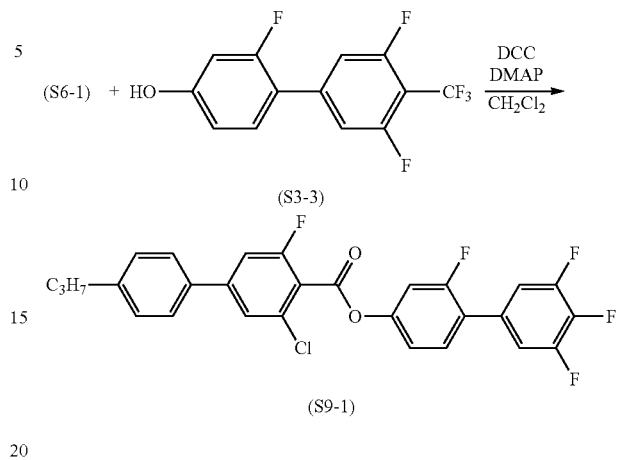

Synthesis of Compound (S9-1)

Synthesis of (S9-1) from (S6-1) was accomplished in a process similar to that for synthesizing (S6-2) from (S6-1) in Reference Example 3, except that (S3-3) was used instead of (S1-8). The yield of (S9-1) from (S6-1) was 63.3%. The phase transition temperature (° C.) of the resulting compound (S9-1) is: K 101.2 N 139.2 I.

The resulting compound was identified as (S9-1) from the following chemical shift (δ, in ppm) data obtained with $^1$H-NMR analysis in which $CDCl_3$ was used as a solvent: 7.53-7.49 (m, 3H), 7.45 (t, 1H), 7.33 (dd, 1H), 7.30 (d, 2H), 7.22-7.17 (m, 4H), 2.66 (t, 2H), 1.71-1.67 (m, 2H) and 0.98 (t, 3H).

Physical Properties of Liquid Crystal Compound (S9-1)

A liquid crystal composition J containing the mother liquid crystal A and (S9-1) obtained in Reference Example 6 in a ratio of 95 wt % to 5 wt % was prepared, and then the characteristic values were measured. The extrapolated characteristic values of (S9-1) calculated based on the measurements using the extrapolation method are as follows: $T_{NI}$=69.7° C., Δ∈=33.7 and Δn=0.177.

Example 4

Synthesis of Compound (S10-1)

Compound (S10-1) is a compound of formula (1-2A) in which $R^1$ is $C_5H_{11}$, $L^2$, $L^4$ and $L^5$ are all fluorine and $X^I$ is —$CF_3$.

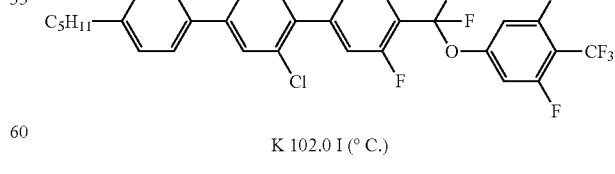

K 102.0 I (° C.)

Synthesis of Compound (S10-1)

The synthesis of (S10-1) was accomplished in a process similar to that for synthesizing (S1-9) from (S1-1) in Example 1, except that 4-pentylphenylboric acid was used instead of (S1-1) and 3,5-difluoro-4-trifluoromethylphenol (S2-1) used instead of (S1-8). The phase transition temperature (° C.) of (S10-1) is: K 102 I.

Physical Properties of Liquid Crystal Compound (S10-1)

A liquid crystal composition K containing the mother liquid crystal A and (S10-1) obtained in Example 4 in a ratio of 95 wt % to 5 wt % was prepared, and then the characteristic values were measured. The extrapolated characteristic values of (S10-1) calculated based on the measurements using the extrapolation method are as follows: $T_{NI}$=33.7° C., $\Delta\in$=56.2 and $\Delta n$=0.157.

It can be seen from the results that the liquid crystal compound (S10-1) has a large dielectric anisotropy ($\Delta\in$) and a large optical anisotropy ($\Delta n$).

Composition of this Invention

In this invention, the characteristic values of a liquid crystal composition were measured by the methods below. The methods are mainly those described in EIAJ•ED-2521A of the Standard of Electric Industries Association of Japan, or modifications of the same. The TN device used in the measurement was not equipped with TFTs.

Upper-limit temperature of nematic phase (NI, ° C.): a sample was placed on a hot plate in a melting point measuring apparatus equipped with a polarization microscope, and heated at a rate of 1° C./min. The temperature at which a part of the sample started to change from a nematic phase to an isotropic liquid was recorded as the upper-limit temperature of the nematic phase, which is often called "upper-limit temperature".

Lower-limit temperature of a nematic phase ($T_C$, ° C.): samples having a nematic phase was kept in a freezer respectively at 0° C., −10° C., −20° C., −30° C. and −40° C. for 10 days, and observed for the liquid crystal phase. For example, in a case where the sample exhibited a nematic phase at −20° C. and changed to a crystal or a smectic phase at −30° C., the $T_C$ is recorded as ≤−20° C. The lower-limit temperature of a nematic phase is often called "lower-limit temperature".

Transition temperature of an optically isotropic liquid crystal phase: a sample was placed on a hot plate in a melting point measuring apparatus equipped with a polarization microscope with crossed Nicols, which was initially heated to a temperature allowing the sample to form an isotropic phase, and then cooled at a rate of 1° C./min until a chiral nematic phase or an optically isotropic liquid crystal phase was completely formed. The phase transition temperature during this cooling process was measured. Then, the temperature was raised at a rate of 1° C./min, and the phase transition temperature during this heating process was measured. In this invention, unless specifically indicated, the phase transition temperature in the heating process was recorded as the phase transition temperature. When it was difficult to determine the phase transition temperature of the optically isotropic liquid crystal phase in a dark field under crossed Nicols, the phase transition temperature could be determined after the polarizing plate is deviated from the crossed Nicols state by 1-10 degrees.

Viscosity ($\eta$, determined at 20° C., mPa·s): The viscosity was measured with an E-type rotational viscometer.

Rotational viscosity ($\gamma 1$, determined at 25° C., mPa·s):

1) For a sample with a positive dielectric anisotropy: the measurement was carried out according to the method described in M. Imai et al., *Molecular Crystals and Liquid Crystals*, Vol. 259, 37 (1995). The sample was placed into a TN device with a twist angle of 0 degree and a distance (cell gap) of 5 μm between two glass substrates. The TN device was applied with a voltage in a range of 16 to 19.5 V stepwise by 0.5 V. After a period of 0.2 s without voltage application a voltage application was repeated with a rectangular wave (rectangular pulse of 0.2 s) followed by a period of 2 s without voltage application. The peak current and the peak time of the transient current resulted from the application of the voltage were measured. Then, the value of rotational viscosity was calculated according to the measurements and the Equation (8) described in page 40 of the paper of M. Imai et al. The dielectric anisotropy value required for this calculation was obtained by using the device used in the measurement of the rotational viscosity, according to the method for determining dielectric anisotropy below.

2) For a sample with a negative dielectric anisotropy: the measurement was carried out according to the method described in M. Imai et al., *Molecular Crystals and Liquid Crystals*, Vol. 259, 37 (1995). The sample was placed into a vertical alignment (VA) device with a distance (cell gap) of 20 μm between two glass substrates. The device was applied with a voltage in a range of 30 to 50 V stepwise by 1 V. After a period of 0.2 s without voltage application, a voltage application was repeated with a rectangular wave (rectangular pulse of 0.2 s) followed by a period of 2 s without voltage application. The peak current and the peak time of the transient current resulted from the application of the voltage were measured. Then, the value of rotational viscosity was calculated according to the measurements and the Equation (8) described in page 40 of the paper of M. Imai et al. The dielectric anisotropy value required for this calculation was obtained by using the method below.

Optical anisotropy ($\Delta n$, determined at 25° C.): the measurement was carried out by using light having a wavelength of 589 nm, with an Abbe refractometer having a polarizing plate mounted on the ocular lens. After the surface of the main prism was rubbed in a direction, the sample was dropped onto the main prism. The refractive index $n_{\parallel}$ was determined when the polarizing direction was paralleled to the rubbing direction, and the refractive index $n_{\perp}$ was determined when the polarizing direction was perpendicular to the rubbing direction. The value of optical anisotropy was calculated according the equation "$\Delta n = n_{\parallel} - n_{\perp}$". When the sample was a composition, the above process could be used to determine the optical anisotropy. When the sample was a compound, the compound could be mixed with a suitable composition and then determined for the optical anisotropy of the mixture. In this case, the optical anisotropy of the compound was an extrapolated value.

Dielectric anisotropy ($\Delta\in$, determined at 25° C.): when the sample was a compound, the compound could be mixed with a suitable composition and then determined for the dielectric anisotropy. In this case, the dielectric anisotropy of the compound was an extrapolated value.

1) For a composition with a positive dielectric anisotropy: a sample was placed into a liquid crystal cell with a distance (gap) of about 9 μm between two glass substrates and a twist angle of 80 degrees. The liquid crystal cell was applied with a voltage of 20 V to determine the dielectric constant $\in_{\parallel}$ in the major-axis direction of the liquid crystal molecule. Then, a voltage of 0.5 V was applied to determine the dielectric constant $\in_{\perp}$ in the minor-axis direction of the liquid crystal molecule. The value of dielectric anisotropy was calculated according to the equation "$\Delta\in = \in_{\parallel} - \in_{\perp}$".

2) For a composition with a negative dielectric anisotropy: a sample was placed into a liquid crystal cell, which was processed into homeotropic alignment, and applied with a voltage of 0.5 V to determine the dielectric constant $\in_{\parallel}$. Then, the sample was placed into a liquid crystal cell, which was processed into homogeneous alignment, and applied with a voltage of 0.5 V to determine the dielectric constant $\in_{\perp}$. The value of dielectric anisotropy was calculated according to the equation "$\Delta\in=\in_{\parallel}-\in_{\perp}$".

Threshold voltage (Vth, determined at 25° C., V): when the sample was a compound, the compound could be mixed with a suitable composition and then measured for the threshold voltage. In this case, the threshold voltage of the compound was an extrapolated value.

1) For a composition with a positive dielectric anisotropy: a sample was placed into an LCD device of a normally white mode with a distance (gap) of (0.5/Δn) μm between the two glass substrates and a twist angle of 80 degrees, in which Δn was the value of the optical anisotropy determined by the above method. A rectangular wave with a frequency of 32 Hz was applied to the device. Then, the voltage of rectangular wave was increased, and the voltage value at which the transmittance of light through the device reached 90% was determined.

2) For a composition with a negative dielectric anisotropy: a sample was placed into an LCD device of a normally black mode with a distance (gap) of about 9 μm between the two glass substrates, which was processed into homeotropic alignment. A rectangular wave with a frequency of 32 Hz was applied to the device. Then, the voltage of rectangular wave was increased, and the voltage value at which the transmittance of light through the device reached 10% was determined.

Voltage holding ratio (VHR, determined at 25° C., %): the TN device used for the determination had a polyimide alignment film and a distance (cell gap) of 6 μm between two glass substrates. A sample was placed into the device, which was then sealed with a UV-polymerizable adhesive. Then, the TN device was charged by applying a pulse voltage (5V, 60 ms). The voltage decay was determined by using a high-speed voltmeter at an interval of 16.7 ms, and the area A between the voltage curve and the horizontal axis per unit cycle was calculated. The voltage holding ratio was the percentage of the area A relative to the non-decayed area B.

Helical pitch (determined at 20° C., μm): The helical pitch was measured according to the wedge cell method of Grandjean-Cano. A sample was injected into a wedge cell of Grandjean-Cano, and then the distance (a, in μm) between the disclination lines observed from the wedge cell was measured. The helical pitch (p) could be calculated according to the equation "$p=2\cdot a\cdot\tan\theta$", in which θ is the angle between the two glass plates in the wedge cell.

Alternatively, the pitch length can be determined through selective reflection (Handbook of Liquid Crystal, p 196, issued in 2000, by Maruzen). For the selective reflection wavelength λ, the relationship $<n>p/\lambda=1$ exists, wherein $<n>$ denotes the average refractive index and can be calculated by the equation "$<n>=\{(n_{\parallel}^2+n_{\perp}^2)/2\}^{1/2}$". The selective reflection wavelength was determined with a microspectrophotometer (trade name MSV-350, made by Japan Electronics Co., Ltd). The pitch was obtained by dividing the resulting reflection wavelength with the average refractive index.

When the concentration of the chiral dopant is low, the pitch of a cholesteric liquid crystal having a reflection wavelength at the long wavelength side of visible light is proportional to the reciprocal of the concentration. Therefore, multiple points were measured in the pitch length of the liquid crystal having selective reflection wavelength in the visible light region, and the pitch was calculated by linear extrapolation.

The proportion (percentage) of a component or a liquid crystal compound is weight percentage (wt %) based on the total weight of the liquid crystal compounds. The composition can be prepared by mixing the components including liquid crystal compounds after weighing them. Thus, the wt % of each component can be easily calculated.

Composition Example 1

A liquid crystal composition A was prepared by mixing the liquid crystal compounds shown below in the following ratios.

For each structure formula shown below, a description of its correspondence to the above general formulae of this invention, i.e., the compound number, is provided at its right side.

Liquid Crystal Composition A

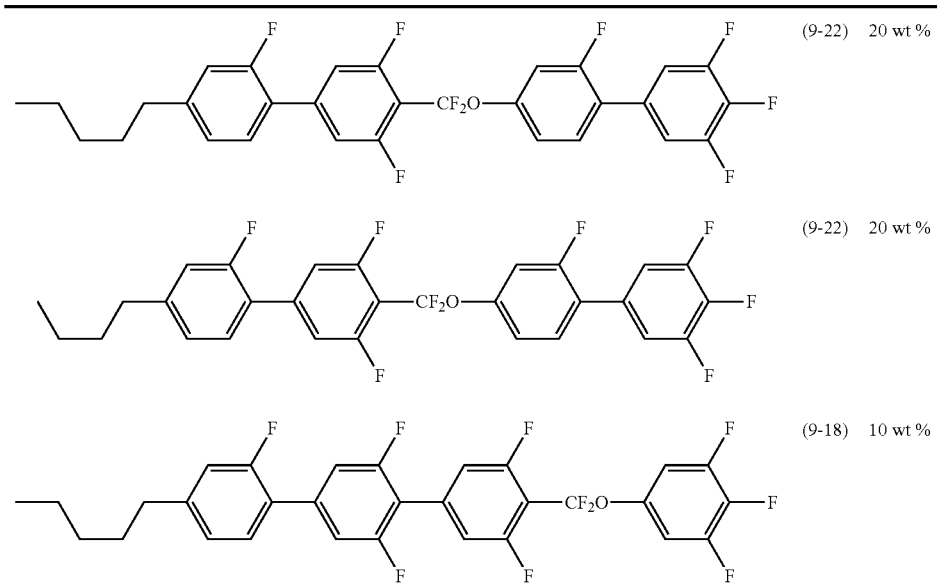

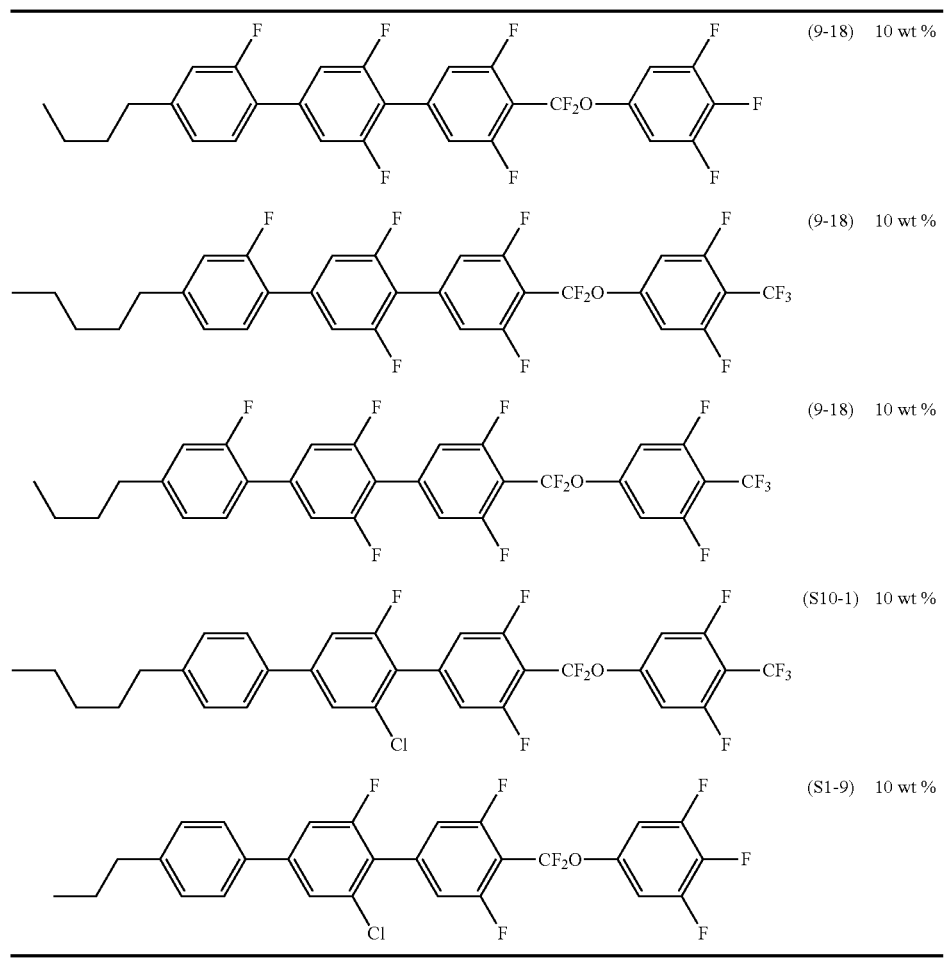

Next, a liquid crystal composition B containing the liquid crystal composition A (94 wt %) and the chiral dopant ISO-6OBA2 (6 wt %) shown below was prepared.

SO-60BA2 was obtained by reacting isosorbitol with 4-hexyloxybenzoic acid to form an ester in the presence of dicyclohexylcarbodiimide (DCC) and 4-dimethylaminopyridine.

ISO-6OBA2:

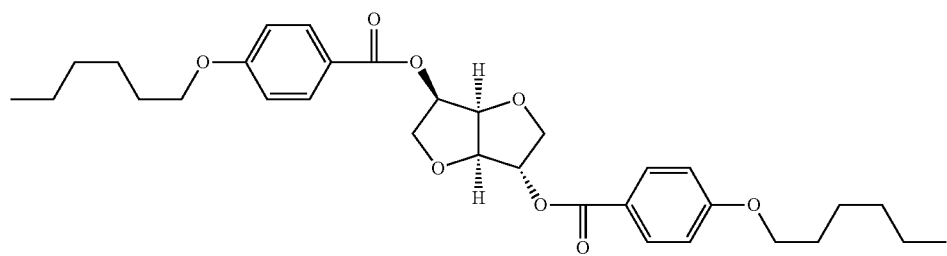 [SMILES: CCCCCCOc1ccc(C(=O)O[C@H]2CO[C@H]3[C@@H]2OC[C@H]3OC(=O)c2ccc(OCCCCCC)cc2)cc1]

Application Example 1

Preparation of Mixture of Monomer with Liquid Crystal Composition

As a mixture of liquid crystal composition and monomer, a liquid crystal composition C-1M is prepared by mixing 79.4 wt % of the liquid crystal composition B, 10.0 wt % of n-dodecyl acrylate, 10.0 wt % of 1,4-di(4-(6-(acryloxy)hexyloxy)-benzoyloxy)-2-methylbenzene and 0.6 wt % of 2,2'-dimethoxyphenylacetophenone as a photo-polymerization initiator.

Preparation of Polymer/Liquid Crystal Composite Material

The liquid crystal composition C-1M was held between a non-aligned comb-like electrode substrate and the opposite glass substrate (without electrode) with a cell thickness of 10 μm, and then the resulting liquid crystal cell was heated until an isotropic phase was formed at 63.0° C. In this state, the cell was irradiated with UV light of 365 nm at an intensity of 23 mWcm$^{-2}$ for 1 min for polymerization.

The polymer/liquid crystal composite material C-1P thus prepared could maintain an optically isotropic liquid crystal phase even being cooled to room temperature.

Further, as shown in FIG. 1, the electrodes on the comb-like electrode substrate were structured such that the electrode 1 extending from the left side and the electrode 2 extending from the right side were alternatively arranged. Thus, as there is a potential difference between the electrodes 1 and 2, the comb-like electrode substrate is provided with an electric field in two directions (upward and downward), as shown in FIG. 1.

Application Example 2

Figure 2:
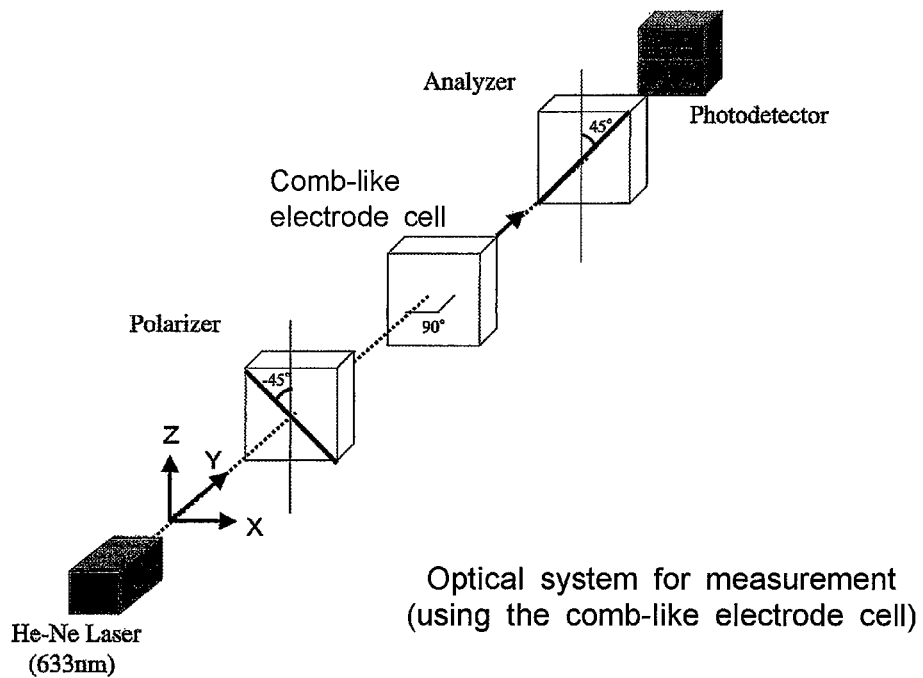
FIG. 2 shows the optical system used in Application Example 2.

A liquid crystal cell holding the polymer/liquid crystal composite material C-1P obtained in Application Example 1 was arranged in the optical system of FIG. 2 to measure the electrooptic properties. The light source was the white light source with a polarization microscope (ECLIPSE LV100POL, made by Nikon). The liquid crystal cell was arranged in the optical system in a manner such that the incident light from the light source irradiated on the liquid crystal cell was perpendicular to the surface thereof, and the line direction of the comb-like electrode was at 45 degrees with respect to the polarizer and the analyzer respectively. The relationship between the applied voltage and the transmittance was investigated by setting the measuring temperature at the clear point (59.1° C.−40° C.=19.1° C.). When a rectangular wave of 47.6 V was applied, the transmittance was up to 80%, and the transmitted light intensity was saturated.

INDUSTRIAL APPLICABILITY

This invention is applicable, for example, to the field of optical device, such as display device using liquid crystal medium.

What is claimed is:

1. A liquid crystal compound, represented by formula (1):

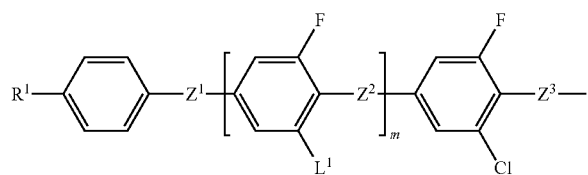

(1)

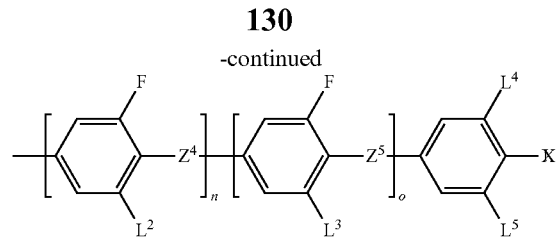

wherein in formula (1), $R^1$ is hydrogen or a $C_{1-20}$ alkyl in which arbitrary —$CH_2$— may be substituted with —O—, —S—, —COO—, —OCO—, —CH=CH—, —CF=CF— or —C≡C—, and arbitrary hydrogen in the alkyl and the group formed by substituting arbitrary —$CH_2$— in the alkyl with —O—, —S—, —COO—, —OCO—, —CH=CH—, —CF=CF— or —C≡C— may be substituted with halogen or $C_{1-3}$ alkyl; $Z^1$, $Z^2$, $Z^3$, $Z^4$ and $Z^5$ are independently a single bond or —$CF_2$O— but are not all single bonds; $L^1$, $L^2$, $L^3$, $L^4$ and $L^5$ are independently hydrogen or fluorine; $X^1$ is hydrogen, halogen, —C≡N, —N=C=S, —C≡c—C≡N, —$SF_5$, or $C_{1-10}$ alkyl in which arbitrary —$CH_2$— may be substituted with —O—, —S—, —CH=CH— or —C≡C— and arbitrary hydrogen may be substituted with halogen; m is 0, 1 or 2, n and o are independently 0 or 1, and 1≤m+n+o≤2; and when m is 2, the plural $L^1$ may be different from each other and the plural $Z^2$ may be different from each other.

2. The liquid crystal compound of claim 1, wherein in formula (1), $R^1$ is $C_{1-20}$ alkyl in which arbitrary —$CH_2$— may be substituted with —O—, —COO— or —CH=CH—; $X^1$ is halogen, —C≡N, —N=C=S, or $C_{1-10}$ alkyl in which two or more hydrogen atoms are substituted with fluorine and arbitrary —$CH_2$— may be substituted with —O—, —S—, —CH=CH— or —C≡C—.

3. The liquid crystal compound of claim 1, wherein in formula (1), $R^1$ is $C_{1-20}$ alkyl, $C_{2-21}$ alkenyl or $C_{1-19}$ alkoxy, and $X^1$ is fluorine, chlorine, —$CF_3$ or —$OCF_3$.

4. The liquid crystal compound of claim 1, wherein in formula (1), $R^1$ is $C_{1-20}$ alkyl, and $X^1$ is fluorine, chlorine or —$CF_3$.

5. The liquid crystal compound of claim 1, wherein m+n+o=1.

6. The liquid crystal compound of claim 1, wherein m+n+o=2.

7. The liquid crystal compound of claim 1, represented by any one of formulae (1-1B), (1-1C), (1-1E), (1-1F) and (1-2A) to (1-2C):

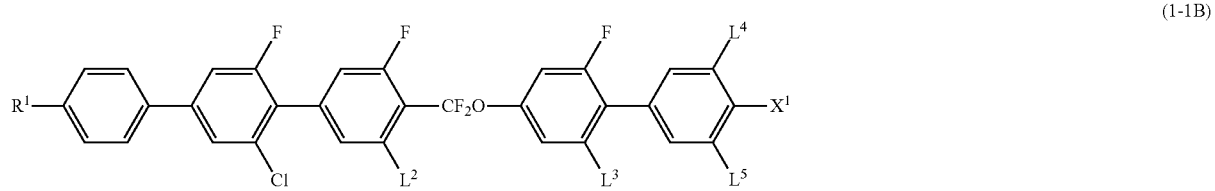

(1-1B)

-continued

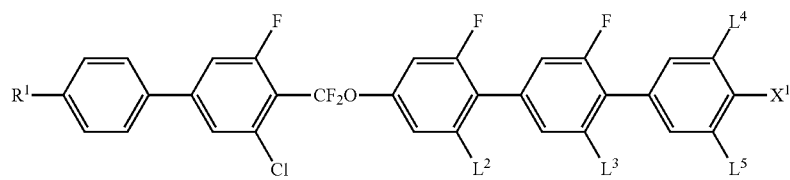
(1-1C)

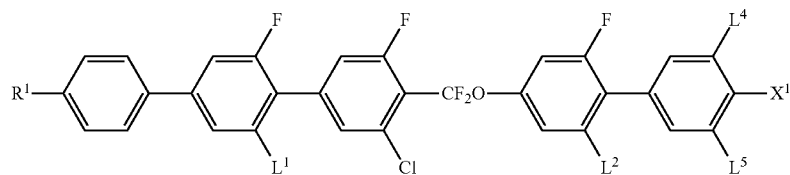
(1-1E)

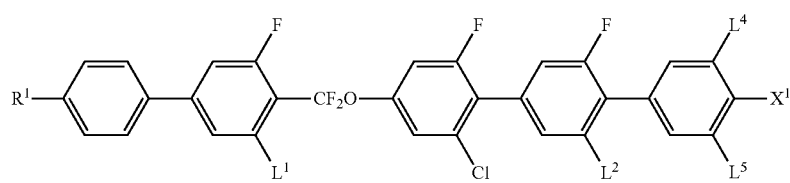
(1-1F)

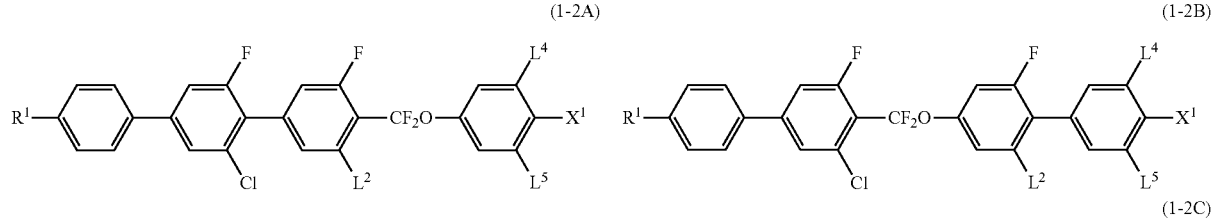
(1-2A) (1-2B)

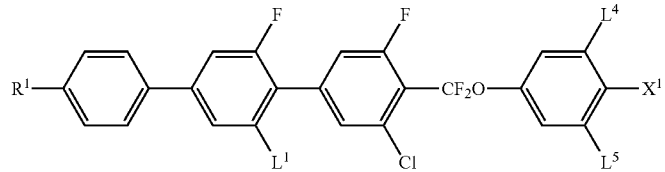
(1-2C)

wherein in the formulae, R¹ has a structure shown in formulae (CHN-1) to (CHN-8) in which $R^{1a}$ is hydrogen or $C_{1-10}$ alkyl, and $X^1$ is fluorine, chlorine, —CF₃ or —OCF₃:

$R^{1a}$—  (CHN-1)

(CHN-2) through (CHN-6) structures with $R^{1a}$ groups

-continued

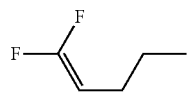
(CHN-7)

(CHN-8)

8. The liquid crystal compound of claim 7, wherein in formulae (1-1B), (1-1E) and (1-2A) to (1-2C), R¹ has a structure shown in formulae (CHN-1) to (CHN-6) in which $R^{1a}$ is hydrogen or a $C_{1-10}$ alkyl, and $X^1$ is fluorine, chlorine, —CF₃ or —OCF₃.

9. The liquid crystal compound of claim 7, wherein in formulae (1-1B), (1-1E) and (1-2A) to (1-2C), R¹ has a structure shown in formulae (CHN-1) to (CHN-6) in which $R^{1a}$ is hydrogen or a $C_{1-10}$ alkyl, $X^1$ is fluorine, chlorine, —CF₃ or —OCF₃, and both L⁴ and L⁵ are fluorine.

10. A liquid crystal compound, represented by formula (1-1B-a) or (1-2A-a):

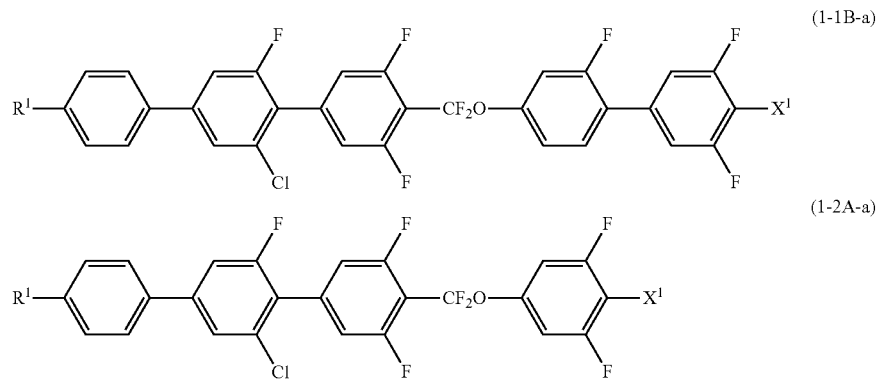
wherein in the formulae, $R^1$ is $C_{1-20}$ alkyl or $C_{2-20}$ alkenyl, and $X^1$ is fluorine or $-CF^3$.
* * * * *